US010435418B2

(12) United States Patent
Tuttle et al.

(10) Patent No.: US 10,435,418 B2
(45) Date of Patent: *Oct. 8, 2019

(54) RAPID AND EFFICIENT BIOORTHOGONAL LIGATION REACTION AND BORON-CONTAINING HETEROCYCLES USEFUL IN CONJUNCTION THEREWITH

(71) Applicant: The Research Foundation for The State University of New York, Binghamton, NY (US)

(72) Inventors: Susan Bane Tuttle, Vestal, NY (US); Ozlem Dilek, Istanbul (TR); Kamalika Mukherjee, Binghamton, NY (US)

(73) Assignee: The Research Foundation for the State University o, Binghamton, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/700,911

(22) Filed: Sep. 11, 2017

(65) Prior Publication Data

US 2018/0065993 A1  Mar. 8, 2018

Related U.S. Application Data

(62) Division of application No. 14/694,744, filed on Apr. 23, 2015, now Pat. No. 9,758,533.

(60) Provisional application No. 61/983,396, filed on Apr. 23, 2014.

(51) Int. Cl.
| | |
|---|---|
| C07F 5/02 | (2006.01) |
| A61K 31/69 | (2006.01) |
| C07K 14/765 | (2006.01) |
| C07K 16/40 | (2006.01) |
| C07K 16/28 | (2006.01) |
| C01B 35/14 | (2006.01) |
| C01B 35/10 | (2006.01) |
| C07H 21/00 | (2006.01) |

(52) U.S. Cl.
CPC .............. *C07F 5/025* (2013.01); *A61K 31/69* (2013.01); *C01B 35/10* (2013.01); *C01B 35/146* (2013.01); *C07F 5/02* (2013.01); *C07H 21/00* (2013.01); *C07K 14/765* (2013.01); *C07K 16/2863* (2013.01); *C07K 16/40* (2013.01)

(58) Field of Classification Search
CPC ......... C07F 5/025; A61K 31/69; C01B 35/10; C01B 35/146
USPC .................................................. 544/229, 69
See application file for complete search history.

(56) References Cited

U.S. PATENT DOCUMENTS

| | | |
|---|---|---|
| 3,598,122 A | 8/1971 | Zaffaroni et al. |
| 3,598,123 A | 8/1971 | Zaffaroni et al. |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,151,273 A | 4/1979 | Riegelman et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,327,725 A | 5/1982 | Cortese et al. |
| 4,343,789 A | 8/1982 | Kawata et al. |
| 4,624,848 A | 11/1986 | Lee |
| 4,968,509 A | 11/1990 | Radebaugh et al. |
| 5,033,252 A | 7/1991 | Carter |
| 5,052,558 A | 10/1991 | Carter |
| 5,281,420 A | 1/1994 | Kelm et al. |
| 5,323,907 A | 6/1994 | Kalvelage |
| 5,336,168 A | 8/1994 | Sibalis |
| 5,340,591 A | 8/1994 | Nakano et al. |
| 5,456,923 A | 10/1995 | Nakamichi et al. |
| 5,461,140 A | 10/1995 | Heller et al. |
| 5,516,527 A | 5/1996 | Curatolo |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,700,485 A | 12/1997 | Berde et al. |

(Continued)

FOREIGN PATENT DOCUMENTS

| | | |
|---|---|---|
| WO | WO2009/126691 A1 | 10/2009 |
| WO | WO2013084198 A1 | 6/2013 |

OTHER PUBLICATIONS

Dewar et al. Journal of American Chemical Society, 86, 433-436,1964.*

(Continued)

*Primary Examiner* — Venkataraman Balasubramanian
(74) *Attorney, Agent, or Firm* — Tully Rinckey PLLC; Steven M. Hoffberg

(57) ABSTRACT

A reaction method comprising combining a carbonyl-substituted arylboronic acid or ester and an α-effect amine in aqueous solution at a temperature between about −5 C to 55 C, and a pH between 2 and 8 to produce an adduct. A process is also provided comprising: contacting a boron compound having a boron atom bonded to a $sp^2$ hybridized carbon conjugated with a cis-carbonyl, the boron having at least one labile substituent, with an α-effect amine, in a solvent for a time sufficient to form an adduct, which may proceed to further products.

20 Claims, 38 Drawing Sheets

(56) References Cited

U.S. PATENT DOCUMENTS

| | | |
|---|---|---|
| 5,723,269 A | 3/1998 | Akagi et al. |
| 5,837,280 A | 11/1998 | Kenealy et al. |
| 5,869,090 A | 2/1999 | Rosenbaum |
| 5,977,175 A | 11/1999 | Lin |
| 6,083,518 A | 7/2000 | Lindahl |
| 6,465,014 B1 | 10/2002 | Moroni et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 8,236,783 B2* | 8/2012 | Franz .................. C07F 5/025 514/64 |
| 8,609,383 B2 | 12/2013 | Young et al. |
| 8,632,970 B2 | 1/2014 | Luo et al. |
| 8,637,306 B2 | 1/2014 | Young et al. |
| 9,012,463 B2 | 4/2015 | Chen et al. |
| 9,758,533 B2* | 9/2017 | Tuttle .................. A61K 31/69 |
| 2004/0013734 A1 | 1/2004 | Babcock et al. |
| 2009/0148887 A1 | 6/2009 | Brustad et al. |
| 2009/0253161 A1* | 10/2009 | Franz .................. C07F 5/025 435/29 |
| 2010/0297693 A1 | 11/2010 | Young et al. |
| 2011/0172186 A1* | 7/2011 | Behnke .................. A61K 31/69 514/64 |
| 2011/0207147 A1 | 8/2011 | Jewett et al. |
| 2011/0312027 A1 | 12/2011 | Young et al. |

OTHER PUBLICATIONS

Tickell et al. Organic Letters 15, 860-863, 2013. See also Supporting Information pp. 1-52.*
Dunn et al. Journal of Organic Chemistry, 33, 4483-4486, 1968.*
Skowronska-Serafinowa B. et al., "Arylboronic compounds. I. Some new derivatives of phenylboronic acid", Roczniki Chemii, 1961, 35, 359-364.
International Search Report for Application No. PCT/US2015/026456 dated Aug. 27, 2015.

* cited by examiner

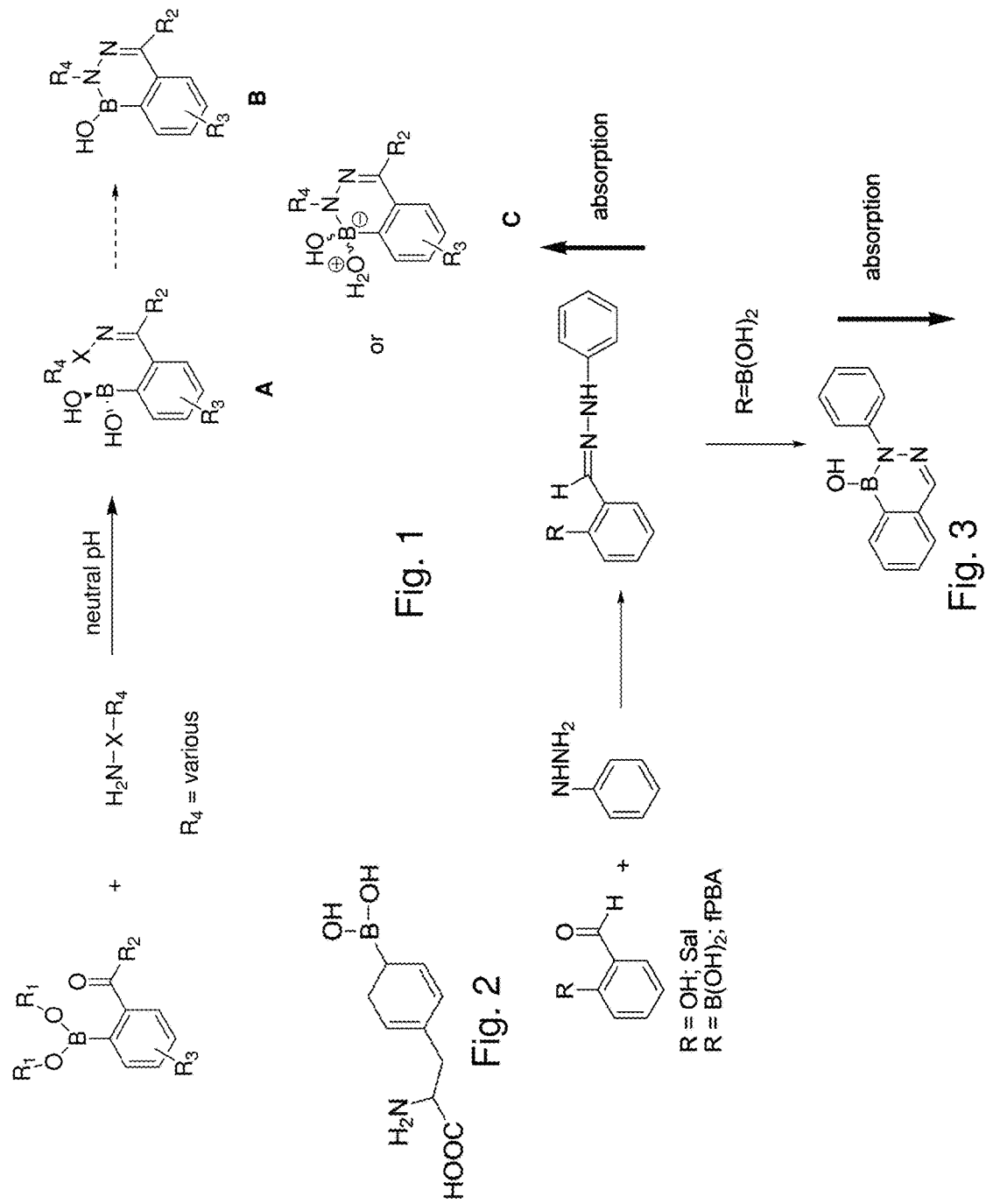

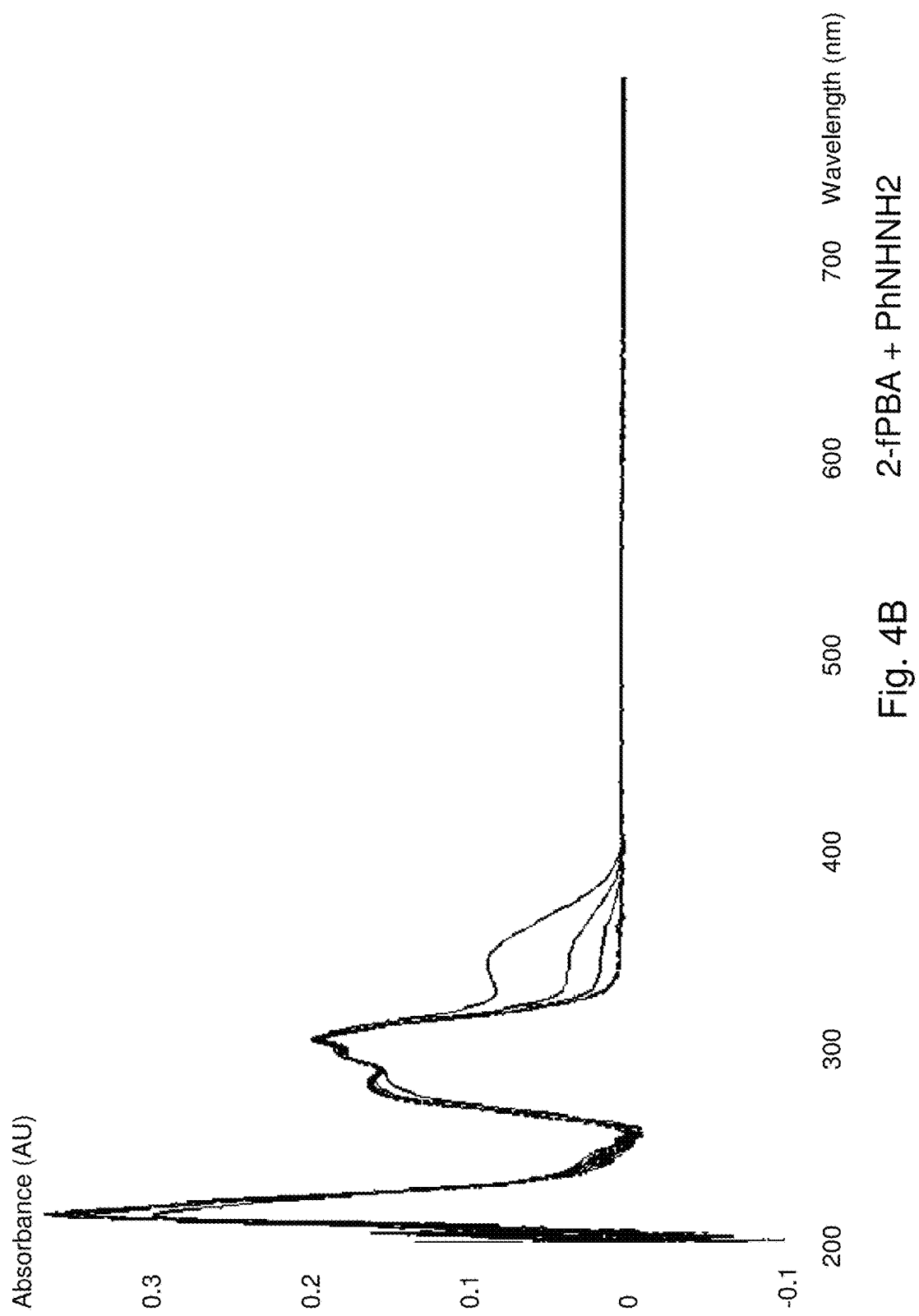
Fig. 4B    2-fPBA + PhNHNH2

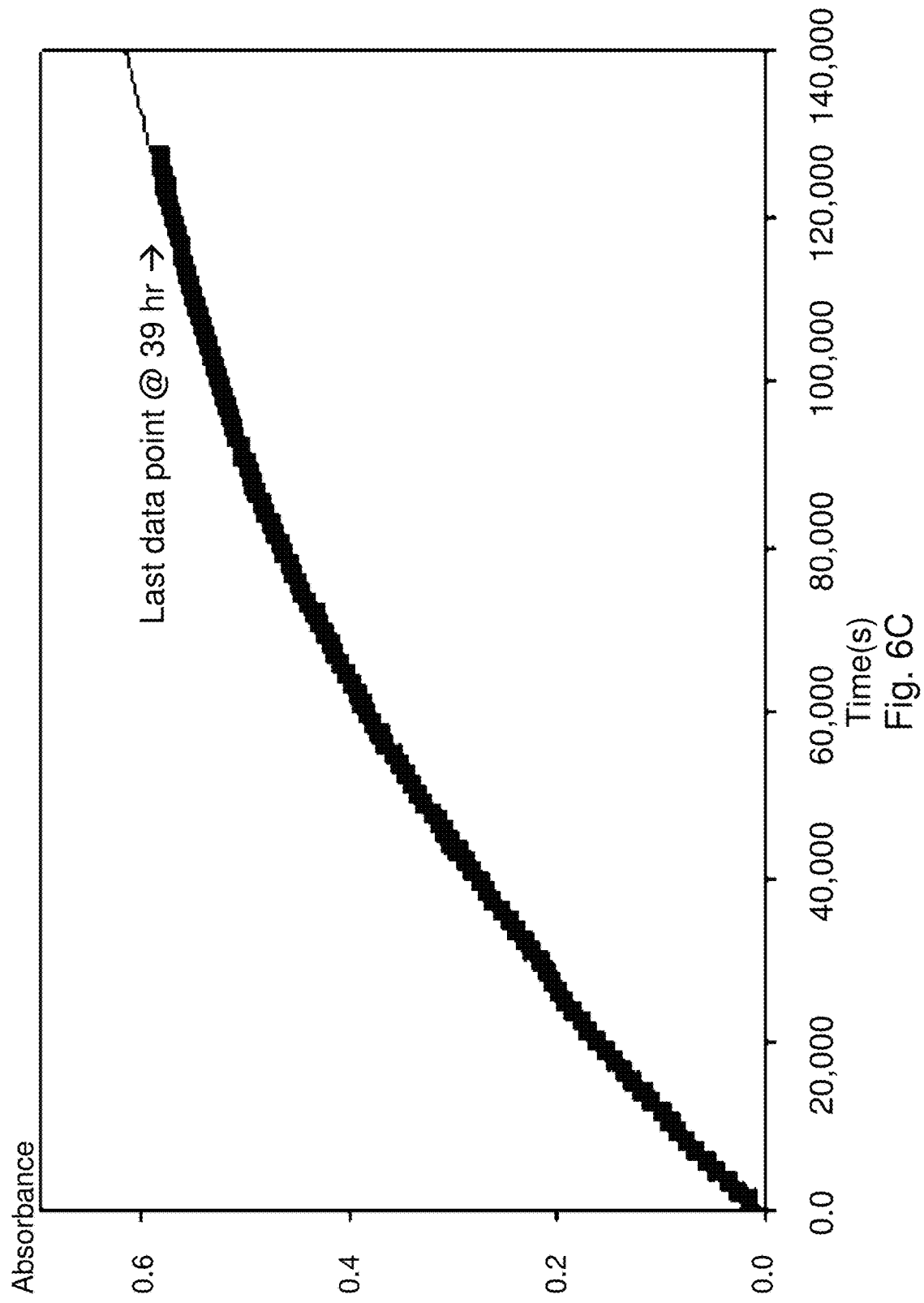

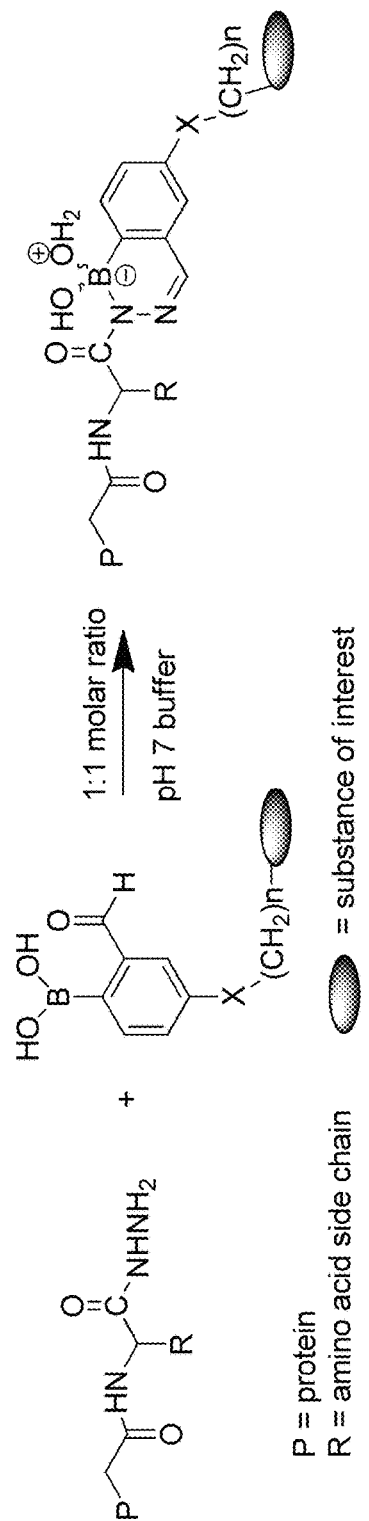
Fig. 15
P = protein
R = amino acid side chain
= substance of interest
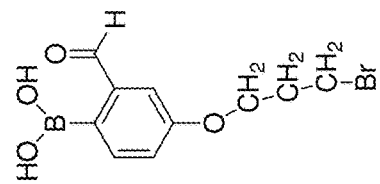
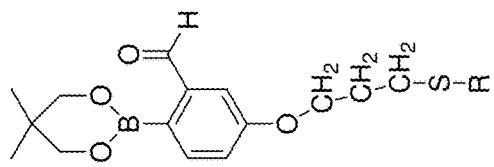
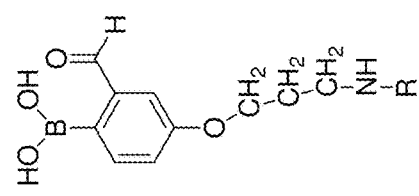
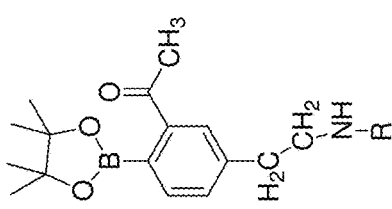
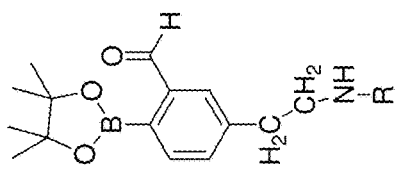
R = H or Ac
Fig. 16

5-(2-aminoethyl)-2-(4,4,5,5-tetramethyl-1,3,2-dioxaborolan-2-yl)benzaldehyde 2-formyl-4-(2-mercaptoethoxy)phenylboronic acid 4-(2-aminoethoxy)-2-formylphenylboronic acid

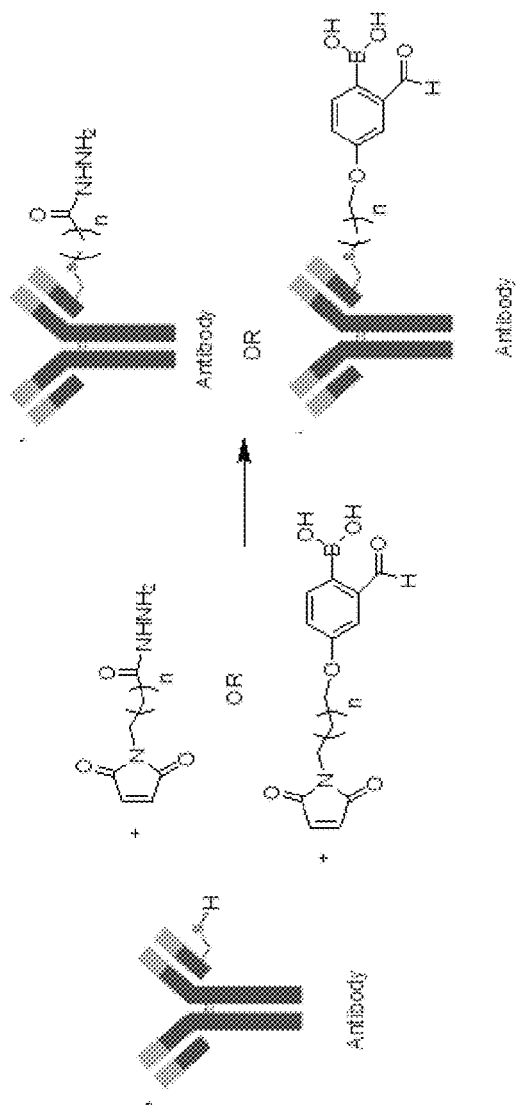
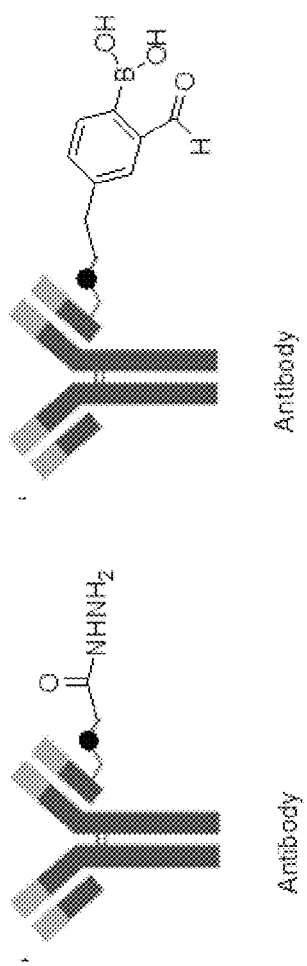
Fig. 24A
Fig. 24B

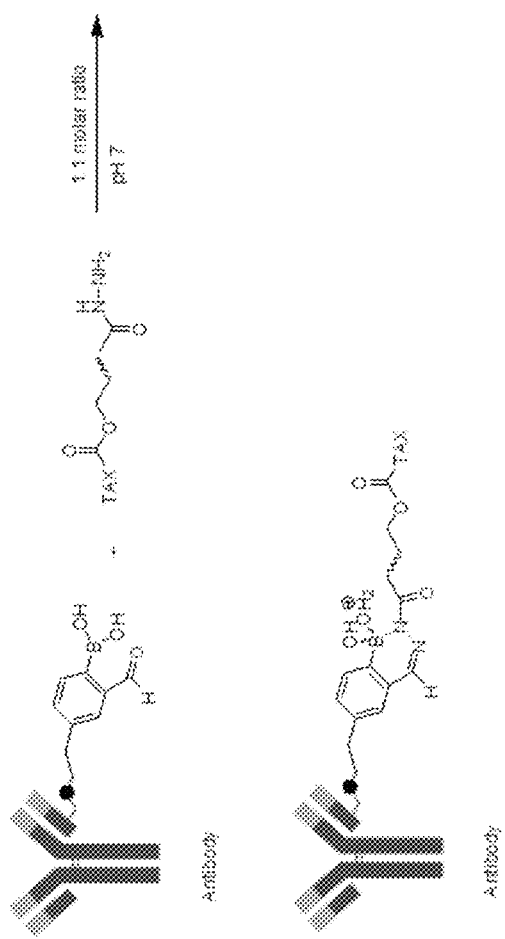
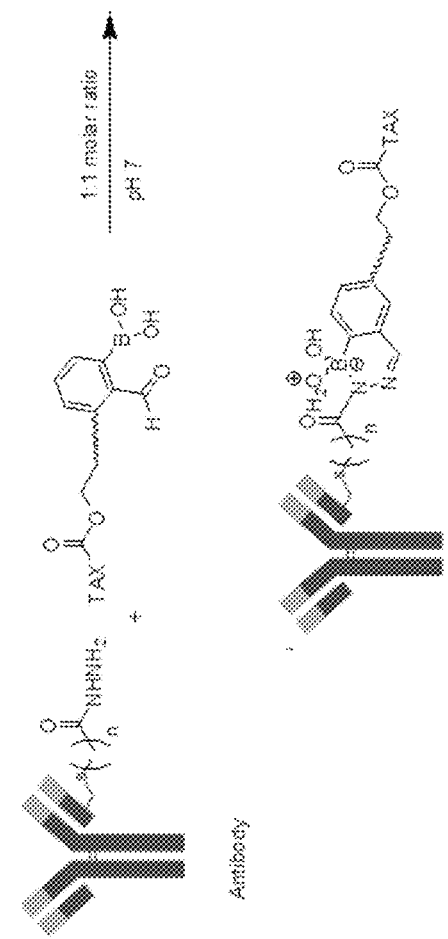
Fig. 25A
Fig. 25B

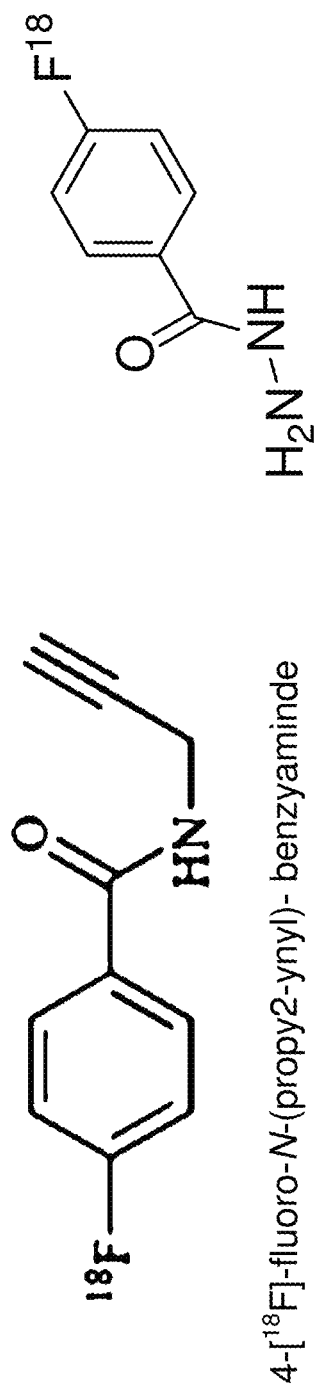
4-[$^{18}$F]-fluoro-N-(propy2-ynyl)- benzyaminde
Fig. 28 (Prior Art)
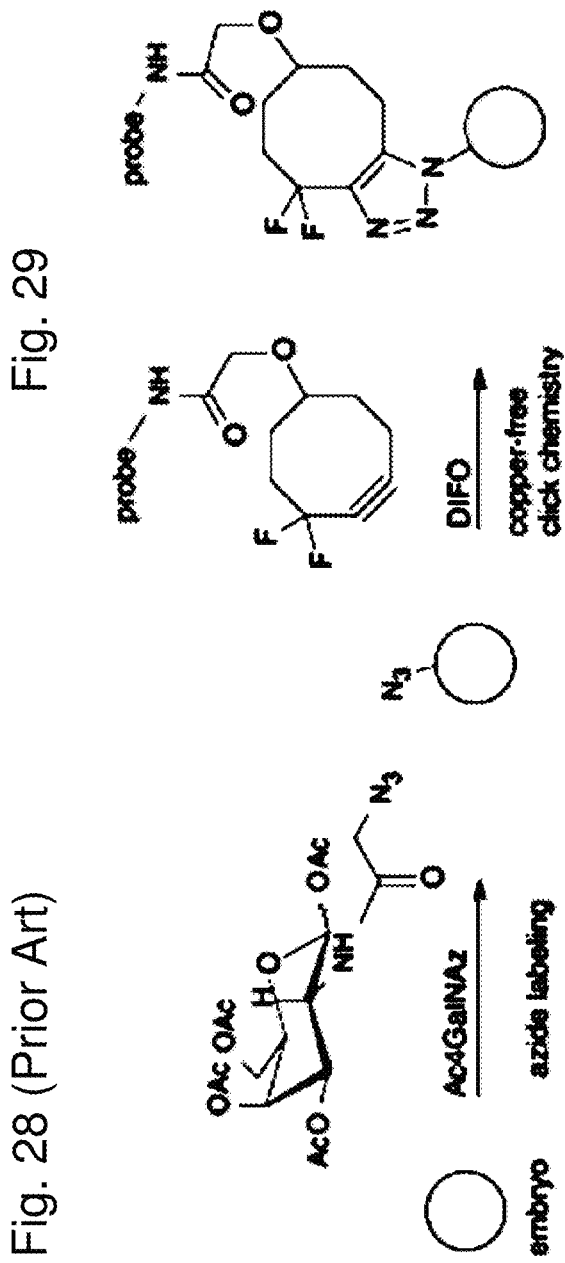
Fig. 29
Fig. 30

Ac4GalN-semicarbazide

Ac4GalNAz

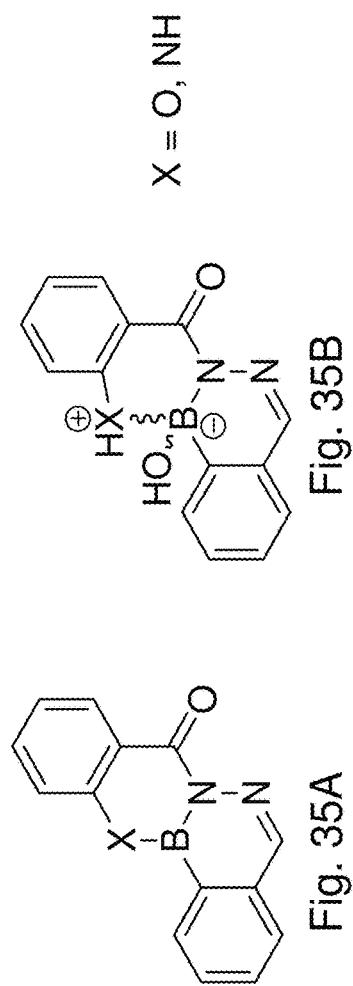
Fig. 35A
Fig. 35B
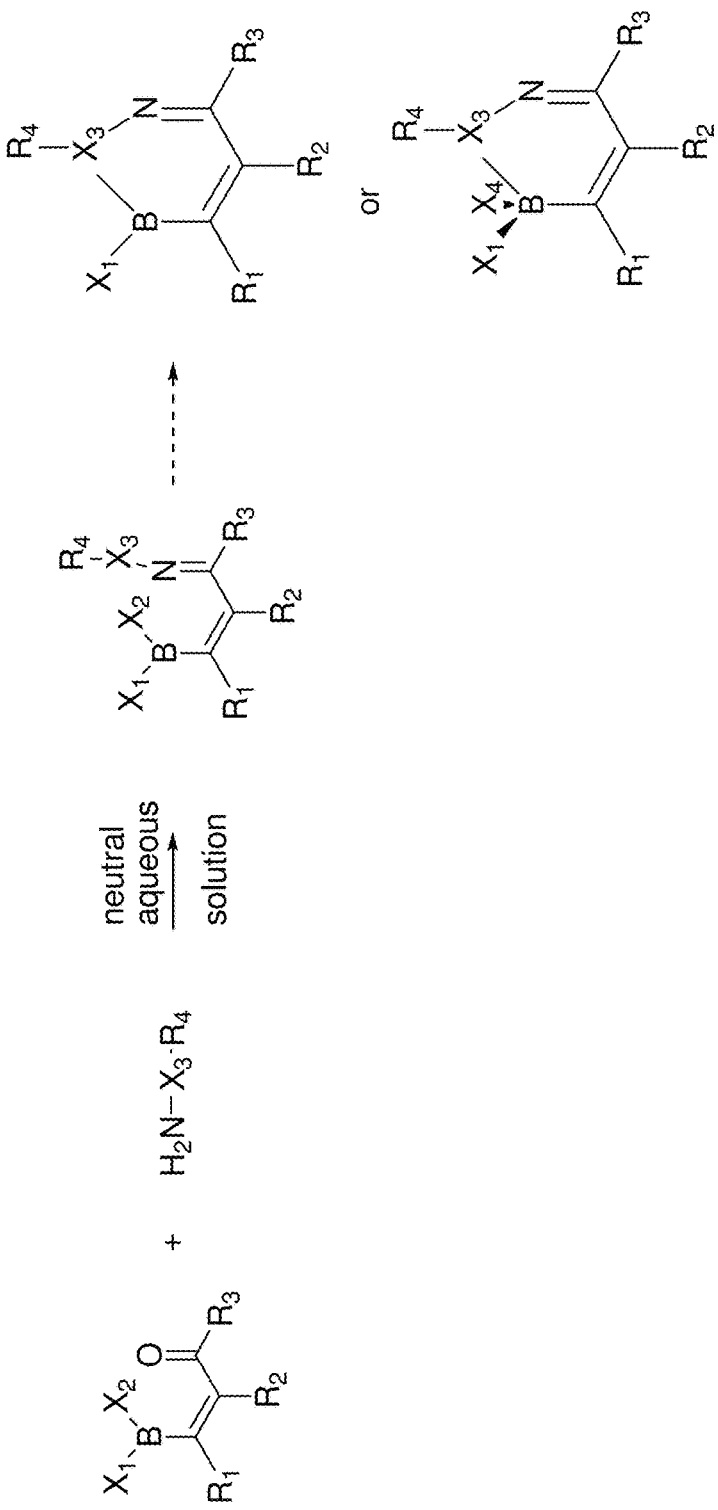
Fig. 36

1 = Zide-BSA + Coumarin 2fPBA
2 = Unmodified BSA + Coumarin 2fPBA

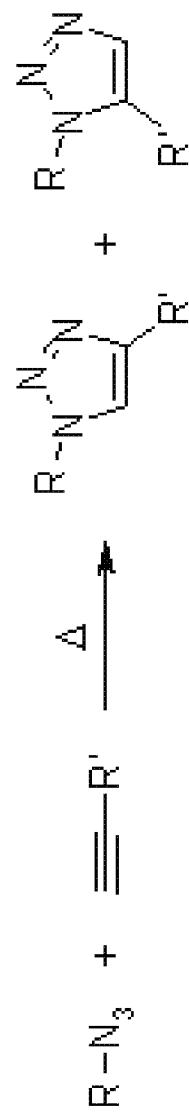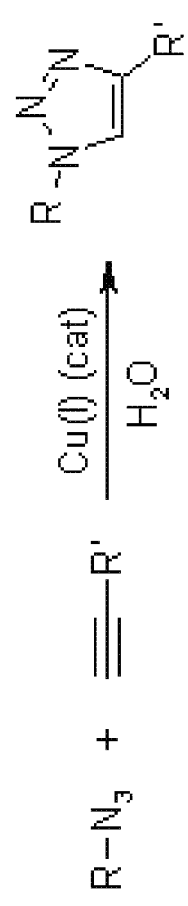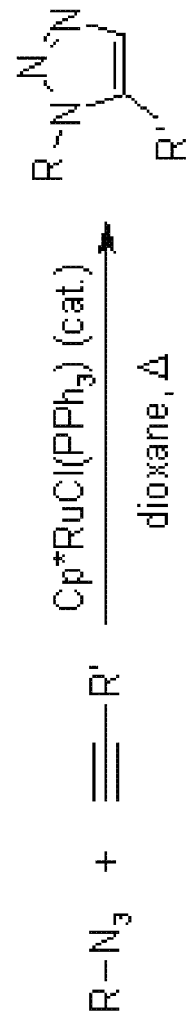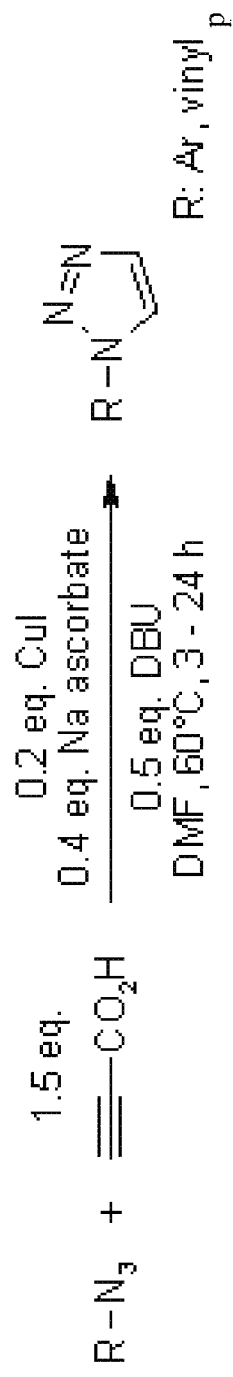
Fig. 45
Fig. 46

RAPID AND EFFICIENT BIOORTHOGONAL LIGATION REACTION AND BORON-CONTAINING HETEROCYCLES USEFUL IN CONJUNCTION THEREWITH

CROSS REFERENCE TO RELATED APPLICATION

The present application is a Division of U.S. patent application Ser. No. 14/694,744, filed Apr. 23, 2015, now U.S. Pat. No. 9,758,533, issued Sep. 12, 2017, which claims benefit of priority from U.S. Provisional Patent Application No. 61/983,396, filed Apr. 23, 2014, the entirety of which are expressly incorporated herein by reference.

STATEMENT OF GOVERNMENT INTEREST

This invention was made with government support under R15 GM-093941 awarded by NIH NIGMS. The government has certain rights in the invention.

BACKGROUND OF THE INVENTION

Each of the references discussed in this specification are expressly incorporated by reference in their entirety, whether or not specifically mentioned in association therewith.

"Click chemistry" is a technology first developed by Sharpless at Scripps Institute, employing a copper (I) catalyzed reaction in which azide moieties are attached via a 1,3-cycloaddition with an alkyne. Copper-free click chemistry reactions are also possible. Methods of using click chemistry are known in the art and include those described by V. V. Rostovtsev, L. G. Green, V. V. Fokin and K. B. Sharpless, Angew. Chem., Int. Ed., 2002, 41, 2596-2599; Sun, Xue-Long, et al. "Carbohydrate and protein immobilization onto solid surfaces by sequential diels-alder and azide-alkyne cycloadditions." Bioconjugate chemistry 17.1 (2006): 52-57; and Baskin, Jeremy M., et al. "Copper-free click chemistry for dynamic in vivo imaging." Proceedings of the National Academy of Sciences 104.43 (2007): 16793-16797. Unfortunately, the mandatory copper catalyst is toxic to both bacterial and mammalian cells, thus precluding applications wherein the cells must remain viable. Catalyst-free Huisgen cycloadditions of alkynes activated by electron-withdrawing substituents have been reported to occur at ambient temperatures. However, these compounds undergo Michael reaction with biological nucleophiles.

"Click Chemistry" reactions are high yielding, wide in scope, create only byproducts that can be removed without chromatography, simple to perform, and can be conducted in easily removable or benign solvents. This concept was developed in parallel with the interest within the pharmaceutical, materials, and other industries in capabilities for generating large libraries of compounds for screening in discovery research. Several types of reaction have been identified that fulfill these criteria, thermodynamically-favored reactions that lead specifically to one product, such as nucleophilic ring opening reactions of epoxides and aziridines, non-aldol type carbonyl reactions, such as formation of hydrazones and heterocycles, additions to carbon-carbon multiple bonds, such as oxidative formation of epoxides and Michael Additions, and cycloaddition reactions.

The azide-alkyne cycloaddition fulfills many of the prerequisites. Many of the starting monosubstituted alkynes and organic azides are available commercially, many others can easily be synthesized with a wide range of functional groups, and their cycloaddition reaction selectively gives 1,2,3-triazoles. See FIG. 45.

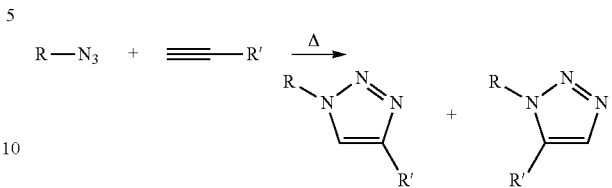

Unfortunately, the thermal Huisgen 1,3-Dipolar Cycloaddition of alkynes to azides requires elevated temperatures and often produces mixtures of the two regioisomers when using asymmetric alkynes. In this respect, the classic 1,3-dipolar cycloaddition fails as a true "click" reaction. A copper-catalyzed variant that follows a different mechanism can be conducted under aqueous conditions, even at room temperature. Additionally, whereas the classic Huisgen 1,3-dipolar cycloaddition often gives mixtures of regioisomers, the copper-catalyzed reaction allows the synthesis of the 1,4-disubstituted regioisomers specifically. By contrast, a later developed ruthenium-catalyzed reaction gives the opposite regioselectivity with the formation of 1,5-disubstituted triazoles. Thus, these catalyzed reactions comply with the definition of click chemistry and have put a focus on azide-alkyne cycloaddition as a prototype click reaction. See FIG. 46.

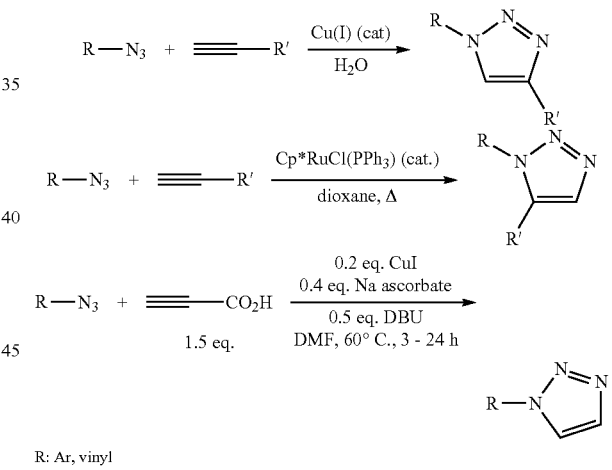

R: Ar, vinyl

The click chemistry reactions are reactions between two functional groups that are highly selective, easy to perform and proceed at nearly quantitative yield. A biocompatible click reaction must have these characteristics but in addition such reactions need to proceed in dilute aqueous solution at neutral pH, and preferably with rapid kinetics. A bioorthogonal click reaction possesses all the characteristics of a biocompatible reaction with the additional requirement that the reactive functional groups do not form stable covalent bonds with functionalities in the biological system.

One of the first types of reaction that was used for bioorthogonal ligations is the reaction of aldehydes and ketones with heteroatom-bonded amines that are sometimes called "α-effect amines" (hydrazine, hydrazide, and other amine-nitrogen compounds, aminooxy reagents, etc.). While an amine-aldehyde/ketone reaction is highly reversible in aqueous solution, an α-effect amine-aldehyde/ketone reaction proceeds readily in mildly acidic aqueous solution to form a product (hydrazone or oxime) that is considerably more stable and less reversible than the product formed with a simple amine. The characteristics of the reaction are sharply dependent on the precise nature of α-effect amine and the carbonyl-containing reactive partner. Such reactions have been well studied. (Jencks, W. P. "Practical kinetics." Catalysis in chemistry and enzymology. McGraw-Hill series in advanced chemistry (1969): 555-614.)

The alpha effect refers to the increased nucleophilicity of a molecule due to the presence of an adjacent (alpha) atom with lone pair electrons. These include hydrazine, hydroxylamine, the hypochlorite ion and the hydroperoxide anion. (Buncel, E., and Um, I.-H. The α-effect and its modulation by solvent, *Tetrahedron* 60, 7801-7825 (2004).)

A major drawback to the use of aldehyde-ketone condensation reactions with α-effect amines is that the optimal pH of the reaction is normally 2-5, which is much lower than physiological pH. (Smith, P. A. S. *Derivatives of Hydrazine and Other Hydronitrogens Having N-N Bonds*, The Benjamin/Cummings Publishing Company, London (1982)). Attempts to speed up the reactions at neutral pH include addition of an aromatic amine as a catalyst. Other efforts have focused on changing the structure of the nucleophile (hydrazine) or the substituents on an aromatic aldehyde, including adding an intramolecular proton source for catalysis. (Dirksen, A., Hackeng, T. M., and Dawson, P. E. Nucleophilic catalysis of oxime ligation, *Angewandte Chemie-International Edition* 45, 7581-7584 (2006); Kool, E. T., Crisalli, P., and Chan, K. M. Fast Alpha Nucleophiles: Structures that Undergo Rapid Hydrazone/Oxime Formation at Neutral pH, *Org. Lett.* 16, 1454-1457 (2014).)

Another drawback of aldehyde-ketone condensation reactions with α-effect amines is the product may not be sufficiently stable under physiological conditions. (Agarwal, P., van der Weijden, J., Sletten, E. M., Rabuka, D., and Bertozzi, C. R. A Pictet-Spengler ligation for protein chemical modification, *Proc. Natl. Acad. Sci. USA* 110, 46-51 (2013)). However, the vast majority of examples use the hydrazone and oxime-forming reactions mentioned previously because of their bioorthogonality, operational simplicity (i.e., no auxiliary reagents are required), and good yields under mild aqueous conditions. However, the resulting C=N bonds are susceptible to hydrolysis (Mueller B M, Wrasidlo W A, Reisfeld R A. Antibody conjugates with morpholinodoxorubicin and acid-cleavable linkers. Bioconjug Chem., 1(5):325-330 (1990)), undermining the use of such conjugates in situations in which long-term stability is required. The oxime has been identified as the most hydrolytically stable C=N linkage, but it is still thermodynamically unstable to hydrolysis under dilute conditions, decomposing via an acid-catalyzed process (Kalia J, Raines R T. Hydrolytic stability of hydrazones and oximes. Angew Chem Int Ed Engl., 47(39):7523-7526 (2008)). Many researchers have found that oxime conjugates that are kept under ideal storage conditions—low temperature, high concentration, and neutral or high pH—are kinetically stable and are therefore suitable for short-term laboratory studies (Hudak, Jason E., Helen H. Yu, and Carolyn R. Bertozzi. "Protein glycoengineering enabled by the versatile synthesis of aminooxy glycans and the genetically encoded aldehyde tag." Journal of the American Chemical Society 133.40 (2011): 16127-16135; Shi X, et al. Quantitative fluorescence labeling of aldehyde-tagged proteins for single-molecule imaging. Nat Methods, 9(5):499-503 (2012); Yi L, et al. A highly efficient strategy for modification of proteins at the C terminus. Angew Chem Int Ed Engl, 49(49):9417-9421 (2010)). However, biological applications requiring extended persistence of the conjugate at physiological temperatures and low concentrations necessitate a significantly more stable covalent linkage than the oxime provides.

Bioorthogonal reactions are chemical reactions that can be used in biological systems, coupling one reactive group specifically with another reactive group: without side reactions; in neutral, aqueous solution; and under additional conditions that are compatible with the biological system. Bioorthogonal reactions can be used for conjugating a biomolecule and a reporter; in biotechnology; proteomics; (bio)polymer engineering; sensors and detectors; and drug delivery. See Drahl, Carmen, "Unnaturally Productive", C&E News Vol. 89(34):40-42, cen.acs.org/articles/89/i34/Unnaturally-Productive.html; Lahann, J., (Ed.) *Click Chemistry for Biotechnology and Materials Science*, John Wiley & Sons Ltd, West Sussex, U K (2009); Manchester, M., and N. F. Steinmetz. "Viral nanoparticles: tools for materials science & biomedicine." (2010).

The ideal bioconjugation chemistry has, for example, the following characteristics, some of which are optional or context dependent (adapted from Solulink, Inc. White paper on Bioconjugation Chemistry):

a) linkers must be incorporated on biomolecules in a mild, controllable manner b) the inherent biological function of the biomolecules must be unaffected after modification and conjugation c) the conjugation reaction occurs directly upon mixing the two modified biomolecules, preferably not requiring addition of an oxidant, reductant, or metal.

d) modified biomolecules are stable over extended periods e) conjugation occurs in buffered aqueous solutions, at a physiological pH f) stoichiometrically efficient (e.g., 1:1)

g) fast reaction kinetics h) no undesirable covalent side reactions during modification i) linkers can be incorporated on a variety of biomolecules, including oligonucleotides and peptides.

The concept of bioorthogonality means that the technology does not interfere with biological processes in the same medium (unless specifically targeted), and the technology is not interfered with by components of the biological medium. Bioorthogonal processes therefore occur in aqueous medium, without addition of toxic substances (or toxic concentrations of substances), within a physiological pH range (e.g., ~6-8), at physiological temperatures (e.g., 0-42° C., depending on species) and pressures (e.g., 1 Atm), are not interactive with physiological thiols or amines, or are sensitive to redox chemistry. Further, the biological environment typically contains a range of enzymes that can degrade certain structures, and therefore bioorthogonal reaction reagents or products should not be sensitive to modification by the various enzymes in the medium. See, Bertozzi: Chem Soc Review, 2010; US 2011/0207147.

Click chemistry reactions have applications beyond biological systems, including materials chemistry. (Iha, R. K., Wooley, K. L., Nystrom, A. M., Burke, D. J., Kade, M. J., and Hawker, C. J. Applications of Orthogonal "Click" Chemistries in the Synthesis of Functional Soft Materials, *Chemical Reviews* 109, 5620-5686 (2009); Oommen, O. P., Wang, S., Kisiel, M., Sloff, M., Hilborn, J., and Varghese, O. P. Smart Design of Stable Extracellular Matrix Mimetic Hydrogel: Synthesis, Characterization, and In Vitro and In Vivo Evaluation for Tissue Engineering, *Advanced Functional Materials* 23, 1273-1280 (2013)).

See also,

Achilli, C., Ciana, A., Fagnoni, M., Balduini, C., and Minetti, G. Susceptibility to hydrolysis of phenylboronic pinacol esters at physiological pH, Cent. *Eur. J. Chem.* 11, 137-139 (2013);

Agarwal, P., van der Weijden, J., Sletten, E. M., Rabuka, D., and Bertozzi, C. R. A Pictet-Spengler ligation for protein chemical modification, *Proc. Natl. Acad. Sci. USA* 110, 46-51 (2013); Axup, J. Y., Bajjuri, K. M., Ritland, M., Hutchins, B. M., Kim, C. H., Kazane, S. A., Halder, R., Forsyth, J. S., Santidrian, A. F., Stafin, K., Lu, Y., Tran, H., Seller, A. J., Biroc, S. L., Szydlik, A., Pinkstaff, J. K., Tian, F., Sinha, S. C., Felding-Habermann, B., Smider, V. V., and Schultz, P. G. Synthesis of site-specific antibody-drug conjugates using unnatural amino acids, *Proc. Natl. Acad. Sci. USA* 109, 16101-16106 (2012).

Buncel, E., and Um, I.-H. The α-effect and its modulation by solvent, *Tetrahedron* 60, 7801-7825 (2004);

Cano, W. G., Solares, G. R., DiPetrillo, T. A., Meylaerts, S. A. G., Lin, S. C., Zamenhof, R. G., Saris, S. C., Duker, J. S., Goad, E. Toxicity associated with boronophenylalanine and cranial neutron irradiation, *Radiat. Oncol. Invest.* 3, 108-118 (1995);

Chen, Yong-Xiang, Gemma Triola, and Herbert Waldmann. "Bioorthogonal chemistry for site-specific labeling and surface immobilization of proteins." Accounts of chemical research 44.9 (2011): 762-773;

Ciaravino, V., Plattner, J., and Chanda, S. An assessment of the genetic toxicology of novel boron-containing therapeutic agents, *Environ. Mol. Mutag.* 54, 338-346 (2013);

Dewar, M. J. S., and Dougherty, R. C. Boron-containing analogs of isoquinoline, *J. Am. Chem. Soc.* 84, 2648-2649 (1962);

Dewar, M. J. S., and Dougherty, R. C. New heteroaromatic compounds. XX. Derivatives of 4,3-borazaroisoquinoline, *J. Am. Chem. Soc.* 86, 433-436 (1964);

Dirksen, A., Hackeng, T. M., and Dawson, P. E. Nucleophilic catalysis of oxime ligation, *Angewandte Chemie-International Edition* 45, 7581-7584 (2006);

E Olberg, D., and O. K Hjelstuen. "Labeling strategies of peptides with 18F for positron emission tomography." Current topics in medicinal chemistry 10.16 (2010): 1669-1679. ("The field of 18F-fluorine chemistry applied on peptides is expanding. A variety of recently employed labeling strategies like acylation, alkylation, thiol reactive, oxime formers, 1,3-dipolar cycloadditions have been summarized in this review. Higher yields, milder reaction conditions and simplification for automation are important drivers for the ongoing development. The simultaneous elevation in understanding of 18F labeling mechanisms makes hopes for the clinical usefulness of radiolabeled peptides for human diagnostic medicine and therapy monitoring.");

Fukuda, Tomohiro, Shunsuke Onogi, and Yoshiko Miura. "Dendritic sugar-microarrays by click chemistry." Thin Solid Films 518.2 (2009): 880-888;

Gronowitz, S., and Namtvedt, J. Heteroaromatic boron compounds. II. Synthesis, nuclear magnetic resonance-spectra, and hydrolytic stability of some borazarothienopyridines, *Acta Chem. Scand.* 21, 2151-2166 (1967);

Groziak, M. P., Chen, L., Yi, L., and Robinson, P. D. Planar Boron Heterocycles with Nucleic Acid-Like Hydrogen-Bonding Motifs, *J. Am. Chem. Soc.* 119, 7817-7826 (1997);

Iha, R. K., Wooley, K. L., Nystrom, A. M., Burke, D. J., Kade, M. J., and Hawker, C. J. Applications of Orthogonal "Click" Chemistries in the Synthesis of Functional Soft Materials, *Chemical Reviews* 109, 5620-5686 (2009);

Iha, Rhiannon K., et al. "Applications of orthogonal "click" chemistries in the synthesis of functional soft materials." *Chemical reviews* 109.11 (2009): 5620-5686.;

Jencks, W. P. "Practical kinetics." Catalysis in chemistry and enzymology. McGraw-Hill series in advanced chemistry (1969): 555-614, McGraw-Hill;

Jencks, W. P. Mechanism and catalysis of simple carbonyl group reactions, *Progr. Phys. Org. Chem.* (Saul G. Cohen, Andrew Streitwieser, Jr., and Robert W. Taft, editors. Interscience) 2, 63-128 (1964);

Jencks, W. P. Mechanism of oxime and semicarbazone formation, *J. Am. Chem. Soc.* 81, 475-481 (1959);

Kool, E. T., Crisalli, P., and Chan, K. M. Fast Alpha Nucleophiles: Structures that Undergo Rapid Hydrazone/Oxime Formation at Neutral pH, *Org. Lett.* 16, 1454-1457 (2014);

Koudelka, Kristopher J., and Marianne Manchester. "Chemically modified viruses: principles and applications." Current Opinion In Chemical Biology 14.6 (2010): 810-817. ("Viral nanotechnology is a highly interdisciplinary field, incorporating virology, chemistry, physics, physiology, pharmacology, and materials science [1]. Methods have been established for the efficient production and chemical modification of viral nanoparticles (VNPs), as well as non-infectious virus-like particles (VLPs) that mimic the structure of infectious particles but lack nucleic acid. These methods provide the foundation for fine-tuning of ligand or probe attachment, immobilization of VNPs on surfaces, or assembly into complex aggregate or network structures . . . . The ability to precisely place components on the surface of viruses, by chemical or genetic means, has allowed for the creation of complex systems that impart novel function.");

Lahann, J., (Ed.) (2009) *Click Chemistry for Biotechnology and Materials Science*, John Wiley & Sons Ltd, West Sussex, UK. (From Preface: "While the concept of click chemistry might have initially been introduced with a firm eye on drug discovery, its applications to materials synthesis and biotechnology have been a startling success story. Thus, as I look ahead toward the advances coming from click chemistry in the next decade, some of the most promising applications are related to materials science and biotechnology. With this book, it is my intention to share some of the excitement surrounding click chemistry by describing the most recent progress with respect to (i) the development of a conceptual framework of click chemistry, (ii) its application to the precise design and synthesis of macromolecules, and (iii) its numerous applications in materials science and biotechnology.");

LaHann, T. R., Bauer, W. F., Gavin, P., and Lu, D. R. Pharmacokinetics and toxicity of a p-boronophenylalanine-cyclodextrin formulation delivered by intravenous infusion to dogs, *ACS Symp. Ser.* 545, 66-78 (1994);

LaHann, T. R., Sills, C., Hematillake, G., Dymock, T., and Daniell, G. Cardiovascular toxicities associated with intravenous administration of p-boronophenylalanine formulations, pp 513-517, Plenum (1993);

Li, Chao-Jun, and Liang Chen. "Organic chemistry in water." Chemical Society Reviews 35.1 (2006): 68-82. ("Dehydration is a very common reaction in organic chemistry. It is difficult to carry out in water because water molecules generated during the reaction must be removed to shift equilibrium toward the side of the dehydrated product.")("Aqueous organic chemistry is essential for the emerging field of chemical biology, which uses chemical tools to study biology. Since life constructs chemical bonds in aqueous environments, selective chemical reactions designed to modify biomolecules are now recognized as powerful tools in chemical biology. They provide insight into cellular processes and inspire new strategies for protein engineering. To achieve this goal, the participating functional groups must have a narrow distribution of reactivity and must be inert toward biological molecules. In addition, the selective chemical reactions must occur at room temperature and in aqueous physiological environments.");

Lim, Reyna K V, and Qing Lin. "Bioorthogonal chemistry: recent progress and future directions." Chemical Communications 46.10 (2010): 1589-1600;

Liu, C. C., and Schultz, P. G. Adding New Chemistries to the Genetic Code, In *Annual Review of Biochemistry, Vol 79* (Kornberg, R. D., Raetz, C. R. H., Rothman, J. E., and Thorner, J. W., Eds.), pp 413-444 (2010); and Manabe, Kei, et al. "Dehydration Reactions In Water. Brønsted Acid—Surfactant-Combined Catalyst For Ester, Ether, Thioether, And Dithioacetal Formation In Water." Journal of the American Chemical Society 124.40 (2002): 11971-11978. ("Although various efficient catalytic systems in water have been developed so far, there are still many types of reactions which are difficult to carry out in water. One such reaction is dehydration in which water molecules generated during the reaction must be removed to shift equilibrium to the dehydrated product side. A representative example is acid-catalyzed direct esterification of carboxylic acids with alcohols. Generally, direct esterification is carried out in organic solvents and requires either of two methods to shift the equilibrium to afford the product (ester) in good yields: continuous removal of water during the reaction (azeotropically or using dehydrating agents) and use of a large excess of one of the reactants. In any case, the presence of large excess amounts of water as a solvent should have a detrimental effect on the equilibrium of the dehydration reaction.");

Mehlich, Jan, and Bart Jan Ravoo. "Click chemistry by microcontact printing on self-assembled monolayers: A structure-reactivity study by fluorescence microscopy." Organic & Biomolecular Chemistry 9.11 (2011): 4108-4115. ("The modification of inorganic surfaces with monolayers of organic molecules has found widespread application in nanofabrication, sensing, diagnostics and molecular electronics. 1-6 The microscale patterning of molecular monolayers is crucial to all of these applications. In recent years, microcontact printing (mCP) has developed into a powerful tool to functionalize substrates with spatially patterned molecular monolayers . . . . Recently, it was shown that also the Huisgen 1,3-dipolar cycloaddition of alkynes and azides can be induced by mCP.17It was demonstrated that the cycloaddition by mCP proceeds to completion (i.e. until all reactive sites on the surface are occupied) within a few hours when a Cu-coated stamp is used or Cu(I) catalyst is added to the alkyne ink.");

Oommen, O. P., Wang, S., Kisiel, M., Sloff, M., Hilborn, J., and Varghese, O. P. Smart Design of Stable Extracellular Matrix Mimetic Hydrogel: Synthesis, Characterization, and In Vitro and In Vivo Evaluation for Tissue Engineering, *Advanced Functional Materials* 23, 1273-1280 (2013);

Prestwich, Glenn D., et al. "Controlled chemical modification of hyaluronic acid: synthesis, applications, and biodegradation of hydrazide derivatives." Journal of Controlled Release 53.1 (1998): 93-103. ("Hyaluronic acid (HA), The immunoneutrality of HA makes it an HA [6-9]. HA ranging in size from six disaccharide excellent building block for biomaterials to be employed for tissue engineering and drug delivery. Controlled modification of the carboxylic acid moieties of hyaluronic acid with mono- and polyfunctional hydrazides leads to biochemical probes, biopolymers with altered physical and chemical properties, tethered drugs for controlled release, and crosslinked hydrogels as biocompatible scaffoldings for tissue engineering. Methods for polyhydrazide synthesis, for prodrug preparation, for hydrogel crosslinking, and for monitoring biodegradation are described.");

Sapra, Puja, and Boris Shor. "Monoclonal antibody-based therapies in cancer: advances and challenges." Pharmacology & therapeutics 138.3 (2013): 452-469. ("Over the last decade of ADC (antibody-Drug Conjugates) development, it has become clear that choice of conjugation strategy and sites on the Ab are highly important in determining the tolerability, pharmacokinetic (PK) properties and overall effectiveness of ADC therapy. Ideally, conjugation of the Ab to the drug should not perturb the integrity of the Ab, the binding of the Ab to the antigen, or the biological activity of the drug.") A method for putting hydrazides on antibodies (Immunoliposomes: Targeted Delivery—Hydrazide Modification) is described. See FIGS. 37 and 38;

Sletten, Ellen M., and Carolyn R. Bertozzi. "Bioorthogonal chemistry: fishing for selectivity in a sea of functionality." Angewandte Chemie International Edition 48.38 (2009): 6974-6998;

Smith, P. A. S. *Derivatives of Hydrazine and Other Hydronitrogens Having N-N Bonds*, The Benjamin/Cummings Publishing Company, London (1982);

Touchet, S., Carreaux, F., Carboni, B., Bouillon, A., & Boucher, J. L. (2011). Aminoboronic acids and esters: from synthetic challenges to the discovery of unique classes of enzyme inhibitors. Chemical Society Reviews, 40(7), 3895-3914.

Tschampel, P., and Snyder, H. R. Arylboronic acids. VII. Some reactions of o-formylbenzeneboronic acid, *J. Org. Chem.* 29, 2168-2172 (1964);

Wangler, C., et al. "Click-chemistry reactions in radiopharmaceutical chemistry: fast & easy introduction of radiolabels into biomolecules for in vivo imaging." Current medicinal chemistry 17.11 (2010): 1092-1116. ("When introducing radioactive nuclides with a very short half-life into biomolecules . . . . Time is always the most important issue . . . . This is the reason why just a part of the reactions that belong in principle to the group of click reactions have shown to meet the requirements for radiosyntheses.")(Lahann, J., (Ed.) (2009);

Yang, W., Gao, X., & Wang, B. (2005). Biological And Medicinal Applications Of Boronic Acids. Boronic Acids: Preparation and Applications in Organic Synthesis and Medicine, 481-512, Edited by Dennis G. Hall Wiley-VCH Verlag GmbH & Co. KGaA, Weinheim (2005) ISBN 3-527-30991-8;

SUMMARY OF THE INVENTION

The present technology provides a bioorthogonal reaction and reagents useful therein, which comprise a boronic acid or ester having an ortho carbonyl or aldehyde on an optionally substituted aryl or aromatic heterocyclic compound, which reacts with an alpha-effect amine under biologically compatible conditions. The result of a reaction is a dehydration reaction, forming a hydrazono or imino arylboronic acid product (A). The product from the dehydration reaction is frequently followed by a second reaction to form a heterocyclic ring that contains a boron atom, e.g., a 3,4-borazaisoquinoline (B) or a related boron-containing heterocycle such as a 1,2-dihydrobenzo[d][1,2,3]diazaborinin-1-uide (C).

The reaction generally approaches the ideal "click chemistry" profile; it occurs without toxic reagents in aqueous solution at neutral pH, with high reaction yields, rapid and spontaneous initiation, and lack of cross reactivity in a physiological environment.

The rate of formation of these products in neutral aqueous solution is considerably greater than the rate of formation of substrates without the boronic acid or ester. Furthermore, the final product is more stable than the corresponding product without the boron atom. See FIG. 1.

FIG. 1 shows the reaction of aromatic boronic acid or ester with α-effect amines. The structure of the final product is a function of the various R groups. Product A may be the final product (especially when X=O) or it may be an intermediate product (especially when X=NH). With many types of substituents, particularly when $R_2$ is alkyl, substituted alkyl, or aryl, molecules with the core structure of Product B will be the final product. The product labeled C is a form of products A or B that may be produced depending on the substituents.

The characteristics of the reaction of ortho-carbonyl phenylboronic acid or ester with an α-effect amine are different from those of the reaction of other aromatic aldehydes and ketones with these reagents. The reaction is very fast at neutral pH, and no catalyst is needed. The observed reaction may be faster with hydrazides than hydrazines. This is the opposite of how an α-effect amine behaves with any other known aldehyde or ketone. Under some reaction conditions, a methyl ketone reacts faster than the corresponding aldehyde. This is the opposite of how these reactions normally behave. (Moscovici, R., et al. "α-Effect Amines and Carbonyls: Mechanism and catalysis for phenylhydrazone formation from aromatic heterocyclic aldehydes." The Journal of Organic Chemistry 41.26 (1976): 4093-4096; Jencks, W. P. Mechanism and catalysis of simple carbonyl group reactions, *Progr. Phys. Org. Chem.* (Saul G. Cohen, Andrew Streitwieser, Jr., and Robert W. Taft, editors. Interscience) 2, 63-128 (1964); Jencks, W. P. Mechanism of oxime and semicarbazone formation, *J. Am. Chem. Soc.* 81, 475-481 (1959)).

Boronic esters may hydrolyze to form boronic acids and alcohols in aqueous solution. (Achilli, C., Ciana, A., Fagnoni, M., Balduini, C., and Minetti, G. Susceptibility to hydrolysis of phenylboronic pinacol esters at physiological pH, *Cent. Eur. J. Chem.* 11, 137-139(2013)). Reaction of these solutions with α-effect amines proceeds. Therefore, other forms of boron can be used in the reaction provided that they undergo hydrolysis to form the boronic acid. (For example, pinacol ester-masked boronic acids.) Thus, while the reaction typically involves boronic acids having an ortho carbonyl, the reagent added to the medium may be a precursor of this structure, such as a boronic acid ester or blocked boronate, and an ortho enol or enamine. The boronic acid and carbonyl are typically ortho substituted on an aromatic ring, but may be part of other structures, such as heterocycles or non-aryl compositions.

3,4-Borazaisoquinolines and related heterocycles were originally prepared to study "non-benzenoid" aromaticity (Dewar, M. J. S., and Dougherty, R. C. Boron-containing analogs of isoquinoline, *J. Am. Chem. Soc.* 84, 2648-2649 (1962); Gronowitz, S., and Namtvedt, J. Heteroaromatic boron compounds. II. Synthesis, nuclear magnetic resonance-spectra, and hydrolytic stability of some borazarothienopyridines, *Acta Chem. Scand.* 21, 2151-2166 (1967)).

The methods by which they were synthesized are typical for synthetic organic chemistry. High concentrations of components, which are in virtually all examples heated in an organic solvent such as ethanol, often containing acid catalysts. The few examples of reactions that were performed in aqueous solution were normally highly concentrated, exposed to acidic pH (pH 6) and/or were boiled or subjected to a long reaction time. (Tschampel, P., and Snyder, H. R. Arylboronic acids. VII. Some reactions of o-formylbenzeneboronic acid, *J. Org. Chem.* 29, 2168-2172 (1964); Dewar, M. J. S., and Dougherty, R. C. New heteroaromatic compounds. XX. Derivatives of 4,3-borazaroisoquinoline, *J. Am. Chem. Soc.* 86, 433-43 (1964); Groziak, M. P., Chen, L., Yi, L., and Robinson, P. D. Planar Boron Heterocycles with Nucleic Acid-Like Hydrogen-Bonding Motifs, *J. Am. Chem. Soc.* 119, 7817-7826 (1997)).

The reaction of ortho-carbonyl phenylboronic acid or ester with an α-effect amine is a known reaction; however, it has not previously been applied to coupling under physiological conditions, i.e., aqueous solvent, physiologically compatible temperature, pH, lack of reagents at toxic concentrations, etc.

The present technology comprises coupling two molecules to react with quantitative yields under physiological conditions and without harsh conditions or organic solvents, with the possibility of further rearranging to form a boron-containing heterocycle or related product.

Many biomolecules are stable in a limited pH range (near neutral pH), temperature (0-37 degrees centigrade, or higher in some organisms, e.g., 40, 43, 45, 50, or 55° C., and lower, especially in organisms having antifreeze properties, e.g., −5° C.) and environment (aqueous). Coupling reactions that can be performed under conditions that preserve the structure and activity of the biomolecule have many potential applications. The pH range is preferably 2-9, more preferably 6-8, and most preferably 6.5 to 7.5. The reaction preferably proceeds to essential completion within 10 minutes under the biocompatible conditions.

The product of the reaction may be stable at neutral pH for many months. Stability of the product at various pHs depends on the substitution pattern. This property may be useful for pH-dependent reversal of the coupling reaction.

Preliminary cytotoxicity studies do not reveal toxicity, and there is reason to believe that it will not be very toxic to mammals. For example, boronic acids are generally non-toxic. (Ciaravino, V., Plattner, J., and Chanda, S. An assessment of the genetic toxicology of novel boron-containing therapeutic agents, *Environ. Mol. Mutag.* 54, 338-346 (2013)). They are not metabolized in humans. Sulfonyl-substituted 3,4-borazaisoquinolines that have been tested for antimicrobial activity are generally not cytotoxic (Future Science 1 1275-1288, 2009).

There are a number of reported in vivo (including human) studies of p-borophenylalanine (LaHann, T. R., et al. "Cardiovascular toxicities associated with intravenous administration of p-boronophenylalanine formulations." Advances in neutron capture therapy. Springer US, 1993. 513-517., Plenum; LaHann, T. R., Bauer, W. F., Gavin, P., and Lu, D. R. Pharmacokinetics and toxicity of a p-boronophenylalanine-cyclodextrin formulation delivered by intravenous infusion to dogs, *ACS Symp. Ser.* 545, 66-78 (1994)). The ortho carbonyl (e.g., aldehyde, ketone) derivatives of p-boronophenylalanine are believed to be useful to provide selective coupling to peptides in which the p-boronophenylalanine derivative substitutes for a naturally occurring amino acid. See FIG. 2.

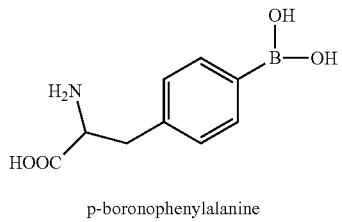 [SMILES: NC(Cc1ccc(B(O)O)cc1)C(=O)O]

p-boronophenylalanine

It is therefore an object to provide a process for preparing a hydrazono or imino arylboronic acid, 3,4-borazaisoquinoline or a 1,2-dihydrobenzo[d][1,2,3]diazaborinin-1-uide comprising: contacting a carbonyl-substituted arylboronic acid with an α-effect amine in an aqueous medium for a time sufficient to form the product. The reaction is preferably carried out at ambient temperature, and/or at neutral pH. Equimolar amounts of the carbonyl-substituted arylboronic acid and the α-effect amine may be contacted, and the reaction between these components preferably proceeds essentially to completion, with minimal or no side reactions.

The carbonyl substituted arylboronic acid may comprise an ortho formyl phenylboronic acid derivative; or an ortho ketone phenylboronic acid derivative.

The carbonyl substituted arylboronic acid may comprise an ortho formyl phenylboronic acid derivative of an amino acid or an ortho formyl phenylboronic acid derivatized with an orthogonal reactive functional group.

The α-effect amine may comprise a hydrazine, a semicarbazide, a thiosemicarbazide, a hydrazide, a thiohydrazide, a hydroxylamine, an O-alkylhydroxylamine or an O-arylhydroxylamine.

In some cases, reactions between competing boronic acid esters and/or α-amines may be provided, wherein the ratio of product serves, e.g., as an indicator of process. Likewise, one or more fluorescent reporters or fluorescence quenching molecules may be linked to the boronic acid ester, and/or α-effect amine.

The aqueous medium preferably has a pH between 2 and 9, more preferably between 6 and 8, and most preferably between 7.0 and 7.5. The aqueous medium may have a pH of about 7.

The time is preferably less than about 10 minutes at a temperature, between about 0 C and 37 C, and for example proceeds essentially to completion e.g., >90% yield, within 5 minutes at 25-37 C.

The hydrazono or imino arylboronic acid, 3,4-borazaisoquinoline or a 1,2-dihydrobenzo[d][1,2,3]diazaborinin-1-uide derivative, carbonyl-substituted arylboronic acid, α-effect amine, and aqueous medium are preferably each bioorthogonal.

It is another object to provide a reaction method comprising combining a carbonyl-substituted arylboronic acid and an α-effect amine in aqueous solution at a temperature between about −5 C to 55 C, and a pH between 2 and 8 to produce an adduct A, which may then proceed to form B or C, see FIG. 1:

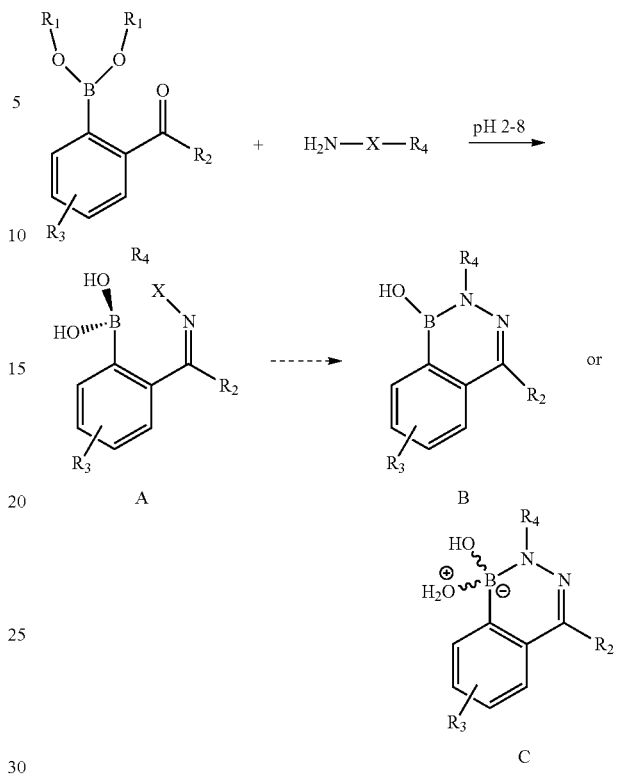

$R_1$ may be H or pinacol, or more generally any boronic acid or ester forming compound which readily hydrolyses in aqueous solvent under physiological conditions, e.g., $C_1$-$C_6$ alkyl which optionally may incorporate one further heteroatom selected from nitrogen, oxygen and sulfur, formyl or $C_2$-$C_6$ alkanoyl, $OCH_2Ar$ or $OCH_2CH_3Ar$ in which the Ar group may be a phenyl, a substituted phenyl ring, a naphtyl, a heteroaromatic ring, or fused ring comprising at least one ring heteroatom selected from nitrogen, oxygen and sulfur.

$R_2$ may be H or $CH_3$, or more generally $C_1$-$C_6$ alkyl, aryl, heteroaryl, which optionally may incorporate one further heteroatom selected from nitrogen, oxygen and sulfur, $C_2$-$C_6$ alkanoyl, $CH_2Ar$ or $CH_2CH_2Ar$ in which the Ar group may be a phenyl, a substituted phenyl ring, a naphtyl, a heteroaromatic ring, or fused ring comprising at least one ring heteroatom selected from nitrogen, oxygen and sulfur, a 4 to 7 member ring optionally incorporating one or more heteroatoms selected from oxygen, nitrogen, or sulfur, an aromatic ring optionally substituted with fluorescent groups, sugars and polyethylene glycol chains.

$R_3$ may be selected from one or more of the group consisting of OH, O-alkyl, O-alkylamine, O-alkylthiol, O-alkylthioester, alkylamine, alkylbromide or F, and $C_1$-$C_6$ alkyl, aryl, heteroaryl, which optionally may incorporate one further heteroatom selected from nitrogen, oxygen and sulfur, $C_2$-$C_6$ alkanoyl, $CH_2Ar$ or $CH_2CH_2Ar$ in which the Ar group may be a phenyl, a substituted phenyl ring, a naphtyl, a heteroaromatic ring, or fused ring comprising at least one ring heteroatom selected from nitrogen, oxygen and sulfur, a 4 to 7 member ring optionally incorporating one or more heteroatoms selected from oxygen, nitrogen, or sulfur, an aromatic ring optionally substituted with fluorescent groups, sugars and polyethylene glycol chains, and may be the same or different.

$R_4$ may be selected from one or more of the group consisting of H, $CH_3$, $CH_2CH_3$, $CH_2Ph$, p-COOH Ph, o-NH$_2$Ph, o-OH Ph, COH, COCH$_3$, COCH$_2$Ph, COPh, CO-coumarin, or CONH$_2$, and may be the same or different.

It is a further object to provide a composition, comprising at least one of (see FIGS. 39A-39D):

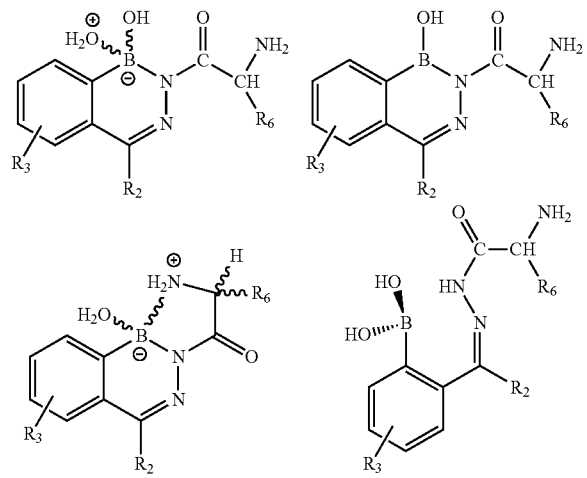

wherein R$_2$ is H or CH$_3$, R$_3$ is alkyl or OR (which may be, e.g., alkyl, alkylamine, alkylthiol, alkylbromide aryl, heteroaryl, which optionally may incorporate one further heteroatom selected from nitrogen, oxygen and sulfur, C$_2$-C$_6$ alkanoyl, CH$_2$Ar or CH$_2$CH$_2$Ar in which the Ar group may be a phenyl, a substituted phenyl ring, a naphtyl, a heteroaromatic ring, or fused ring comprising at least one ring heteroatom selected from nitrogen, oxygen and sulfur, a 4 to 7 member ring optionally incorporating one or more heteroatoms selected from oxygen, nitrogen, or sulfur, an aromatic ring optionally substituted with fluorescent groups, sugars and polyethylene glycol chains); and R$_5$ is H, CH$_3$, CH$_2$CH$_3$, CH$_2$Ph, Ph, substituted Ph, NH$_2$, for example.

The alpha carbon of the carbonyl may be bonded to an amine (see FIGS. 40A-40C):

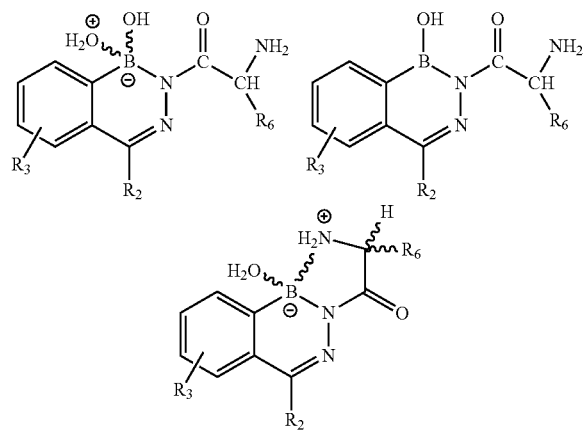

R$_5$ may comprise an aryl group having an ortho nucleophile, 2-hydroxy phenyl, 2-amino phenyl, or a nucleophilic substituent that cyclizes with the boron atom.

It is another object to provide a composition as follows (see FIG. 35A-35B):

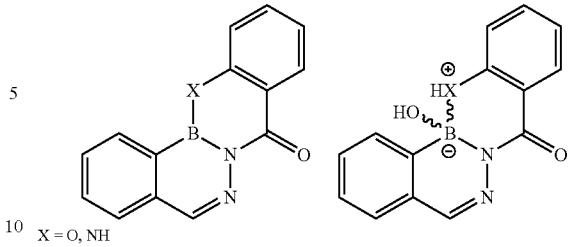

X = O, NH

A further object provides a process comprising, contacting a first composition having a boron atom bonded to a sp$^2$ hybridized carbon, the boron having at least one labile substituent, conjugated with a cis-carbonyl, with a second composition having an α-effect amine, in an aqueous medium for a time sufficient to form an adduct, which may proceed to further products, such as by dehydration, interaction as a Lewis base with the solvent (e.g., water) or a heteroatom (e.g., amine). See FIG. 41

The reaction may proceed as follows:

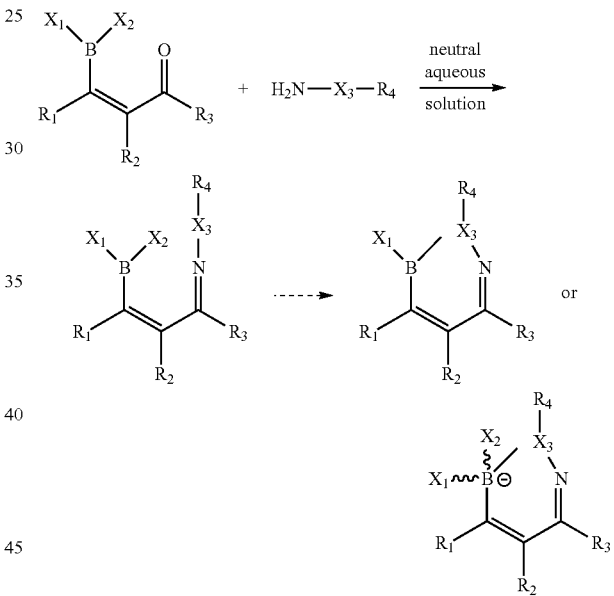

wherein:

X$_1$ and X$_2$ represents independently selected groups that can hydrolyze to boronic acid (OHs): e.g., OH, F, C$_1$-C$_6$ alkyl which optionally may incorporate one further heteroatom selected from nitrogen, oxygen and sulfur, formyl or C$_2$-C$_6$ alkanoyl, OCH$_2$Ar or OCH$_2$CH$_2$Ar in which the Ar group may be a phenyl, a substituted phenyl ring, a naphtyl, a heteroaromatic ring, or fused ring comprising at least one ring heteroatom selected from nitrogen, oxygen and sulfur; or the group X$_1$ and X$_2$ together represents a 5 to 7 member ring optionally incorporating one or more heteroatoms selected from oxygen, nitrogen, or sulfur.

R$_1$ and R$_2$ independently represent H, CH$_3$, C$_1$-C$_6$ alkyl which optionally may incorporate one further heteroatom selected from nitrogen, oxygen and sulfur, C$_2$-C$_6$ alkanoyl, CH$_2$Ar or CH$_2$CH$_2$Ar in which the Ar group may be a phenyl, a substituted phenyl ring, a naphtyl, a heteroaromatic ring, or fused ring comprising at least one ring heteroatom selected from nitrogen, oxygen and sulfur; or the group $R_1$—C=C—$R_2$ together represents a 5 to 7 member ring optionally incorporating one or more heteroatoms selected from oxygen, nitrogen, or sulfur, an aromatic ring optionally substituted with fluorescent groups, sugars and polyethylene glycol chains.

$R_3$ represents $CH_3$, $C_1$-$C_6$ alkyl which optionally may incorporate one further heteroatom selected from nitrogen, oxygen and sulfur, $C_2$-$C_6$ alkanoyl, $CH_2Ar$ or $CH_2CH_2Ar$ in which the Ar group may be a phenyl, a substituted phenyl ring, a naphtyl, a heteroaromatic ring, or fused ring comprising at least one ring heteroatom selected from nitrogen, oxygen and sulfur, a 4 to 7 member ring optionally incorporating one or more heteroatoms selected from oxygen, nitrogen, or sulfur, an aromatic ring optionally substituted with fluorescent groups, sugars and polyethylene glycol chains.

$X_3$ may be O or N.

$X_4$ may be OH, $H_2O$, alkyl, aryl, or other heteroatom containing group (usually solvent).

See, WO 2013/084198, expressly incorporated herein by reference.

The aqueous medium preferably has a neutral pH, e.g., pH 6.8-7.5, but the reaction may occur in a solution having a pH of, e.g., between 2 and 8.

The process is preferably performed at a temperature between 0 C and 45° C., e.g., 25 C-37° C., though the range may extend to, e.g., −5 to 55° C.

The reactants and range of reaction conditions are preferably bioorthogonal, i.e., compatible with living cells.

The composition may comprise a carbonyl-substituted arylboronic acid or ester.

The composition may be selected from the group consisting of:

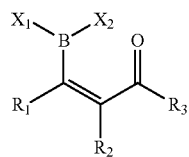

wherein:

$X_1$, $X_2$ are groups that can hydrolyze from the boron to yield boronic acid; and $R_1$, $R_2$, and $R_3$ are hydrogen, organic ligands, or heterorganic ligands.

$R_2$ may be selected from the group consisting of: H, $CH_3$; and $R_3$ may be selected from the group consisting of OH, O-alkyl, O-alkylbromide, O-alkylamine, O-alkylamide, O-alkylthiol, O-alkylthioester, alkylamine, alkylamide and alkylbromide.

The α-effect amine may be selected from the group consisting of: $H_2N$—$X_3R_4$, wherein: $X_3$ is O or N; and $R_4$ is an alkyl, aryl or a heteroatom containing group.

$R_4$ may be selected from the group consisting of: H, $CH_3$, $CH_2CH_3$, $CH_2Ph$, p-COOH Ph, o-$NH_2$Ph, o-OH Ph, COH, $COCH_3$, $COCH_2Ph$, COPh, CO-coumarin, and $CONH_2$.

The α-effect amine may be selected from the group consisting of alpha-hydrazides of tyrosine, phenylalanine, alanine, beta-alanine, glycine, dimethylglycine, and CBz-serine.

The α-effect amine may also be selected from the group consisting of: a hydrazine; a semicarbazide, a thiosemicarbazide; a hydrazide, a thiohydrazide, a hydroxylamine, an O-alkylhydroxylamine, and an O-arylhydroxylamine.

The adduct may comprise a composition selected from the group consisting of:

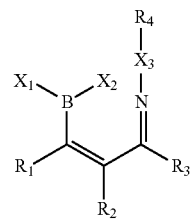

and a further product thereof formed through at least one of dehydration, interaction with the solvent, and interaction with a reactive heteroatom in the solvent.

The further product may comprises, for example, a dehydration product selected from the group consisting of:

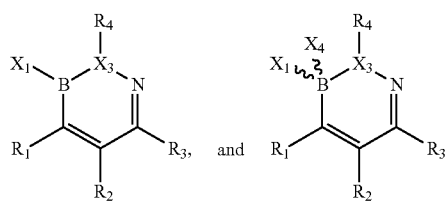

wherein $R_4$ is selected from the group consisting of alkyl, aryl, heteroalkyl, heteroaryl, and hydroxyl, and $X_4$ is selected from the group consisting of alkyl, aryl, heteroalkyl, heteroaryl, hydroxyl and water ($H_2O$).

The adduct may be selected from the group consisting of a hydrazono or imino arylboronic acid, 3,4-borazaisoquinoline and a 1,2-dihydrobenzo[d][1,2,3]diazaborinin-1-uide.

The adduct composition product may be selected from the group consisting of:

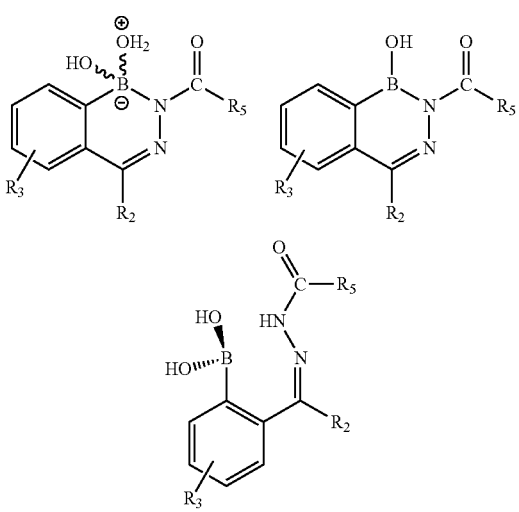

wherein:

$R_2$ is selected from the group consisting of H and $CH_3$;

$R_3$ is selected from the group consisting of alkyl, OH, O-alkyl, O-alkylbromide, O-alkylamine, O-alkylamide, O-alkylthiol, O-alkylthioester, alkylamine, alkylamide and alkylbromide; and $R_5$ is selected from the group consisting of H, —$CH_3$, —$CH_2CH_3$, —$CH_2Ph$, Ph, substituted Ph, and —$NH_2$.

The adduct may also be selected from the group consisting of:

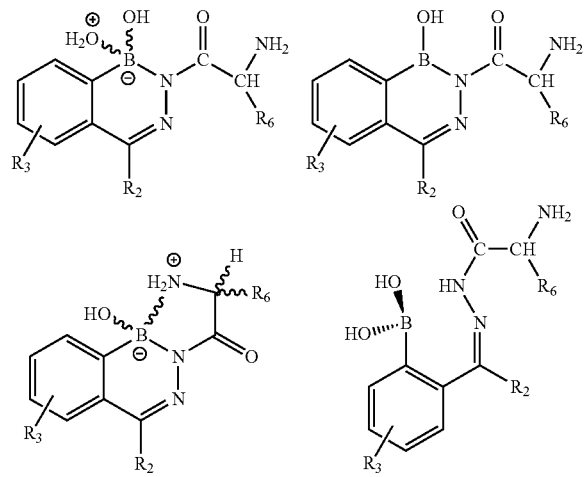

wherein:

$R_2$ is H or $CH_3$;

$R_3$ and $R_6$ are independently selected from the group consisting of alkyl or OR, wherein R is selected from the group consisting of alkyl, heteroalkyl, heteroaryl, alkylamine, alkylthiol, alkylbromide, arylbromide, $C_2$-$C_6$ alkanoyl, $CH_2Ar$ or $CH_2CH_2Ar$, in which a heteroatom of the heteroalkyl and heteroaryl is selected from the group consisting of nitrogen, oxygen sulfur, the Ar group of $CH_2Ar$ or $CH_2CH_2Ar$ is selected from the group consisting of a phenyl, a substituted phenyl ring, a naphtyl, a heteroaromatic ring, or fused ring comprising at least one ring heteroatom selected from nitrogen, oxygen and sulfur, a 4 to 7 member ring optionally incorporating one or more heteroatoms selected from oxygen, nitrogen, or sulfur, an aromatic ring optionally substituted with a fluorescent group, sugars or polyethylene glycol chain; and The composition may comprise a carbonyl substituted arylboronic acid selected from the group consisting of: an ortho formyl phenylboronic acid or ester derivative; an ortho ketone phenylboronic acid or ester derivative; an ortho aldehyde phenylboronic acid ester derivative of an amino acid; a ketone phenylboronic acid or ester derivative of an amino acid; an ortho aldehyde phenylboronic acid derivatized with an orthogonal reactive functional group; and a ketone phenylboronic acid derivatized with an orthogonal reactive functional group.

The spontaneous formation of the adduct is preferably substantially complete within a period of less than about 10 minutes at a temperature of about 25 C at a pH of 7, though the reaction need not be conducted under these conditions.

The following definitions, by way of example, describe the acceptable substituents. Where a generic term is used, that term encompasses various species within the genus. Each of the following groups, to the extent not incompatible with the ortho carbonyl boronic acid and/or α-effect amine compounds, or the intended application, may be included within any "R" group described herein.

The suffix "ene" appended to a group indicates that such a group is a diradical. By way of example only, a methylene is a diradical of a methyl group, that is, it is a —$CH_2$— group; and an ethylene is a diradical of an ethyl group, i.e., —$CH_2CH_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 24 carbon atoms (whenever it appears herein, a numerical range such as "1 to 24" refers to each integer in the given range; e.g., "1 to 24 carbon atoms" means that the alkyl group is selected from a moiety having 1 carbon atom, 2 carbon atoms, 3 carbon atoms, etc., up to and including 24 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, isopropyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=$CH_2$, —C($CH_3$)=$CH_2$, —CH=$CHCH_3$, —C($CH_3$)=$CHCH_3$. Alkenylene groups include, but are not limited to, —CH=CH—, —C($CH_3$)=CH—, —CH=$CHCH_2$—, —CH=$CHCH_2CH_2$— and —C($CH_3$)=$CHCH_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H.sub.y group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkyl-hydroxy, as defined herein.

"Alkoxyalkylaminoalkyl" refers to an alkyl radical, as defined herein, substituted with an alkylamine and substituted with an alkylalkoxy, as defined herein.

"aryl" refers to a cyclic organic composition with conjugated pi (sp2 or sp) bonding. The aryl functionality may optionally be substituted.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene, Theodora W. "Peter G M Wuts Protective groups in Organic Synthesis", 3$^{rd}$ Ed., John Wiley & Sons, New York, N.Y., 1999, which is incorporated herein by reference for this disclosure.

The term "amino acid fragment" refers to a portion of an amino acid, such the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) as well as the modified amino acids disclosed herein and further modified amino acids consistent with the disclosure and purposes hereof, or a dipeptide, tripeptide or other polypeptide comprising a combination of the 20 common amino acids or a non-natural amino acid.

The term "ester" refers to a chemical moiety with formula —XOOR, where R is selected from among alkyl, heteroalkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene, Theodora W. "Peter G M Wuts Protective groups in Organic Synthesis", 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)$_2$—, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Depending on the structure, a heteroaryl group can be a monoradical or a diradical (i.e., a heteroarylene group).

The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S((O))—$CH_3$, —$CH_2$—$CH_2$—S (O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, in some embodiments, up to two heteroatoms are consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

A "thioalkoxy" or "alkylthio" group refers to a —S-alkyl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$alkyl), (substituted or unsubstituted $C_3$-$C_6$cycloalkyl), heteroaryl, or heteroalkyl. The protecting groups that forms the protective derivatives of the above substituents include those found in sources such as Greene and Wuts, above.

Various pharmaceutically acceptable formulations are provided according to the present technology, for therapeutic or diagnostic purposes. The ortho carbonyl boronic acid and/or α-effect amine compounds may be provided to an animal or plant, to permit layer coupling of a corresponding α-effect amine compounds or ortho carbonyl boronic acid for therapeutic and/or diagnostic purposes. According to other embodiments, the ortho carbonyl boronic acid and α-effect amine compounds are combined as part of a manufacturing process to create a therapeutic or diagnostic agent, which can then be administered to an animal or plant, including a human subject or patient. U.S. Pat. No. 9,012,463, expressly incorporated herein by reference in its entirety, provides a detailed description of various pharmaceutical technologies, and subject to substitution of the present ortho carbonyl boronic acid and/or α-effect amine compounds and/or reaction product for the compounds discussed therein, the various pharmaceutical technologies and products are applicable hereto.

In some embodiments are provided pharmaceutically acceptable salts of the ortho carbonyl boronic acid and/or α-effect amine compounds described herein. By way of example only, are salts of a protonated composition formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptanoate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is a cation, such as sodium, lithium, potassium, calcium, magnesium, ammonium, and quaternary ammonium (substituted with at least one organic moiety) cations. Also described herein are salts having at least one sulfate group formed with a counterion, such as by way of example only, sodium, lithium, potassium, calcium, magnesium, ammonium, and quaternary ammonium cations.

In a further aspect are provided pharmaceutical compositions, which include a therapeutically effective amount of at least one of any of the compounds described herein, or a pharmaceutically acceptable salt or pharmaceutically acceptable solvent. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions. The effective amounts and concentrations are effective for ameliorating any of the symptoms of any of the diseases, disorders or conditions disclosed herein. The compositions may also be provided for diagnostic and/or research purposes.

In one aspect, provided herein are methods for treating a patient by administering a compound provided herein. For example, an animal ingests modified amino acids which contain the ortho carbonyl boronic acid or α-effect amine compounds, which are then incorporated into proteins. Thereafter, the corresponding α-effect amine or ortho carbonyl boronic acid compounds are either administered, or used to treat clinical specimens.

In some embodiments, compounds provided herein are administered to a human. In some embodiments, compounds provided herein are orally administered. In other embodiments, the pharmaceutical formulation that is formulated for a route of administration is selected from oral administration, parenteral administration, buccal administration, nasal administration, topical administration, or rectal administration.

Articles of manufacture including packaging material, a compound or composition or pharmaceutically acceptable derivative thereof provided herein, within the packaging material, and a label that indicates that the compound or composition, or pharmaceutically acceptable salt or pharmaceutically acceptable solvent thereof are provided.

Further described herein are pharmaceutical formulations comprising the ortho carbonyl boronic acid or α-effect amine compounds. In one embodiment the pharmaceutical formulation includes a pharmaceutical acceptable excipient. In some embodiments, pharmaceutical formulations provided herein are administered to a human or animal or experimental animal. In some embodiments, the compositions are orally administered. In any of the aforementioned aspects are further embodiments in which administration is enteral, parenteral, or both, and wherein (a) the effective amount of the compound is systemically administered to the animal or plant; (b) the effective amount of the compound may be administered orally to the animal; (c) the effective amount of the compound may be intravenously administered to the animal; (d) the effective amount of the compound administered by inhalation; (e) the effective amount of the compound is administered by nasal administration; or (f) the effective amount of the compound is administered by injection to the animal or plant; (g) the effective amount of the compound is administered topically (dermal) to the animal or plant; (h) the effective amount of the compound is administered by ophthalmic administration; or (i) the effective amount of the compound is administered rectally to the animal. In further embodiments the pharmaceutical formulation is formulated for a route of administration selected from oral administration, parenteral administration, buccal administration, nasal administration, topical administration, or rectal administration.

In any of the aforementioned aspects are further embodiments comprising single administrations of the effective amount of the pharmaceutical formulation, including further embodiments in which (i) the pharmaceutical formulations is administered once; (ii) the pharmaceutical formulations is administered to the animal once a day; (iii) the pharmaceutical formulations is administered to the animal multiple times over the span of one day; (iv) continually; or (v) continuously. The respective composition may be provided in growth media or supplements, or within foodstuffs.

In certain embodiments, provided herein is a pharmaceutical composition containing: i) a physiologically acceptable carrier, diluent, and/or excipient; and ii) one or more compounds provided herein.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated, or to arrive at a diagnosis. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case is optionally determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compounds described herein, age, weight, general condition of the subject, the condition being treated, the severity of the condition being treated, and the judgment of the prescribing physician.

The term "linkage," as used herein to refer to bonds or a chemical moiety formed from a chemical reaction between the functional group of a linker and another molecule. In some embodiments, such bonds include, but are not limited to, covalent linkages and non-covalent bonds, while such chemical moieties include, but are not limited to, esters, carbonates, imines, phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. In other embodiments, enzymatically unstable or degradable linkages means that the linkage is degraded by one or more enzymes. By way of example only, PEG and related polymers include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "subject" as used herein, refers to an animal which is the object of treatment, observation or experiment. By way of example only, a subject may be, but is not limited to, an animal including, but not limited to, a human.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The terms "diagnose" or diagnostic" refer to the ability to determine a state of an animal or plant based on a level or selective response. Often, the ortho carbonyl boronic acid or α-effect amine will be administered to the animal or plant to label a protein, surface, or other biological composition or structure. The corresponding α-effect amine or ortho carbonyl boronic acid is then applied to detect the label, which may be in vivo or in vitro.

Pharmaceutical Composition/Formulation

Pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of a compound described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a animal having a disease, disorder, or condition to be treated. Preferably, the animal is a human. The compounds, in some embodiments, are used singly or in combination with one or more therapeutic agents as components of mixtures.

The pharmaceutical formulations described herein in some embodiments, is administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

A "carrier" or "carrier materials" includes excipients in pharmaceutics and is selected on the basis of compatibility with compounds disclosed herein and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Moreover, the pharmaceutical compositions described herein, in some embodiments, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation. In another embodiment, some or all of the particles are microencapsulated. In still another embodiment, the particles are not microencapsulated and are uncoated.

A capsule may be prepared, for example, by placing the bulk blend of the formulation of the compound, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In other embodiments, the formulations described herein, which include solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference. See, e.g., Liberman et al., Pharmaceutical Dosage Forms, 2 Ed., Vol. 1, pp. 209-214 (1990); Singh et al., Encyclopedia of Pharmaceutical Technology, 2.sup.nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

Transdermal formulations may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments or diagnostic agents for any disease, disorder, or condition that benefit thereby.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

BRIEF DESCRIPTION OF THE DRAWINGS

The Invention will now be described with reference to the drawings, in which:

FIG. 1 shows the reaction of aromatic boronic acid or ester with α-effect amines at neutral pH.

FIG. 2 shows p-boronophenylalanine.

FIG. 3 shows reaction pathways of SAL of 2-formylphenylboronic acid (fPBA) with PhNHNH$_2$.

FIGS. 4A-4D show reaction kinetics of SAL and PhNHNH$_2$, compared with PBA and PhNHN$_2$

FIGS. 6A-6D show reaction kinetics of F-Tyr and CHzide, compared with fPBA and CHzide.

FIG. 15 shows linking of a protein with an fPBA linked to a substance of interest.

FIGS. 16, 17, 18, 19 and 20 show fPBA or esters thereof having various second functional groups.

FIGS. 24A and 24B show antibodies modified with a non-natural amino acid containing a hydrazide or a fPBA functionality.

FIGS. 25A and 25B show a coupling of Antibody-hydrazide with fPBA-derivatized taxol and a coupling of Antibody-2fPBA with hydrazide-derivatized taxol.

FIGS. 28 and 29 show a prior art and a new $^{18}$F PET radionuclide, respectively.

FIG. 30 shows a schematic depiction of metabolic labeling.

FIGS. 35A and 35B show a cyclized boronic acid reaction product in anhydrous and hydrated form.

FIG. 36 shows a tetracyclic product according to the present technology.

FIGS. 45 and 46 show prior art azide-alkyne cycloaddition coupling reactions.

DETAILED DESCRIPTION OF THE PREFERRED EMBODIMENTS

Procedure for forming a hydrazono or imino arylboronic acid, a 3,4-borazaisoquinoline or a related boron-containing heterocycle such as a 1,2-dihydrobenzo[d][1,2,3]diazaborinin-1-uide under biocompatible conditions.

General: Each component (o-carbonyl-substituted phenylboronic acid, alpha-effect amine-containing molecule) is dissolved in water or in buffer, normally pH 7, at room temperature. The solutions are mixed such that the molar ratio of the components in the mixture is 1:1. The concentration of each reagent is normally 30 µM to 5 mM. Normally a single product is formed. Stereoisomers can be formed when the product contains a chirality center. The structure of the product is identified by $^1$H, $^{13}$C and $^{11}$B NMR. Reactions are followed by absorption difference spectroscopy.

Example 1

Demonstration of reaction kinetics. Salicylaldehyde (Sal) represents a typical aromatic aldehyde used in a coupling reaction. Ortho-formylphenylboronic acid (2f-PBA) exemplifies the effect of the boronic acid at the ortho position. The α-effect amine is an aromatic hydrazine, e.g., phenylhydrazine. The reaction is shown in FIG. 3. Therefore the boronic acid substituted fPBA produces a stable cyclic product, while the product Sal with phenylhydrazine does not cyclize.

Example 2

Figure 4A:
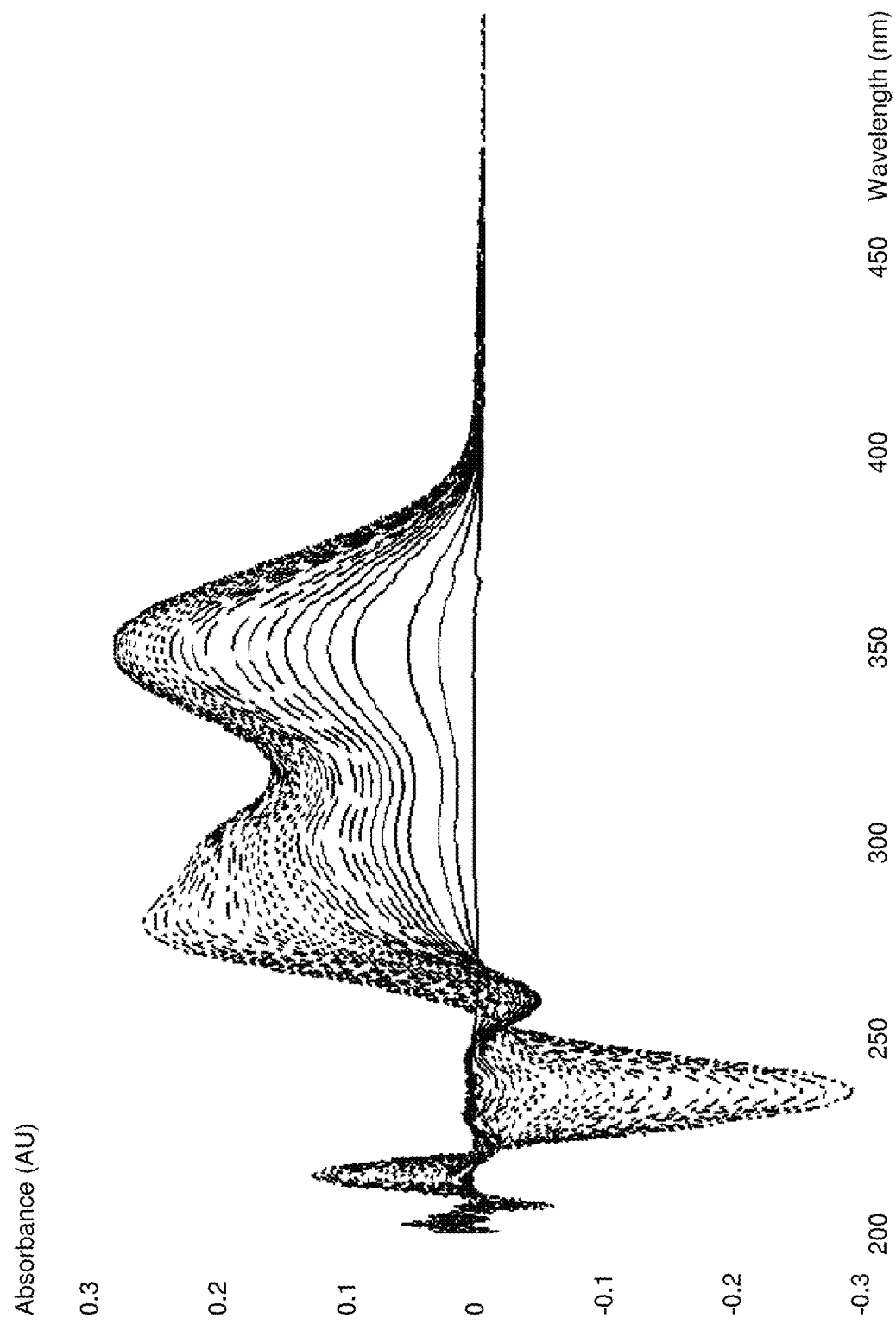
Figure 4C:
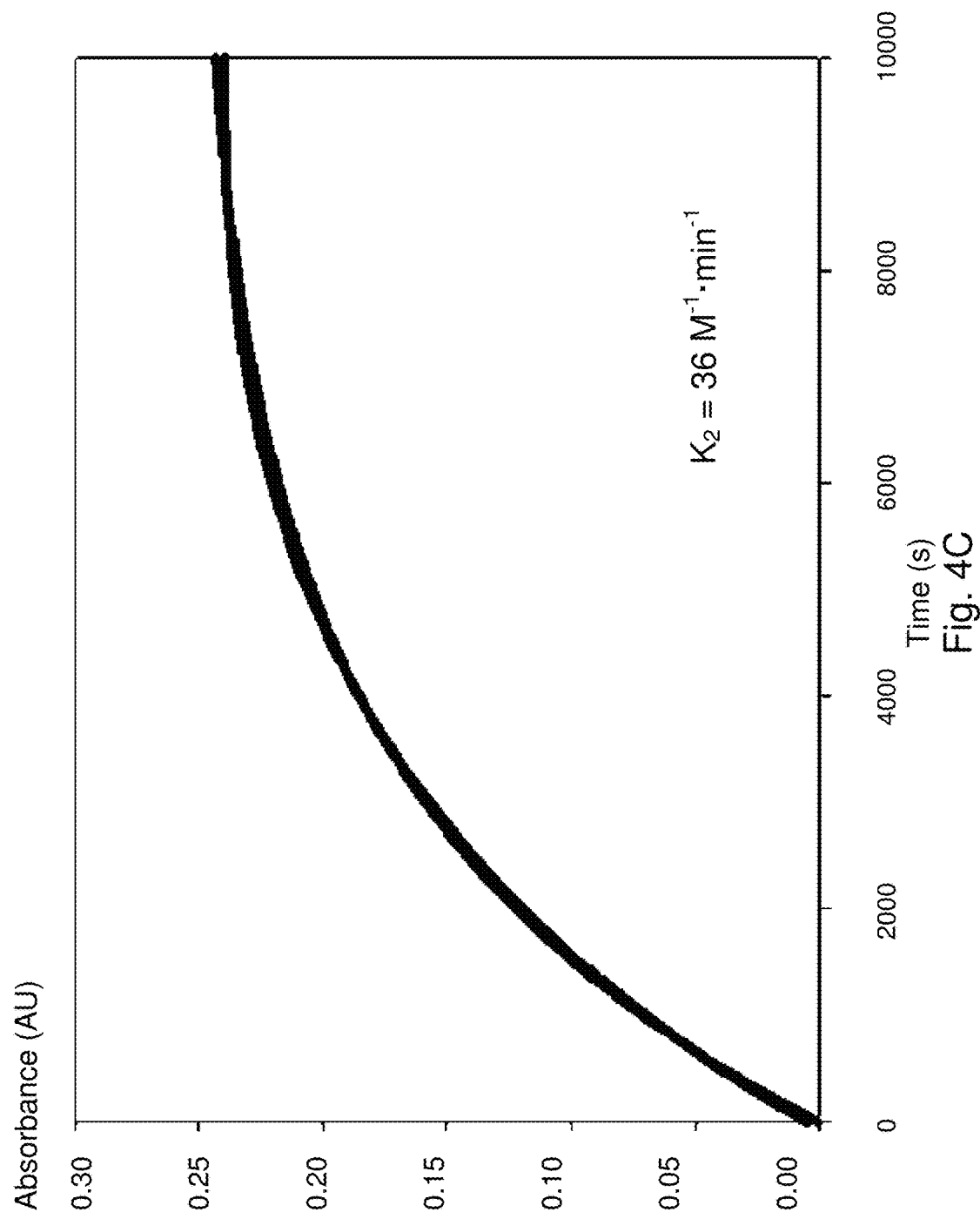
Figure 4D:
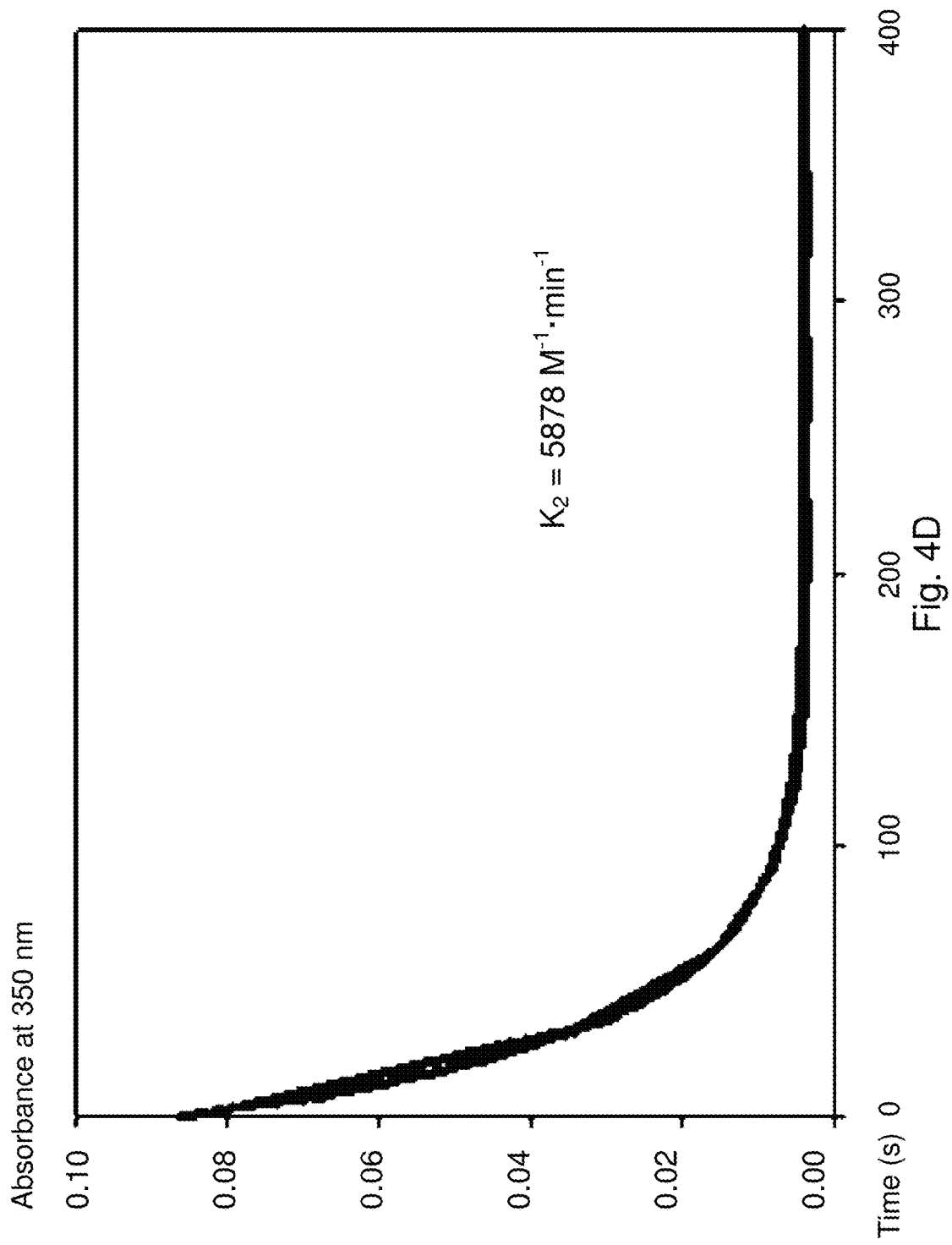
Figure 5:
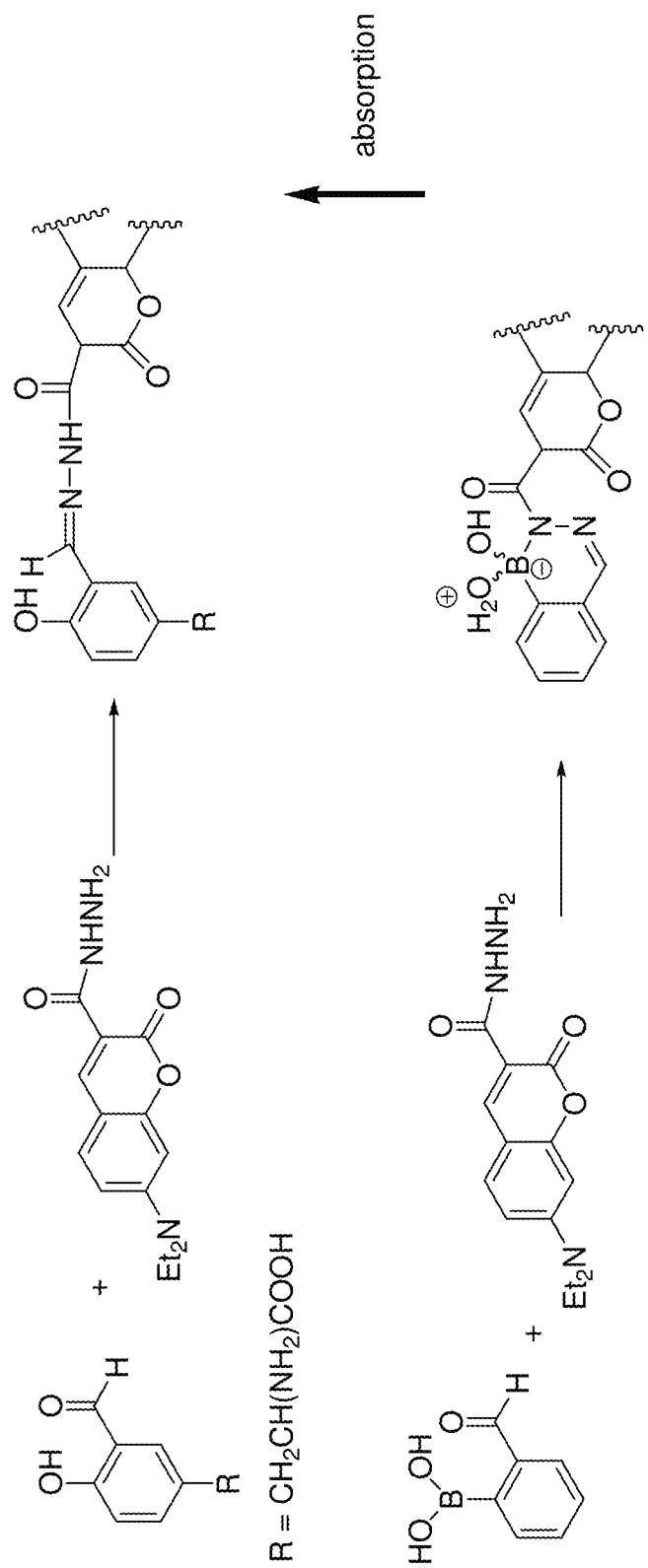
FIG. 5 shows a reaction of an aromatic aldehyde or boronic acid with a hydrazide.
Figure 6A:
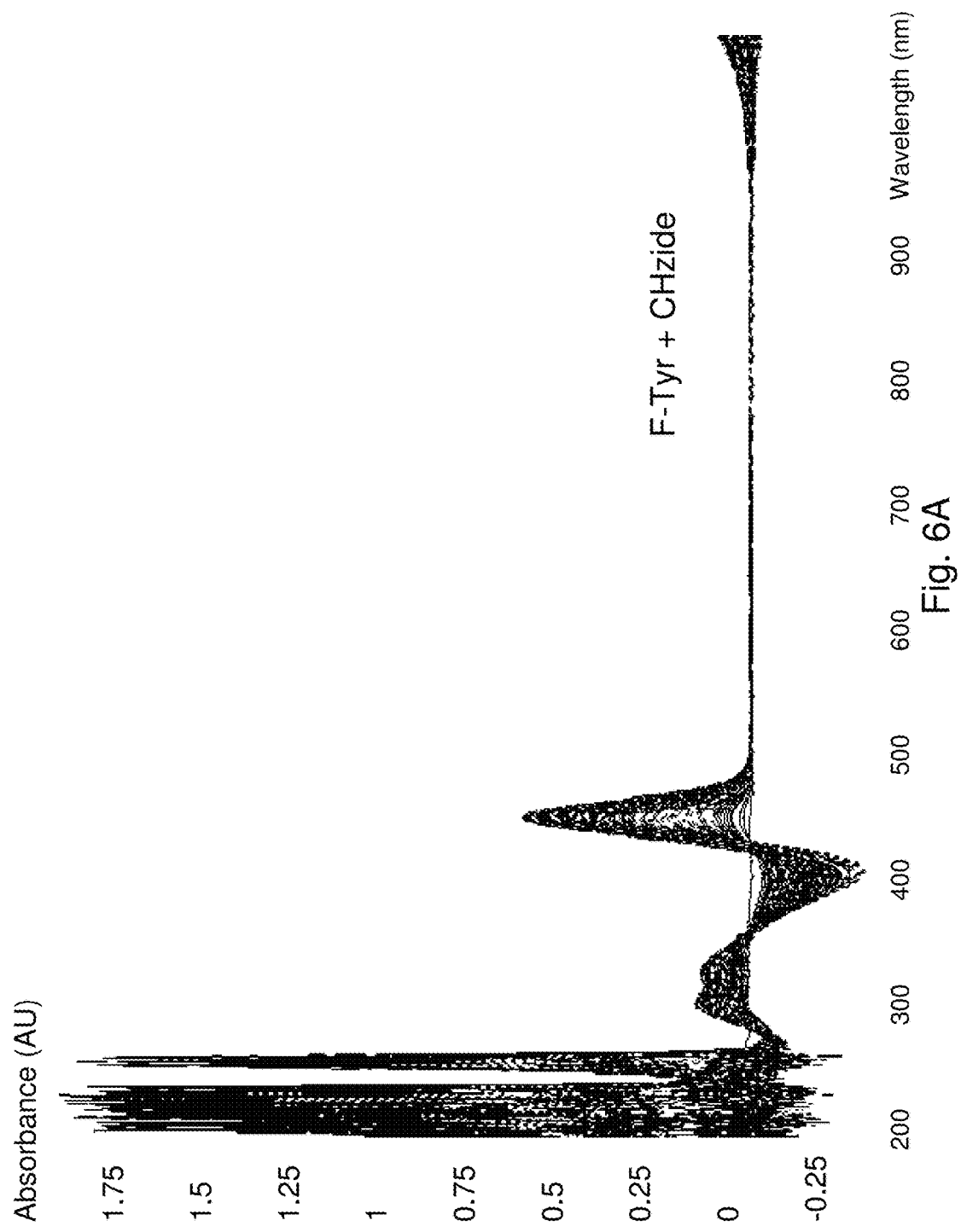
Figure 6B:
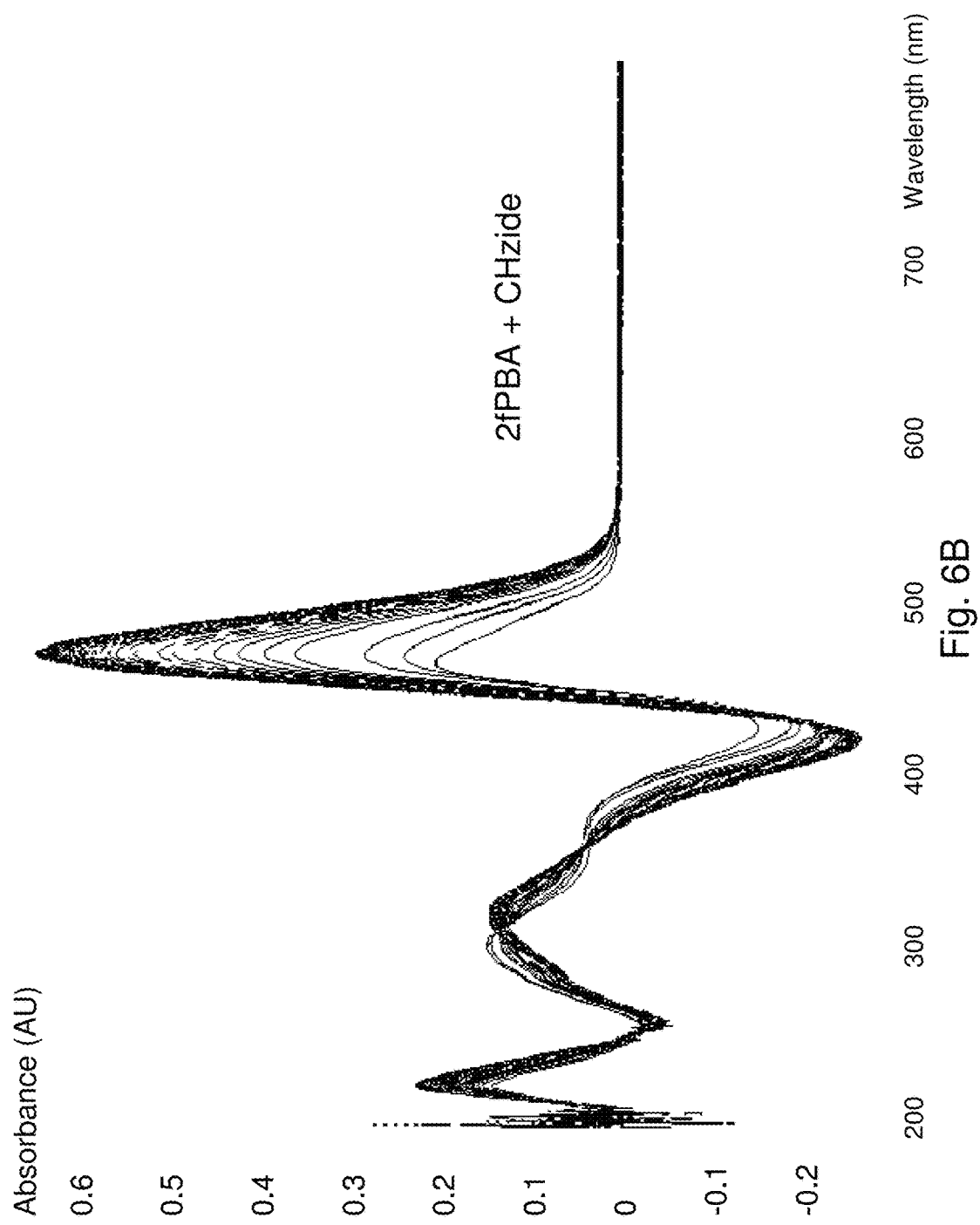
Figure 6D:
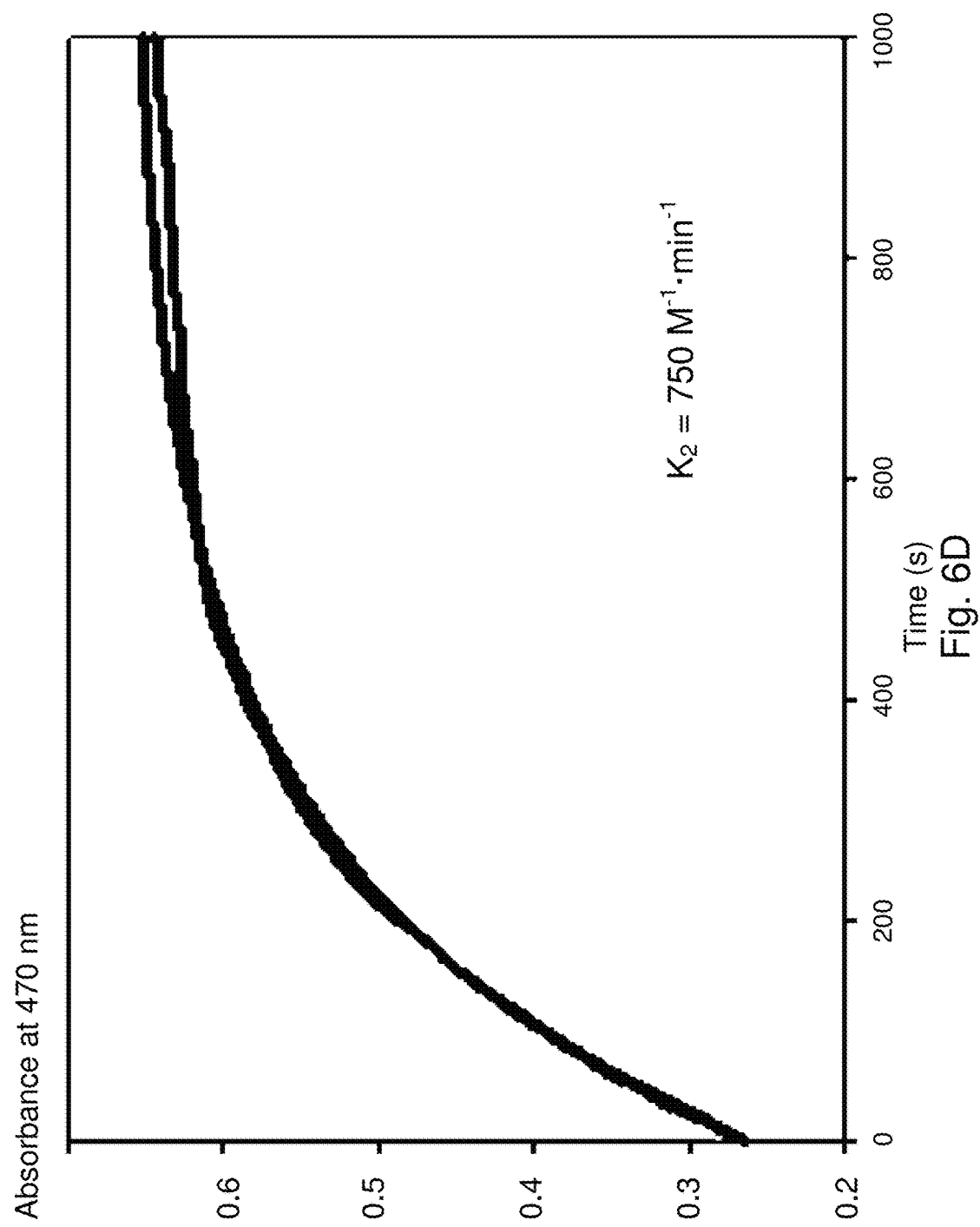

3-Formyltyrosine represents a typical aromatic aldehyde used in a coupling reaction. fPBA exemplifies the effect of the boronic acid at the ortho position. The α-effect amine is an aromatic hydrazide, e.g., 7-diethylamino coumarin 3-carbohydrazide (CHzide), as shown in FIG. 5. Hydrazides react with aldehydes only very slowly at neutral pH. The corresponding reaction with a boronic acid ortho- to the aldehyde is complete in minutes. The 3-formyl-4-boronophenylalanine derivative would be expected to engage in similar reactions, with similar kinetics, to fPBA, in this reaction, and therefore may be used to derivatize peptides for compatibility with the present click reaction.

Example 3

Figure 7:
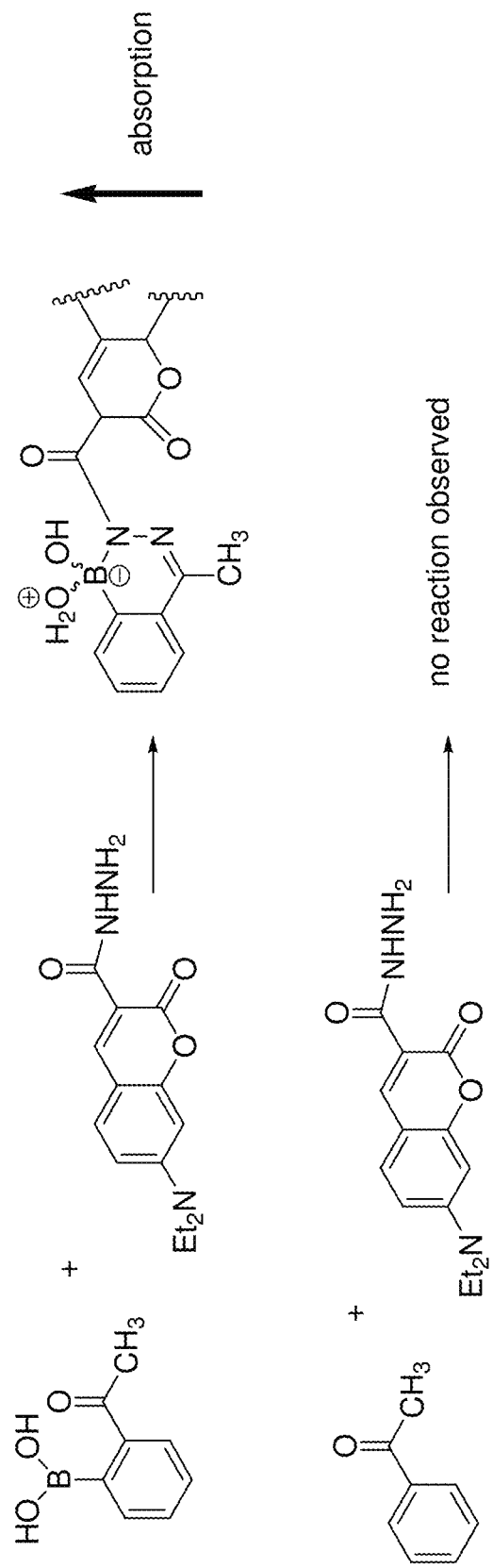
FIG. 7 shows the 2-boronic acid benzophenone with a hydrazide.
Figure 8A:
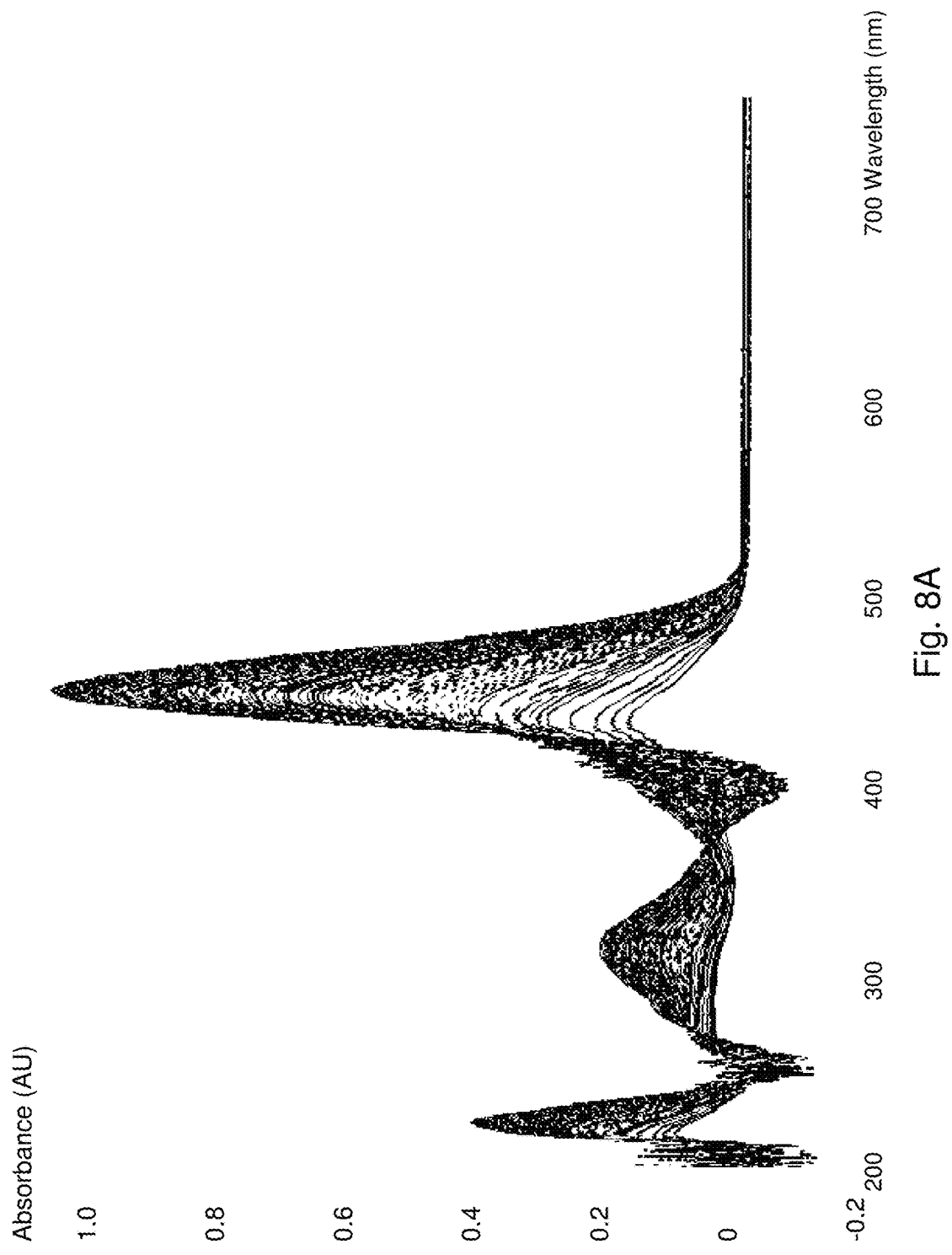
FIGS. 8A and 8B show reaction kinetics of 2-acetylphenylboronic acid with coumarin hydrazide.
Figure 8B:
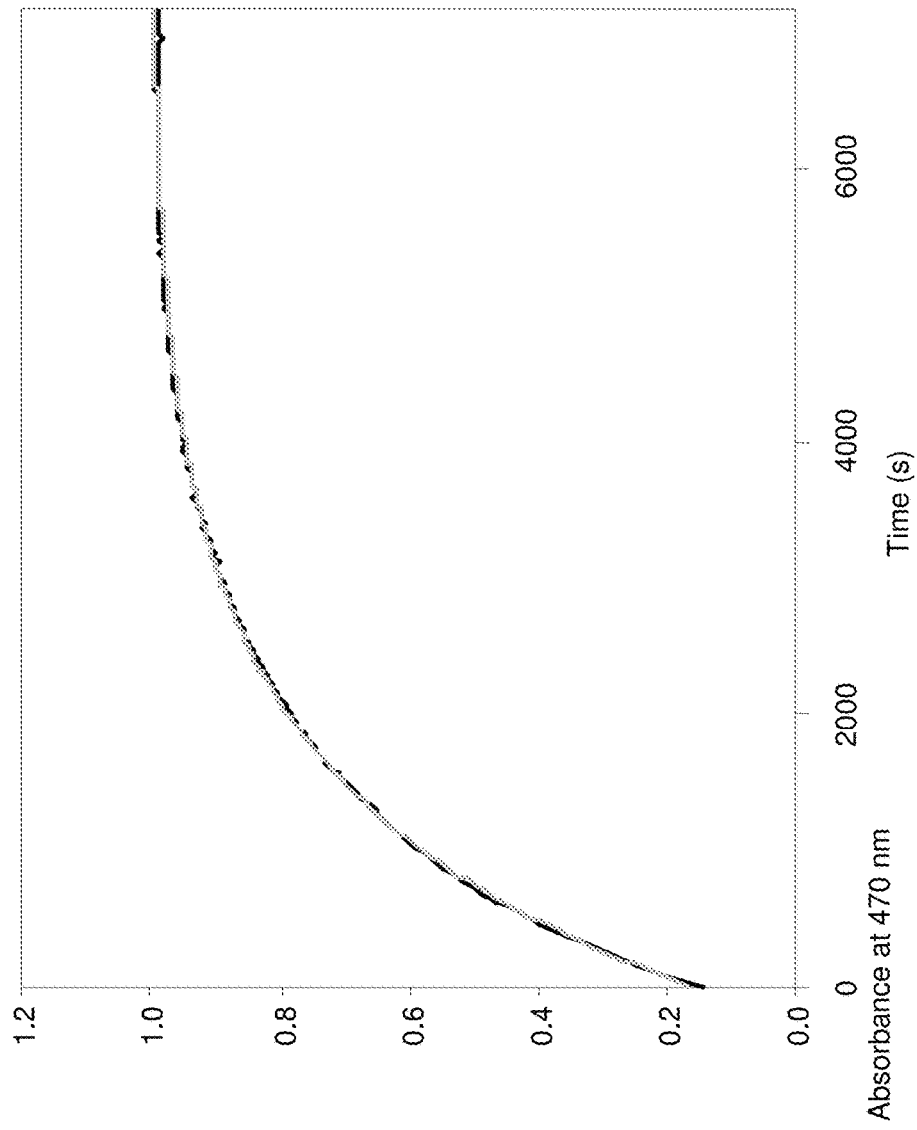

2-Acetylphenylboronic acid exemplifies a ketone-substituted phenylboronic acid. Acetophenone exemplifies an aromatic ketone. See FIG. 7. No reaction was observed with acetophenone under the general conditions noted above. However, the reaction of 2-acetylphenylboronic acid with 7-(diethylamino) coumarin-3-carbohydrazide does lead to an adduct. Note that this reaction is faster than the reaction in example 2. This is the opposite of the normal trend for hydrazone-forming reactions.

Example 4

Figure 9:
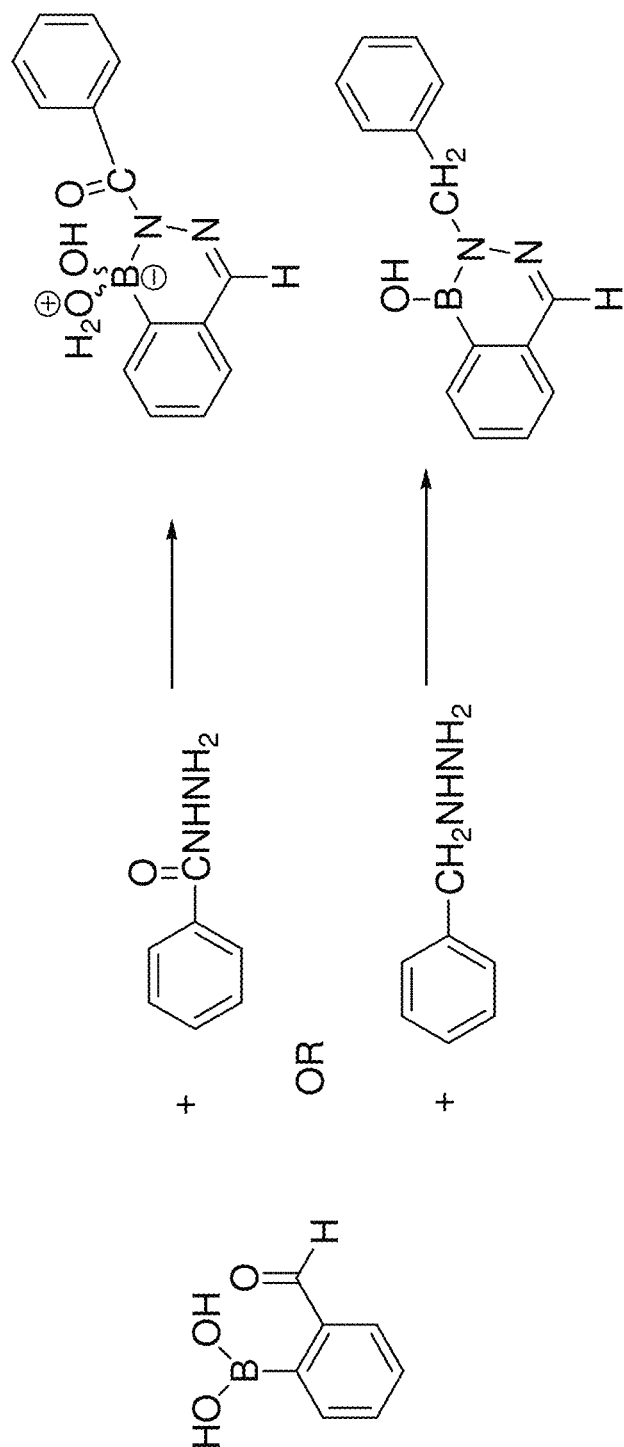
FIG. 9 shows the reaction of fPBA with phenylhydrazide and phenylhydrazine in neutral buffer.
Figure 10:
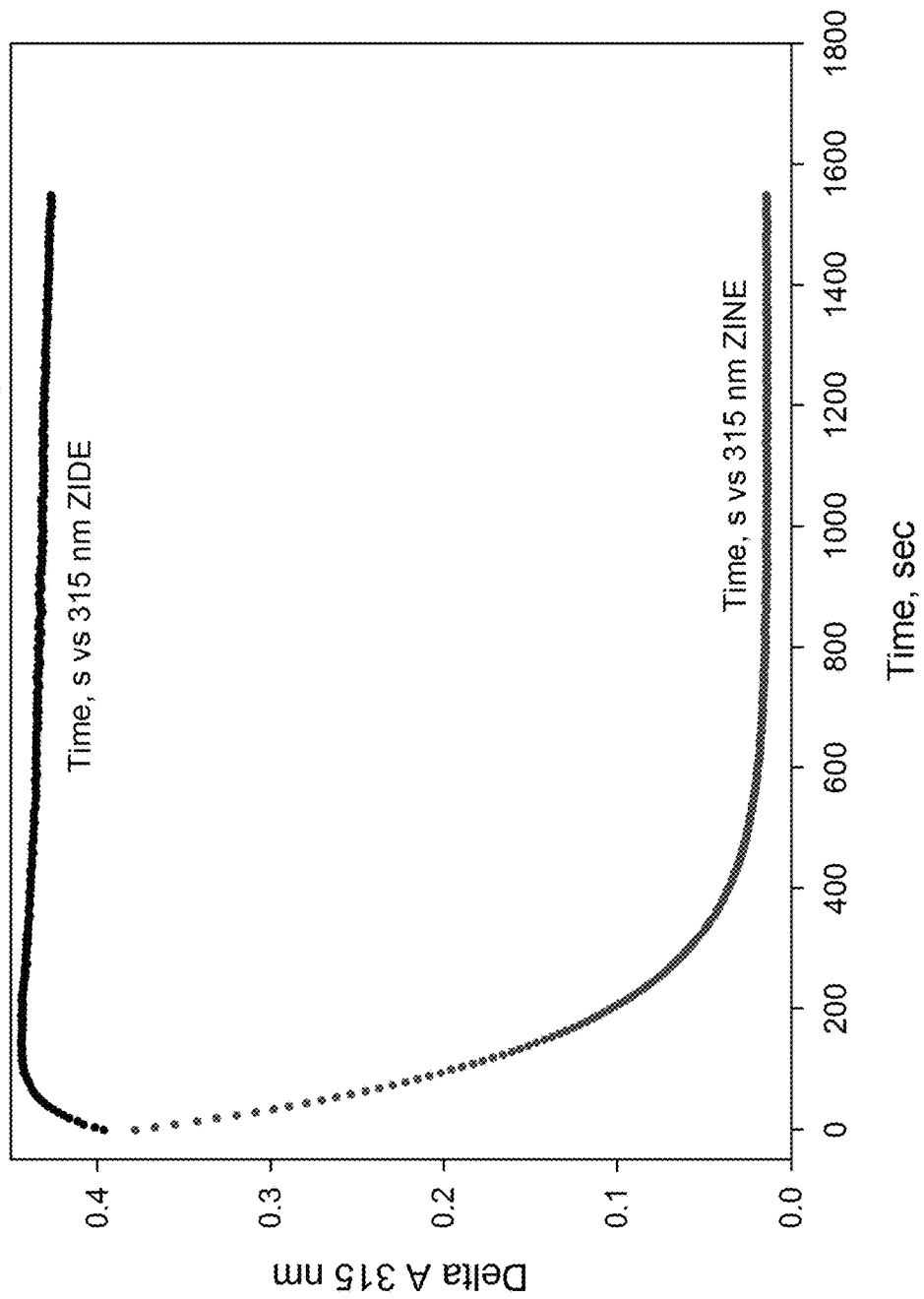
FIG. 10 shows reaction kinetics of phenylhydrazide and benzyl hydrazine with fPBA.

Comparison of Hydrazide vs. Hydrazine. A test was conducted to compare the reaction of fPBA with phenylhydrazide and benzylhydrazine in pH 7 buffer. The hydrazide reagent reacts faster. See FIG. 9.

Example 5

Figure 11:
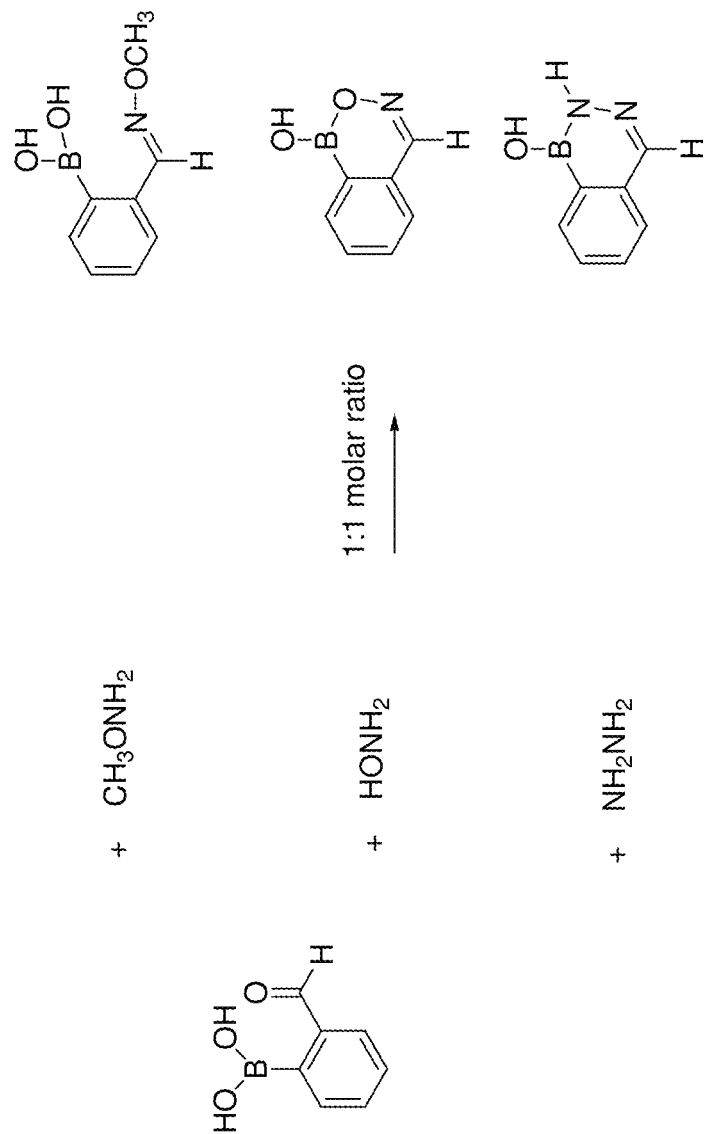
FIGS. 11 and 12 shows products of fPBA with O-methylhydroxylamine, hydroxylamine and hydrazine hydrate, and their respective NMR spectra.
Figure 12:
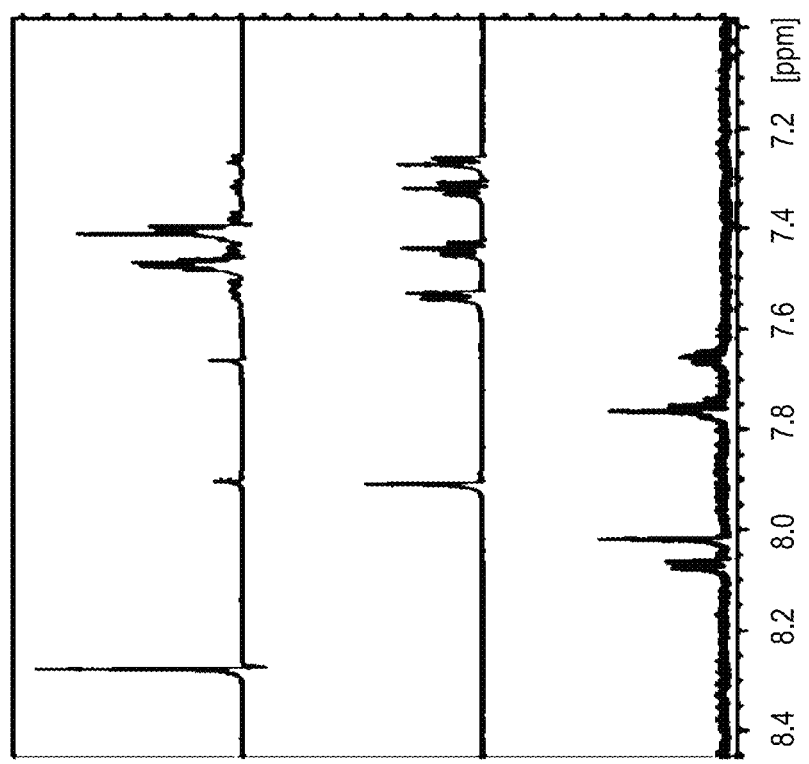

Reaction of fPBA with α-effect amines in pH 7 buffer. Each component (o-carbonyl-substituted phenylboronic acid, alpha-effect amine-containing molecule) is dissolved in 0.1 M phosphate buffer, pH 7, at room temperature. The concentration of each reagent is normally 1-2 mM. The solutions are mixed such that the molar ratio of the components in the mixture is 1:1. Proton NMR spectra are collected within 10 minutes after mixing. Shown in FIG. 12 are spectra of the results from mixing fPBA with O-methylhydroxylamine, hydroxylamine and hydrazine hydrate. See FIG. 11.

Example 6

Figure 42A:
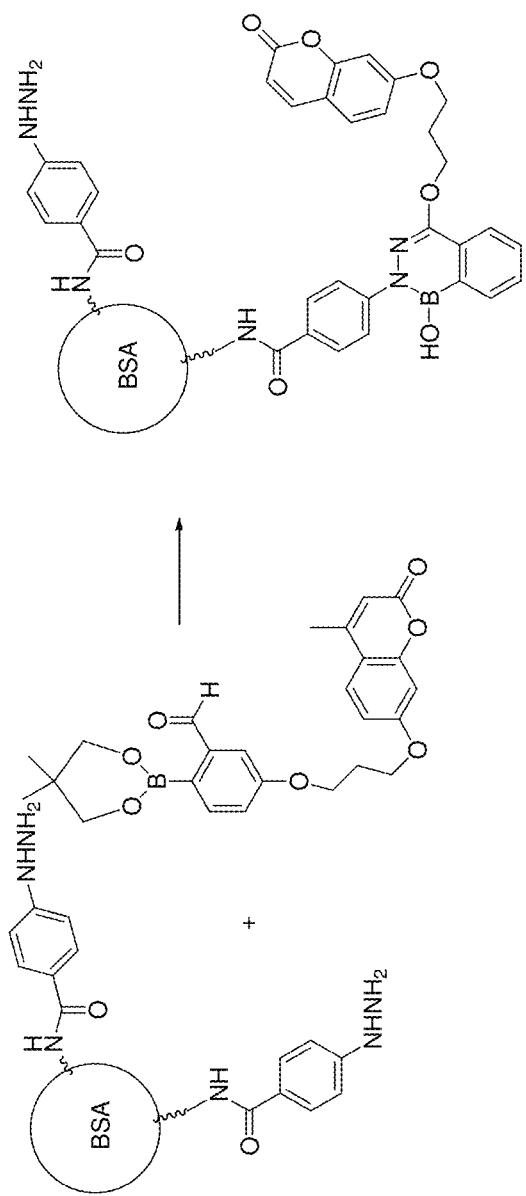
FIGS. 42A and 42B show linkage of hydrazine- and hydrazide-containing protein (bovine serum albumen) with coumarin-fPBA.
Figure 43:
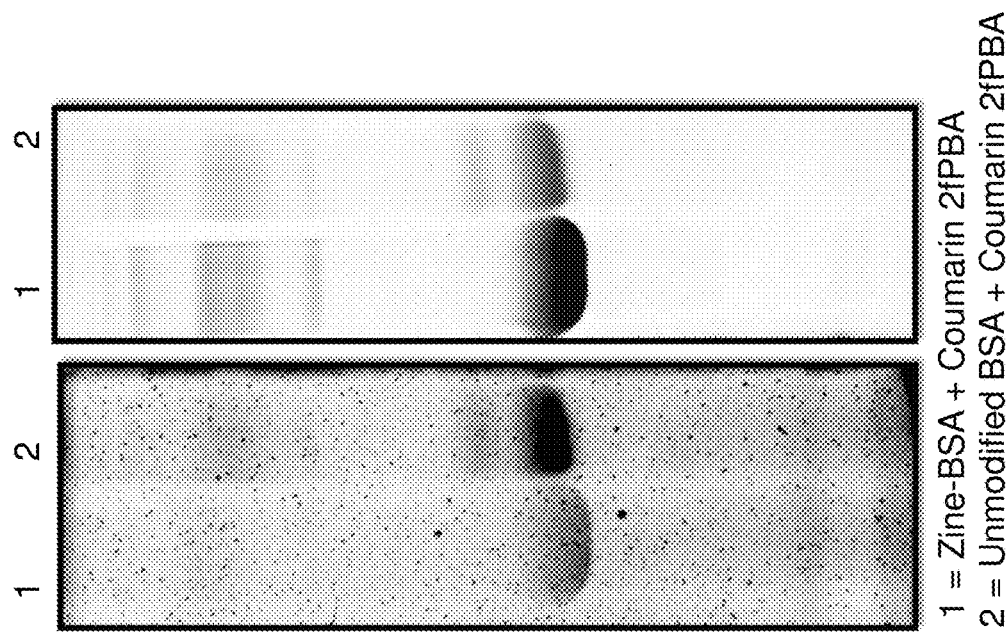
FIG. 43 shows a hydrazine-protein labeled with coumarin-fPBA imaged under long wavelength UV (left panel) and Coomassie blue dyed electrophoresis gel (right panel).
Figure 44:
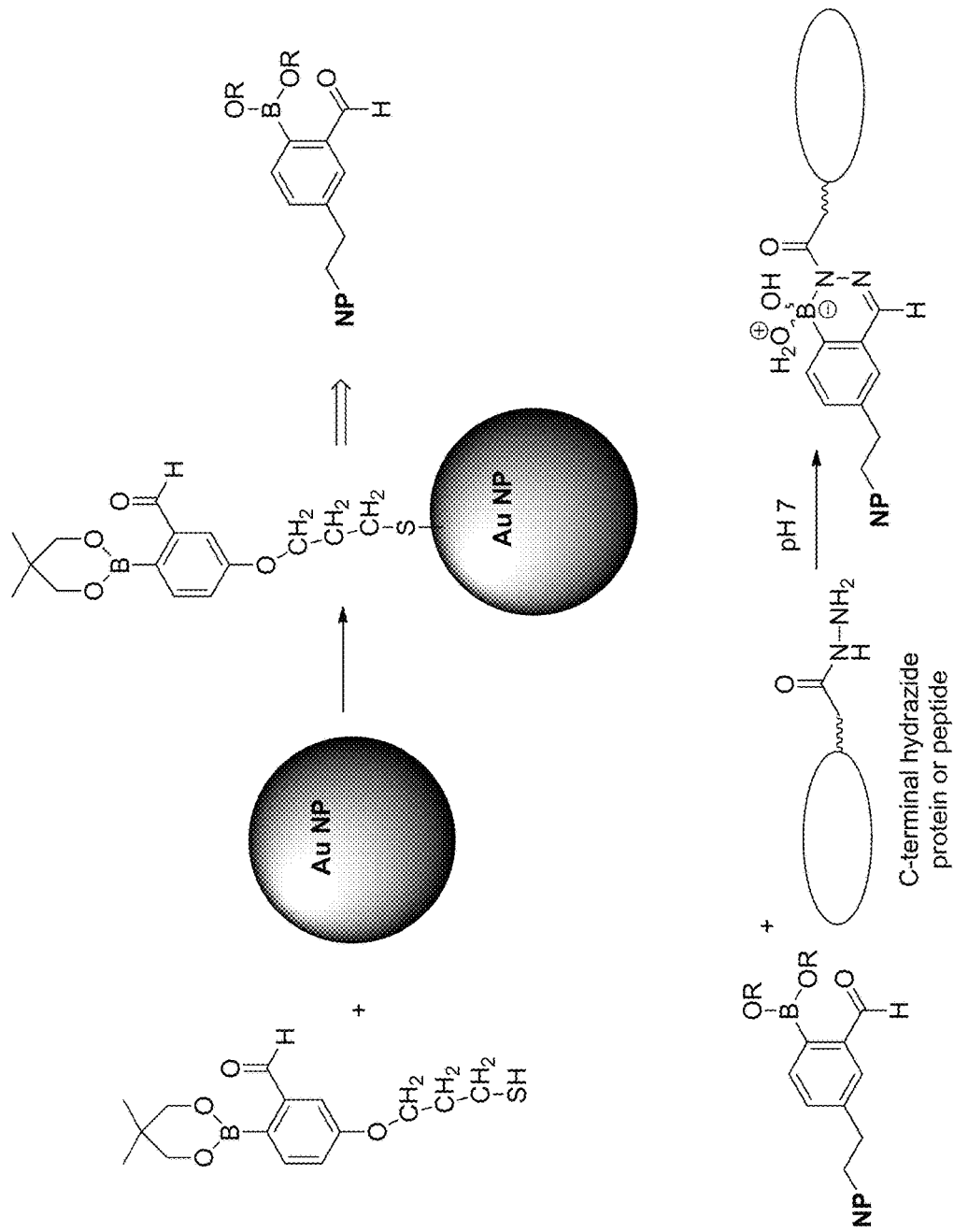
FIG. 44 shows a coupling reaction of a thiol linked boronic acid according to the present technology.

Coupling to Proteins. Hydrazine- and hydrazide-containing bovine serum albumen (BSA) were used as a model to demonstrate the coupling reaction between fPBA and alpha-effect amines on proteins. BSA containing phenylhydrazine functionalities was prepared by allowing the hydroxysuccimidyl ester of 4-(2-(propan-2-ylidene)hydrazinyl)benzoic acid to react with the protein. Hydrazine-BSA or unmodified BSA (final concentration 15 µM) was allowed to react with coumarin-2fPBA at room temperature for 5 min. See FIGS. 42A, and 43. The samples were then prepared for SDS PAGE analysis. The gel was visualized using long wave UV light and was then stained for protein, as shown in FIG. 43, in which the left panel is imaged under long wavelength UV (negative of the image is shown for clarity), and the right panel shows a Coomassie stained gel.

Figure 42B:
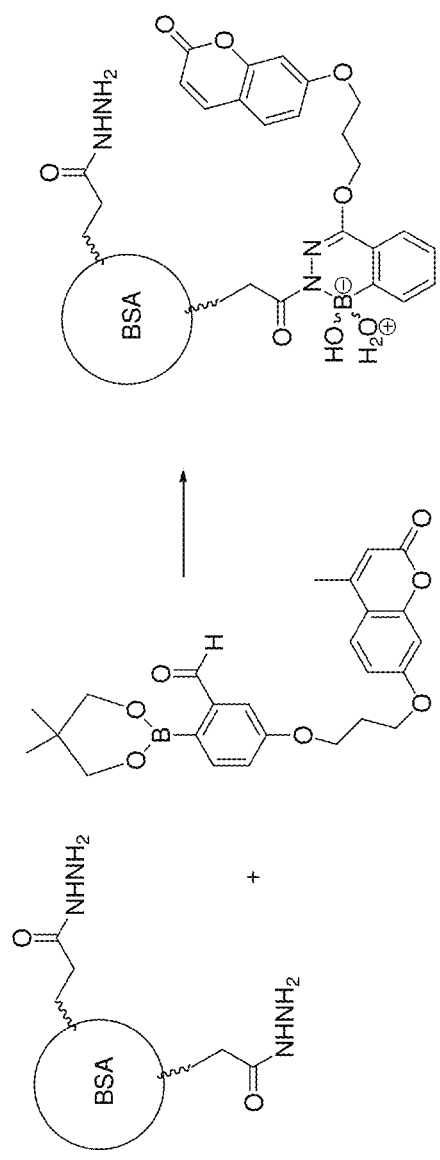
Figure 42C:
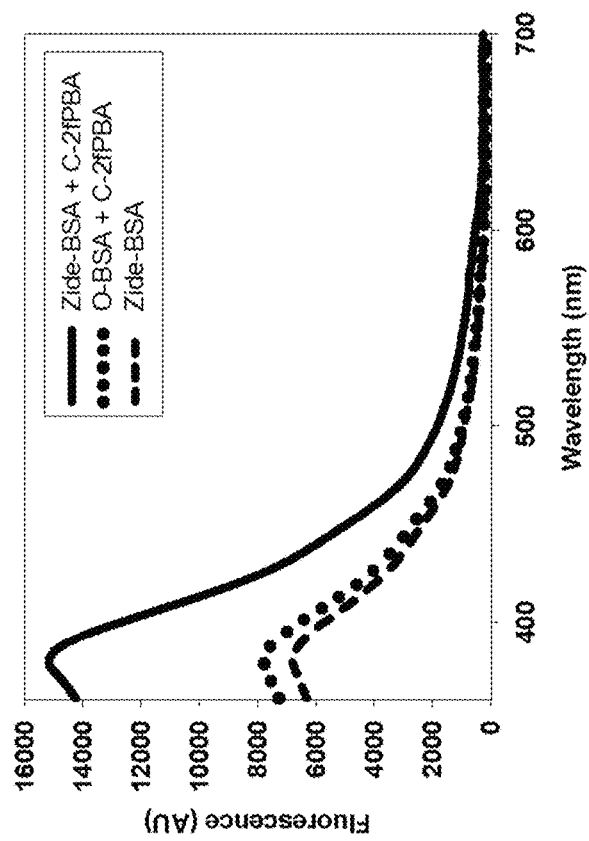
FIG. 42C shows a UV fluorescence plot of the reaction.

BSA with hydrazide functionalities was prepared by allowing oxidized BSA to react with adipic dihydrazide. BSA hydrazide (Zide-BSA, final concentration 10 µM) or oxidized BSA (O-BSA, final concentration 10 µM) was allowed to react with 20 µM C-2fPBA for 30 min in 10 mM sodium phosphate buffer (pH 7) prior to rapid gel filtration. The samples were excited at 340 nm, and emission spectra were collected. Each spectrum was normalized by protein concentration estimated by BCA assay. See FIGS. 42B and 42C.

Example 7

Bifunctional linkers. Molecules that possess a second reactive functional groups may be used to link the boronic acid or boronic ester conjugated to a carbonyl-containing moiety to the desired partner, as shown in FIG. 16. A boronic acid or boronic ester conjugated to a carbonyl-containing moiety. The ring may be substituted. A reactive functional group ($R_3$) is appended to the ring or part of a substituent attached to the ring. See FIG. 1, left structure.

Example 8

Figure 13:
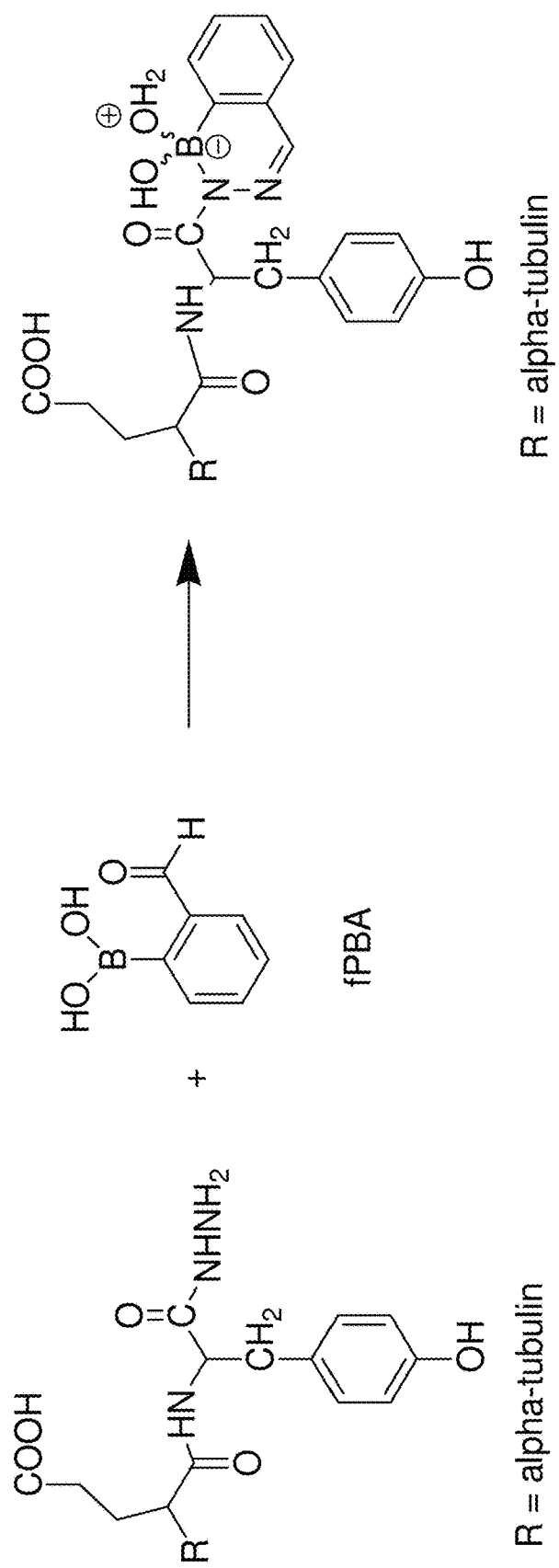
FIG. 13 shows a reaction of Tyrosine hydrazide tubulin and fPBA.
Figure 14:
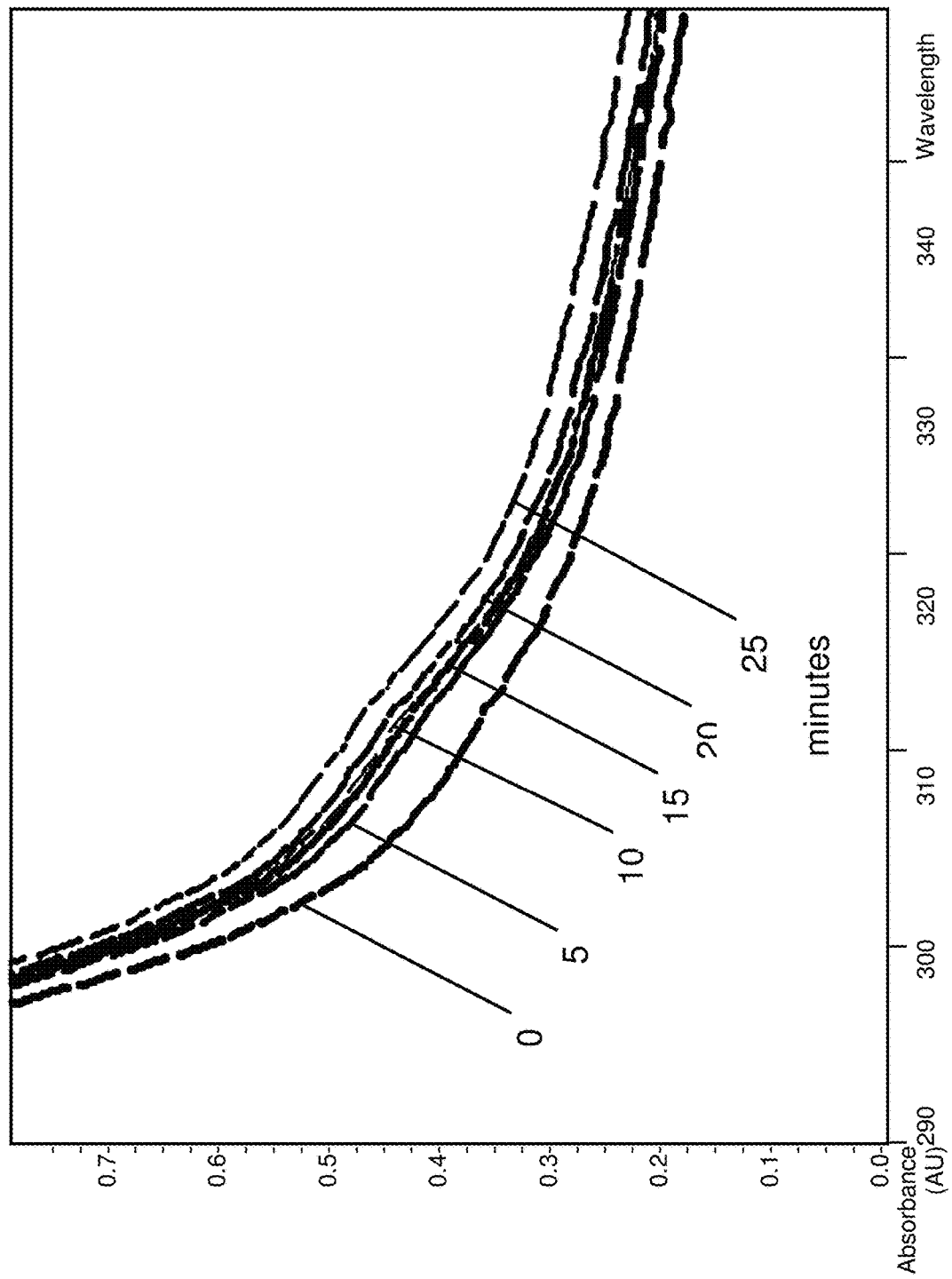
FIG. 14 shows a change in UV absorbance spectra over time.
Figure 18:
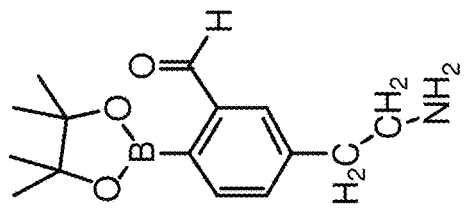

C-terminal protein labeling. Tyrosine hydrazide (Y-zide) is covalently bonded to the carboxyl terminus of alpha-tubulin using the enzyme tubulin tyrosine ligase as described in Mukherjee and Bane. (Mukherjee, K., and Bane, S. L. Site-specific fluorescent labeling of tubulin, In *Microtubules, In Vitro* 2nd ed., pp 1-12 (2013)). Y-zide-tubulin is equilibrated in PME buffer (0.1 M PIPES, 1 mM $MgSO_4$, 2 mM EGTA, pH 6.9) using rapid gel filtration. To the Y-zide-tubulin solution is added fPBA in 10 mM phosphate buffer, pH 7. The final concentration of Y-zide-tubulin and of fPBA is 93 µM. The reaction progress is monitored by absorption spectroscopy. The appearance of a shoulder at ~310 nm is indicative of product formation. See FIG. 13.

C-terminal hydrazide-containing proteins may be synthesized as described by Thom et al (Jennifer Thom; David Anderson; Joanne McGregor; Graham Cotton; Bioconjugate Chem. 2011, 22, 1017-1020). The probe or substance of interest (fluorophore, nanoparticle, protein, carbohydrate, surface, etc.) is covalently bonded to the reactive functional group on the probe (such as amine, thiol, azide, alkyne) using standard methods. The hydrazide-containing protein is allowed to react with the probe at neutral pH at microM to millimolar concentration and 1:1 stoichiometry at room temperature for 5-60 min. Progress of the reaction may be monitored by a change in the absorption spectrum. See FIG. 15.

Example 9

In addition to the method shown in Example 6, internal amino acid protein labeling may be performed using unnatural amino acid mutagenesis. Unnatural amino acid mutagenesis is a known method for adding reactive functional groups to proteins. This has been done with boronophenylalanine. (Liu, C. C., and Schultz, P. G. Adding New Chemistries to the Genetic Code, In Annual Review of Biochemistry, Vol 79 (Kornberg, R. D., Raetz, C. R. H., Rothman, J. E., and Thorner, J. W., Eds.), pp 413-444 (2010), U.S. Pat. No. 8,637,306, US 20090148887; WO 2009/059056 entitled "A Genetically Encoded Boronate Amino Acid," filed Oct. 30, 2008; U.S. Pat. Nos. 8,637,306; 8,632,970; 8,609,383; US 20110312027; US 20100297693; WO 2013/084198; Miyaura and Suzuki (1995) "Palladium-Catalyzed Cross-Coupling Reactions of Organoboron Compounds," Chemical Reviews 95: 2457 and Suzuki (1999) "Recent advances in the cross-coupling reactions of organoboron derivatives with organic electrophiles, 1995-1998," Journal of Organometallic Chemistry 576:147.) Therefore, the present technology provides that a protein labeled with an ortho-carbonyl substituted boronophenylalanine can be coupled using a click chemistry reaction to a hydrazide molecule as discussed herein for labeling C-termini. Alternatively, protein with an alpha-effect amine-containing unnatural amino acid could be prepared using unnatural amino acid mutagenesis or synthetic chemistry techniques for coupling to an ortho-carbonyl-substituted phenylboronic acid.

Example 10

Figure 20:
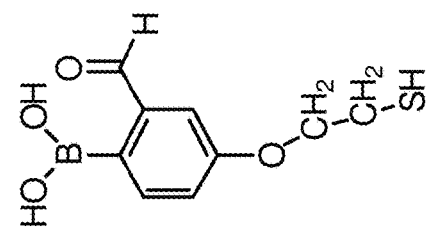
Figure 17:
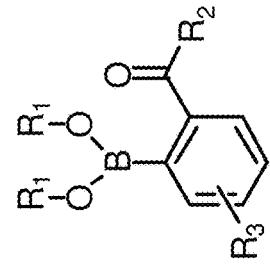
Figure 19:
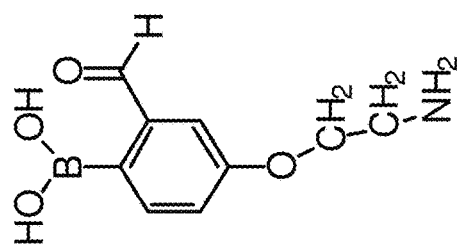

Drug-Antibody Conjugates are provided. Procedures for coupling fluorophores to proteins are generally applicable to coupling drugs to targeting proteins such as antibodies. One example of an antibody-drug complex is Trastuzumab emtansine, which has been used for HER2-positive metastatic breast cancer. Maytansine can be attached to the antibody through an MCC linker, as shown below. See, Elkins K et al. Mol Cancer Ther 2012; 11:2222-2232. See FIG. 20.

Figure 21:
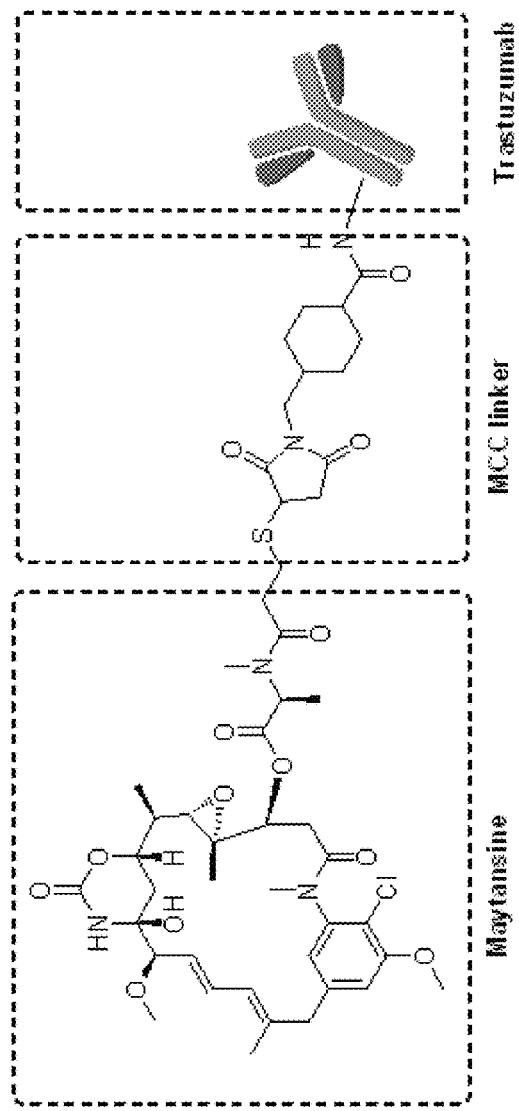
FIG. 21 shows a prior art Drug-Antibody Conjugates, Trastuzumab emtansine, for HER2-positive metastatic breast cancer linked through an MCC linker to maytansine.
Figure 22:
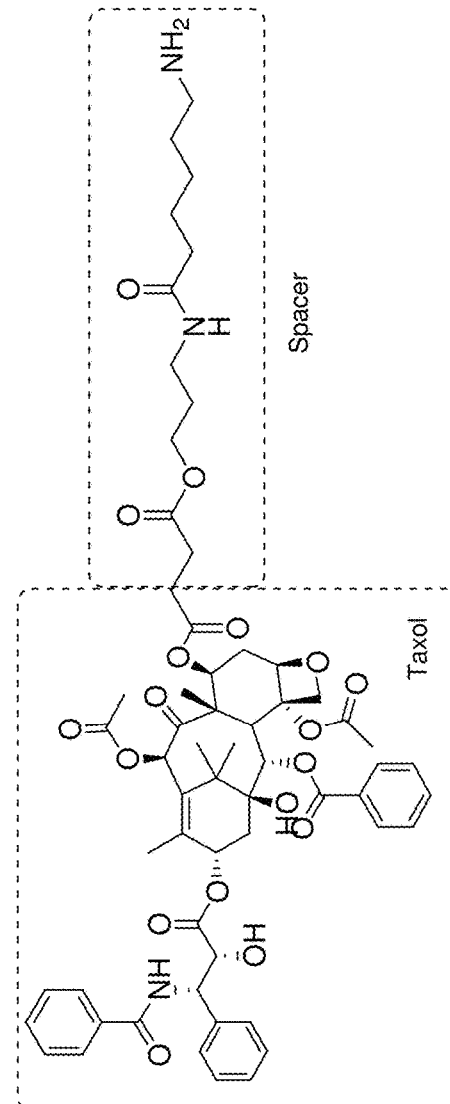
FIGS. 22 and 23 show Taxol linked through a spacer modified to terminate in a formylboronic acid fPBA for coupling to monoclonal antibodies.

Likewise, Taxol may be linked through a spacer modified to terminate in a formylboronic acid fPBA or a hydrazide for coupling to targeting proteins such as antibodies. A Taxol derivative with an amine-terminated spacer is known. Altering the spacer to terminate in an alpha-effect amine or an ortho carbonyl-phenylboronic acid allows for the drug to be attached to the appropriately modified antibody. See FIGS. 21 and 22.

Figure 23:
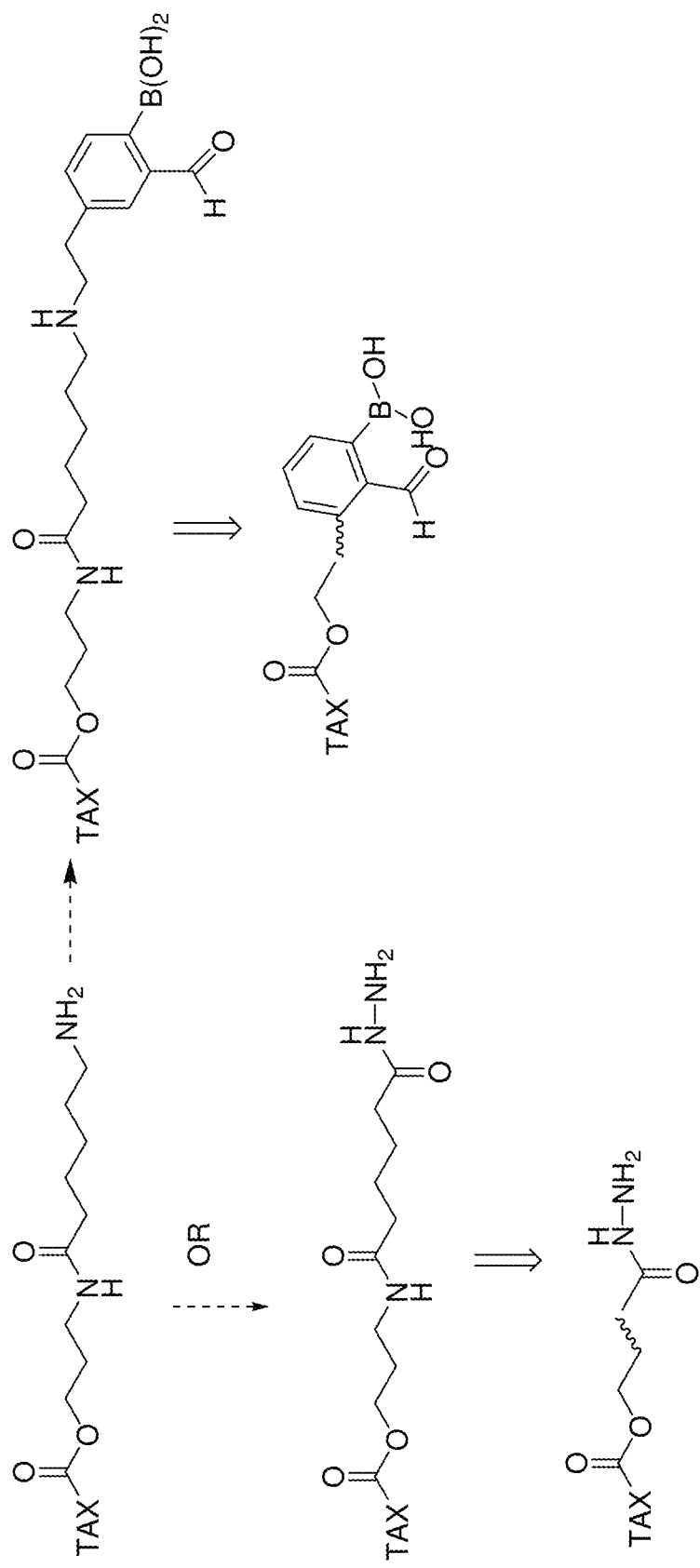

In order to add a hydrazide or ortho-carbonyl phenylboronic acid functionality to an antibody, a standard coupling procedure that uses maleimide reactive groups and Cys residues in the protein can be employed (Shen, B.-Q.; Xu, K.; Liu, L.; Raab, H.; Bhakta, S.; Kenrick, M.; Parsons-Reponte, K. L.; Tien, J.; Yu, S.-F.; Mai, E.; Li, D.; Tibbitts, J.; Baudys, J.; Saadi, O. M.; Scales, S. J.; McDonald, P. J.; Hass, P. E.; Eigenbrot, C.; Trung, N.; Solis, W. A.; Fuji, R. N.; Flagella, K. M.; Patel, D.; Spencer, S. D.; Khawlil, L. A.; Ebens, A.; Wong, W. L.; Vandlen, R.; Kaur, S.; Sliwkowski, M. X.; Scheller, R. H.; Polakis, P.; Junutula, J. R., Conjugation site modulates the in vivo stability and therapeutic activity of antibody-drug conjugates. *Nat. Biotechnol.* 2012, 30 (2), 184-189.) A bifunctional reagent that possesses a maleimide and either a hydrazide or a formylboronic acid can be used to add the linker, as shown in FIG. 23.

Alternatively, the antibody may be expressed with unnatural amino acids, as is known with different reactive amino acids. (Axup, J. Y., Bajjuri, K. M., Ritland, M., Hutchins, B. M., Kim, C. H., Kazane, S. A., Halder, R., Forsyth, J. S., Santidrian, A. F., Stafin, K., Lu, Y., Tran, H., Seller, A. J., Biroc, S. L., Szydlik, A., Pinkstaff, J. K., Tian, F., Sinha, S. C., Felding-Habermann, B., Smider, V. V., and Schultz, P. G. (2012) Synthesis of site-specific antibody-drug conjugates using unnatural amino acids, *Proc. Natl. Acad. Sci. USA* 109, 16101-16106; Tian, F.; Lu, Y.; Manibusan, A.; Sellers, A.; Tran, H.; Sun, Y.; Phuong, T.; Barnett, R.; Hehli, B.; Song, F.; DeGuzman, M. J.; Ensari, S.; Pinkstaff, J. K.; Sullivan, L. M.; Biroc, S. L.; Cho, H.; Schultz, P. G.; DiJoseph, J.; Dougher, M.; Ma, D.; Dushin, R.; Leal, M.; Tchistiakova, L.; Feyfant, E.; Gerber, H.-P.; Sapra, P., A general approach to site-specific antibody drug conjugates. *Proc. Natl. Acad. Sci. USA* 2014, 111 (5), 1766-1771.). See FIGS. 24 and 25.

A key advantage of this technology is that the drug may be coupled to the antibody quickly, at neutral pH and without excess reagent. Integrating a non-natural amino acid reduces post-production steps for the antibody, and allows the antibody to be labeled after addition to a biological system; the standard coupling procedure is not selective, and will add hydrazine functionality to all exposed cysteine residues.

Example 11

Nanoparticle-biomolecule conjugates. Gold nanoparticles (1-100 nm), nanospheres and nanorods have applications in photothermal therapy and optical and contrast imaging techniques. (Algar, W. R., Prasuhn, D. E., Stewart, M. H., Jennings, T. L., Blanco-Canosa, J. B., Dawson, P. E., and Medintz, I. L. (2011) The Controlled Display of Biomolecules on Nanoparticles: A Challenge Suited to Bioorthogonal Chemistry, Bioconj. Chem. 22, 825-858.) Targeting nanoparticles to particular in vivo locations requires conjugation to a biological moiety. The gold nanostructure must first be coated with an appropriate linkers, which is generally accomplished through bifunctional thiol ligands, as shown in FIG. 45.

Example 12

Figures 26A, 26B:
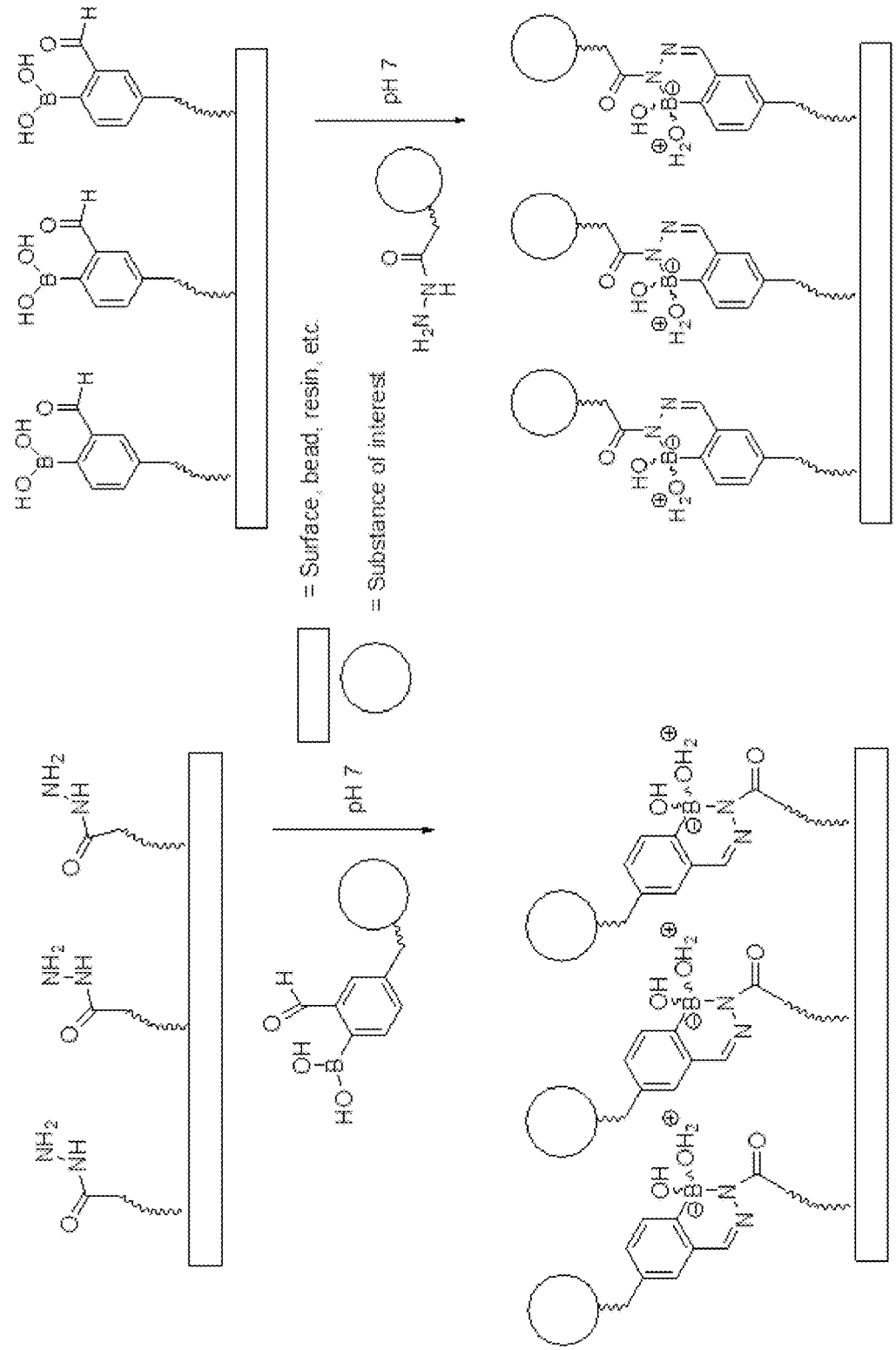
FIGS. 26A and 26B show biomolecule immobilization with hydrazide-functionalized surface and biomolecule immobilization with fPBA-functionalized surface, bead, resin, or other material

Biomolecules may be attached to a surface according to the present technology. 96 well plates with hydrazide functional groups are commercially available (for example, Corning Carbo-BIND™ 96 well plates). Biomolecules that have been covalently modified with the reactive ortho-carbonyl phenylboronic acid can then be attached to these plates by adding the desired molecule to the well. If the modified protein is an antibody, then such plates may be used for ELISA (Brillhart, K. L., and Ngo, T. T. (1991) Use Of Microwell Plates Carrying Hydrazide Groups To Enhance Antibody Immobilization In Enzyme Immunoassays, J. Immunol. Methods 144, 19-25.). Other commercially available products include hydrazide-modified magnetic beads (BcMag® Hydrazide-modified Magnetic Beads; Bioclone Inc), hydrazide containing resins (Affi-Gel Hz hydrazide gel, Bio-Rad), glass slides, membranes, plates, and nanoparticles (Biosynthesis, Inc.) See also Applying Genomic and Proteomic Microarray Technology in Drug Discovery, Second edition. (Robert S. Matson, ed. CRC Press, 2013). See FIG. 26A.

A bifunctional ortho-carbonyl phenylboronic acid linker can also be attached to appropriately functionalized solid supports, surfaces or beads. The production is within the ordinary skill in the art, for example, immobilized phenylboronic acids are commercially available (Pierce™ Boronic Acid Resin, Affi-Gel® Boronate Affinity Gel), Such surfaces would be then be available for linking to substances containing alpha-effect amines. See FIG. 26B.

Example 13

Figure 27:
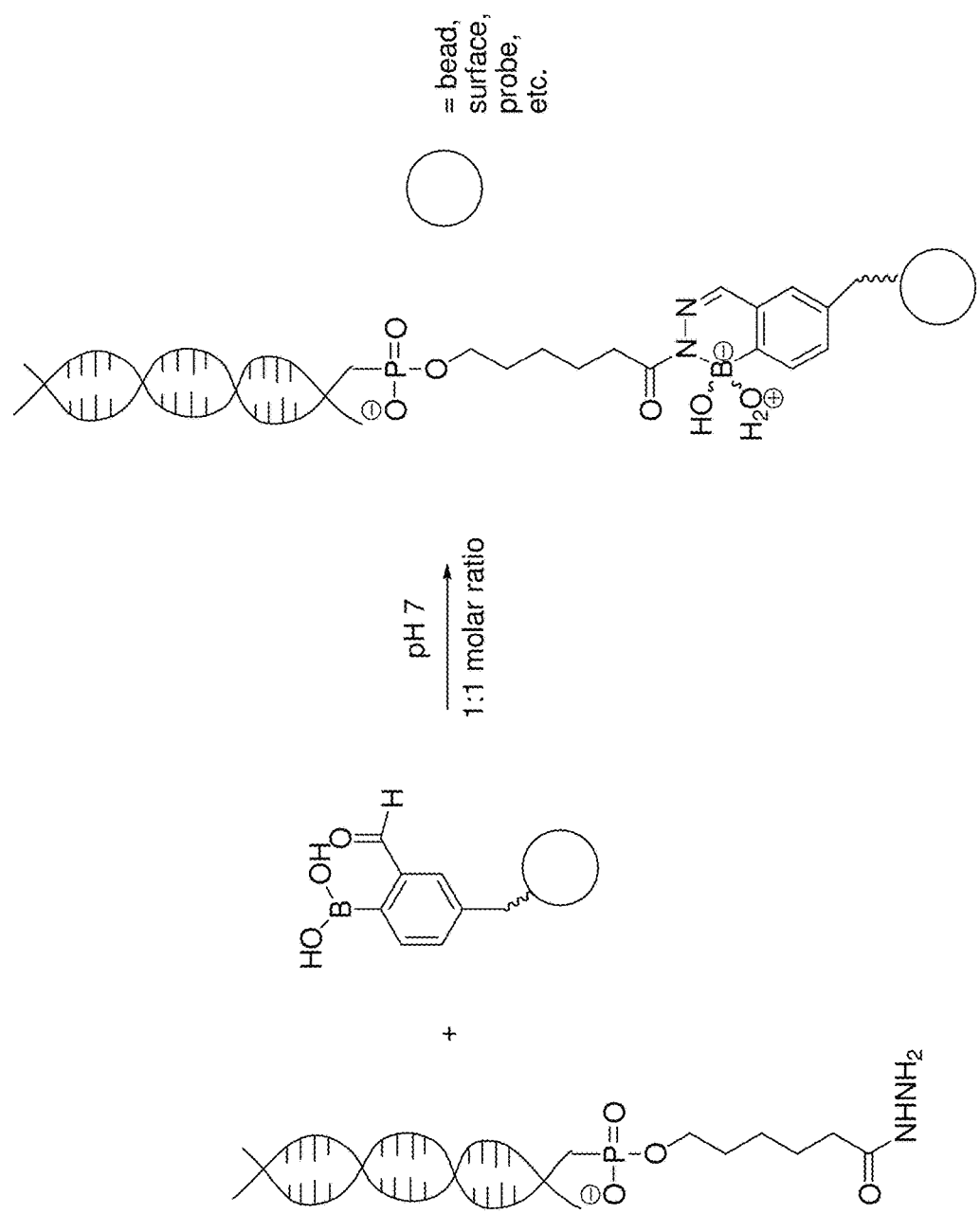
FIG. 27 shows hydrazide-oligonucleotide immobilization on fPBA-functionalized surface, bead, resin, or other material.

Nucleic acid conjugates are provided. Hydrazides can be appended easily to nucleic acids. (See, for example, Ghosh, S. S., Kao, P. M., and Kwoh, D. Y. (1989) Synthesis Of 5'-Oligonucleotide Hydrazide Derivatives And Their Use In Preparation Of Enzyme Nucleic-Acid Hybridization Probes, Analytical Biochemistry 178, 43-51; Raddatz, S., Mueller-Ibeler, J., Kluge, J., Wass, L., Burdinski, G., Havens, J. R., Onofrey, T. J., Wang, D., and Schweitzer, M. (2002) Hydrazide oligonucleotides: new chemical modification for chip array attachment and conjugation, Nucleic Acids Res. 30, 4793-4802; Zatsepin, T. S., Stetsenko, D. A., Gait, M. J., and Oretskaya, T. S. (2005) Use of carbonyl group addition-elimination reactions for synthesis of nucleic acid conjugates, Bioconj. Chem. 16, 471-489.) These hydrazide modified nucleic acids are then attached to a probe, nanoparticle, surface, etc. using the boronic acid-based linker. See FIG. 27.

Example 14

Targeting PET Probes. A problem for preparing radiolabeled conjugates for positron emission tomography (PET) use is the short half-life of $^{18}$F, a commonly used emitter. The longer the time required to prepare the conjugate, the less isotope will be available for patient imaging. The present technology can shorten the time to prepare the conjugate, and the reaction is stoichiometric, and the reagents and product are bioorthogonal (to the limits of $^{18}$F radiopharmaceutical pharmacology), so a purification step is not necessary. Click-Chemistry Reactions in Radiopharmaceutical Chemistry: Fast & Easy Introduction of Radiolabels into Biomolecules for In Vivo Imaging. Current Medicinal Chemistry, 2010, 17, 1092-1116. Therefore, 4-$^{18}$F-fluoro-N-(prop-2-ylyl)-benzyamide (FIG. 28) is replaced with 4-$^{18}$F-fluoro-benzoyl hydrazine (FIG. 29).

Example 15 Carbohydrate Labeling

Figure 31A:
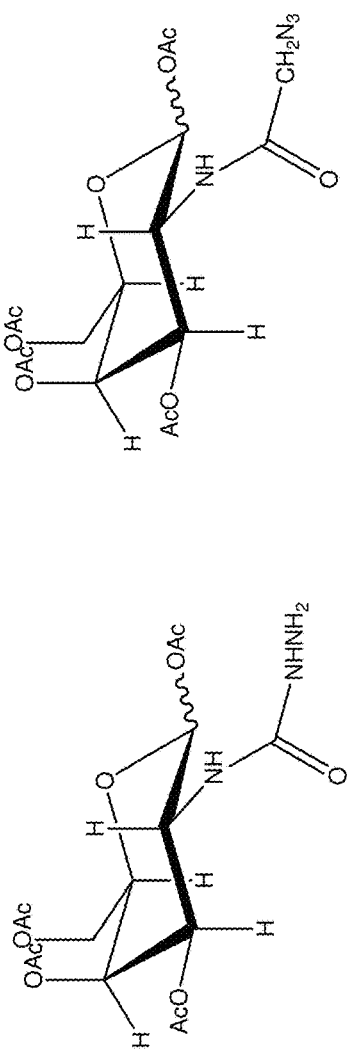
FIGS. 31A and 31B show semicarbazide and azide derivatized sugars.
Figure 31B:
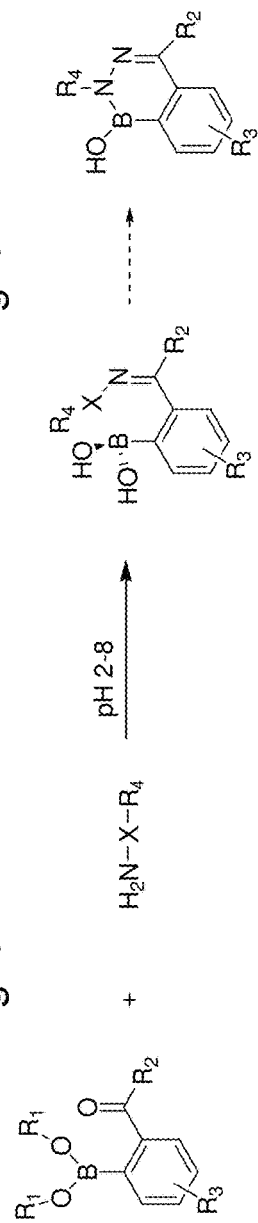
Figure 32:
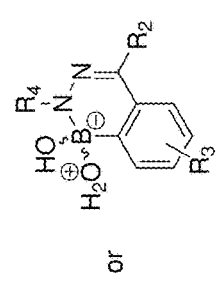
FIG. 32 shows a generic reaction according to the present technology.
Figure 33C:
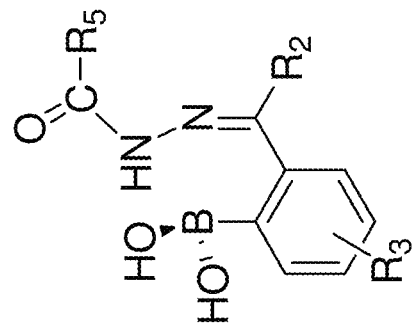
FIGS. 33A, 33B and 33C show alternate products of the reaction.
Figure 33B:
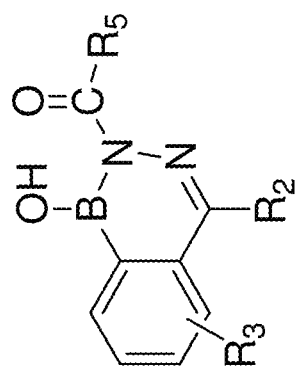
Figure 33A:
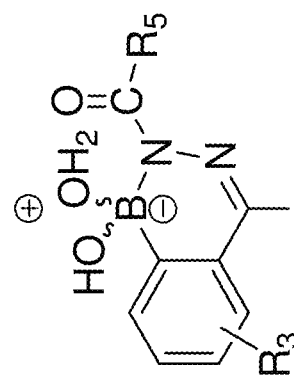
Figure 34D:
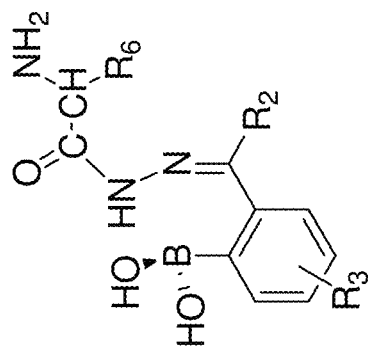
FIGS. 34A, 34B, 34C and 34D show alternate products of the reaction.
Figure 34C:
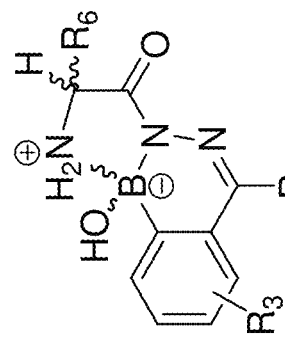
Figure 34B:
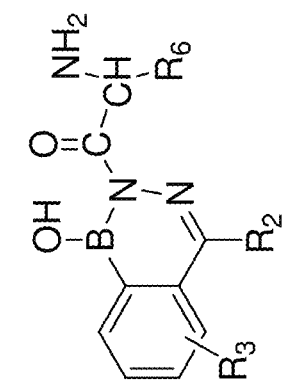
Figure 34A:
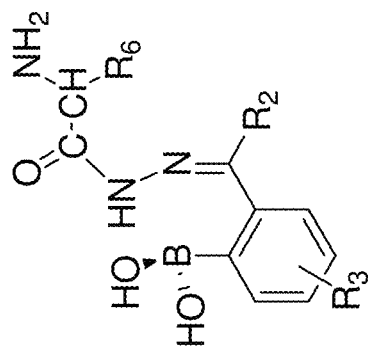
Figure 38:
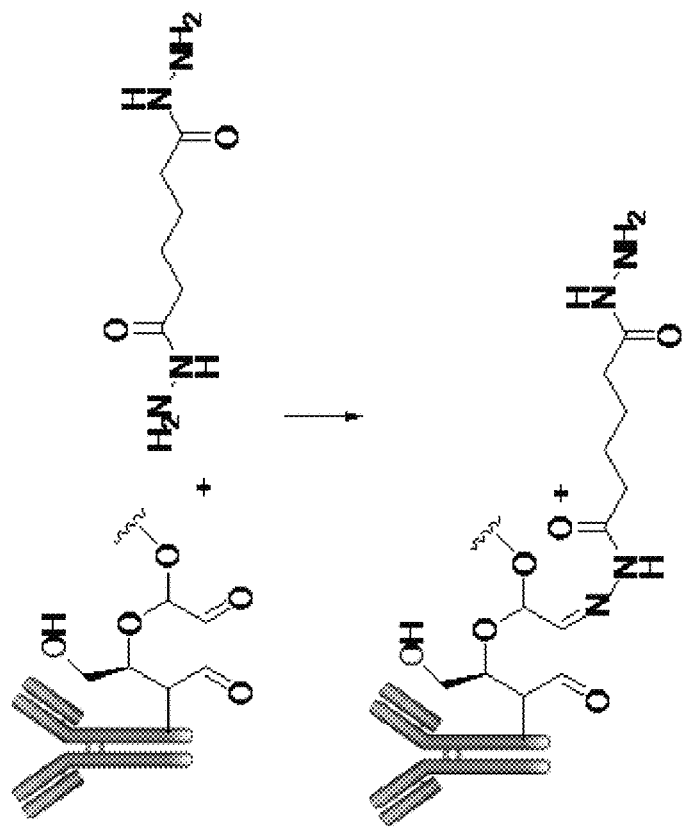
FIGS. 37 and 38 show antibody linkage reactions according to the present technology.
Figure 37:
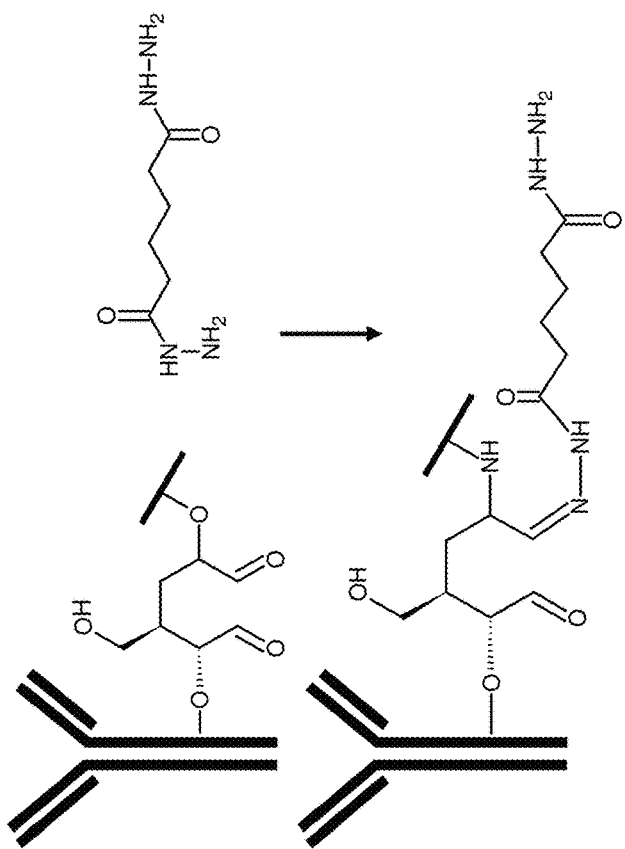
Figure 39D:
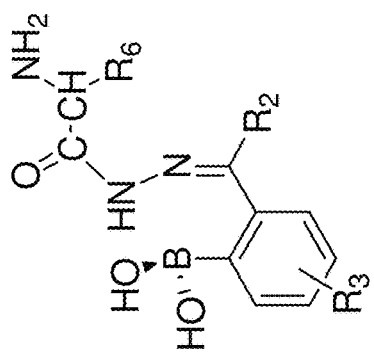
FIGS. 39A-39D and 40A-40C show carbonyl-substituted arylboronic acid moieties according to the present technology.
Figure 39C:
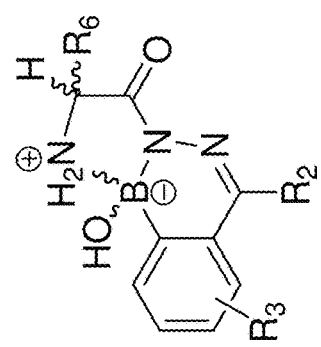
Figure 39B:
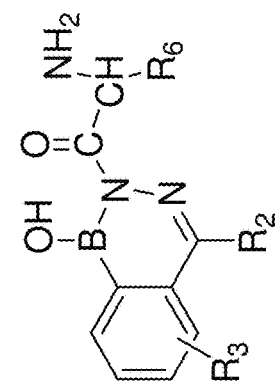
Figure 39A:
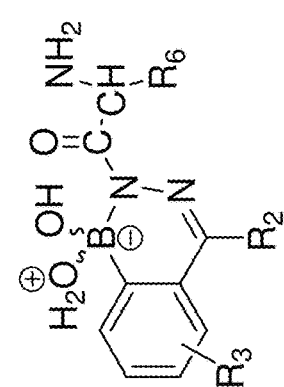
Figure 40C:
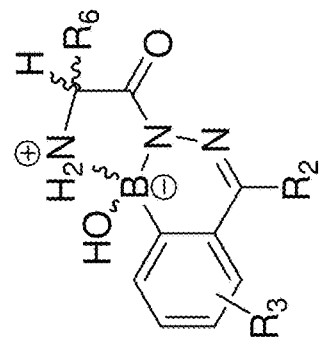
Figure 40B:
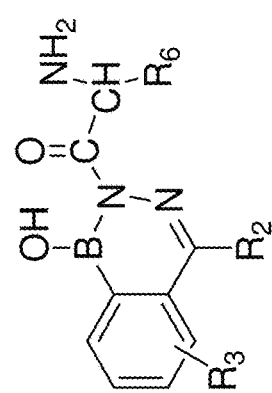
Figure 40A:
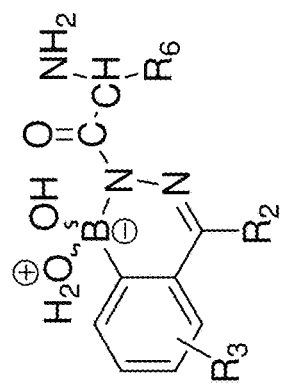
Figure 41:
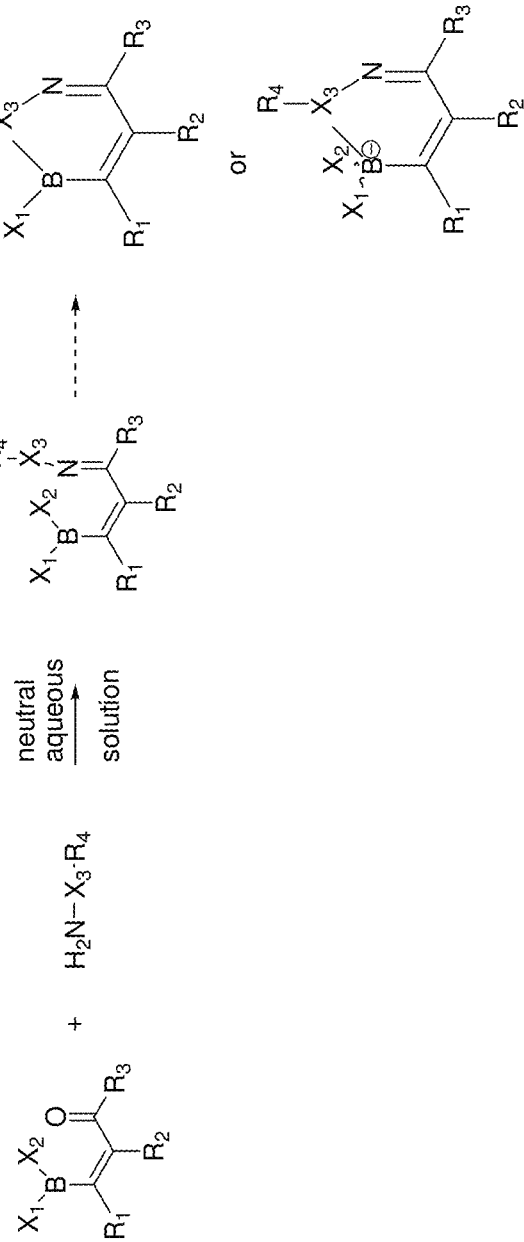
FIG. 41 shows reaction of a boron atom bonded to a sp$^2$ hybridized carbon, the boron having at least one labile substituent, conjugated with a cis-carbonyl, with a second composition having an α-effect amine, in an aqueous medium, which may proceed to form further products.

Laughlin et al. were able to image glycans in developing zebrafish by the use of click chemistry. *Cancer Biother Radiopharm.* 2009 June; 24(3): 289-302. In this study, embryonic zebrafish were incubated with an azide-peracetylated N-azidoacetylgalactosamine derivative (Ac$_4$-GalNAz), which was then reacted with a difluorinated cyclooctyne attached to a dye. See FIG. 30. A semicarbazide derivative of galactosamine is used in place of Ac$_4$-GalNAz, as shown in FIGS. 31A and 31B.

All patents and publications mentioned in this specification are expressly incorporated herein by reference in their entirety, and may be pertinent to various issues.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

What is claimed is:

1. A process comprising:
   (a) providing:
      (1) a boron compound having a boron atom covalently bonded to an sp$^2$ hybridized carbon conjugated with a cis-carbonyl, selected from the group consisting of:

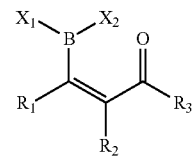

wherein:
   $X_1$, $X_2$ are independently selected from groups that can hydrolyze from the boron to yield boronic acid; and
   $R_1$, $R_2$, and $R_3$ are independently selected from the group consisting of hydrogen, organic ligands, and heterorganic ligands and optionally joined in one or more rings,
   wherein $X_1$, $X_2$, $R_1$, $R_2$, and $R_3$ exclude α-effect amines, and
   wherein the boron compound is adapted to selectively and spontaneously react with an α-effect amine at in a liquid solvent, a temperature of less than 55° C., and at a pH above 2, to at least form an adduct by formation of a covalent bond between the boron compound and the α-effect amine; and
   (2) an α-effect amine comprising an amino acid, and having an amine group bonded to an oxygen, nitrogen, or sulfur; and (b) contacting the boron compound with the α-effect amine in the liquid solvent at the temperature of less than 55° C. and at the pH above 2, to spontaneously form the adduct.

2. The process according to claim 1, wherein the solvent comprises an aqueous medium, the contacting being performed at temperatures between about −5° C. to 55° C., and at a pH between 2 and 8, and wherein the boron compound, the α-effect amine, and the solvent are bioorthogonal.

3. The process according to claim 1, wherein the α-effect amine comprises an amine group bonded to an oxygen which is reactive with the boron compound.

4. The process according to claim 1, wherein the α-effect amine comprises an amine group bonded to a nitrogen which is reactive with the boron compound.

5. The process according to claim 1, wherein the boron compound comprises a carbonyl-substituted arylboronic acid or ester.

6. The process according to claim 1, wherein the adduct undergoes a molecular rearrangement after forming an initial covalent bond between the cis-carbonyl carbon and the α-effect amine.

7. The process according to claim 1, wherein:
$R_2$ is selected from the group consisting of: H, $CH_3$; and
$R_3$ is selected from the group consisting of OH, O-alkyl, O-alkylbromide, O-alkylamine, O-alkylamide, O-alkylthiol, O-alkylthioester, alkylamine, alkylamide and alkylbromide.

8. The process according to claim 1, wherein the α-effect amine is selected from the group consisting of alpha-hydrazides of tyrosine, phenylalanine, alanine, beta-alanine, glycine, dimethylglycine, and CBz-serine.

9. The process according to claim 1, wherein the α-effect amine is selected from the group consisting of: a hydrazine; a semicarbazide, a thiosemicarbazide; a hydrazide, a thiohydrazide, a hydroxylamine, an O-alkylhydroxylamine, and an O-arylhydroxylamine.

10. The process according to claim 1, wherein the boron compound comprises a carbonyl substituted arylboronic acid selected from the group consisting of:
an ortho formyl phenylboronic acid or ester derivative;
an ortho ketone phenylboronic acid or ester derivative;
an ortho aldehyde phenylboronic acid ester derivative of an amino acid;
a ketone phenylboronic acid or ester derivative of an amino acid;
an ortho aldehyde phenylboronic acid derivatized with a reactive functional group which is orthogonal with respect to the boron compound and the α-effect amine; and
a ketone phenylboronic acid derivatized with a reactive functional group which is orthogonal with respect to the boron compound and the α-effect amine.

11. The process according to claim 1, wherein the liquid solvent is an aqueous medium having a pH of about 6-8, and the spontaneous formation of the adduct is substantially complete within a period of less than about 10 minutes at a temperature of about 0-42° C.

12. The process according to claim 1, wherein the adduct comprises a boron compound selected from the group consisting of:

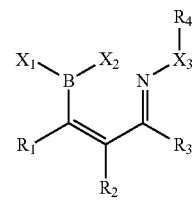

and a further product thereof formed through at least one of dehydration, interaction with the solvent, and interaction with a reactive heteroatom in the solvent, wherein:
$X_3$ is O or N; and
$R_4$ is an alkyl, aryl, or heteroatom containing group.

13. The process according to claim 12, wherein the further product comprises a dehydration product selected from the group consisting of:

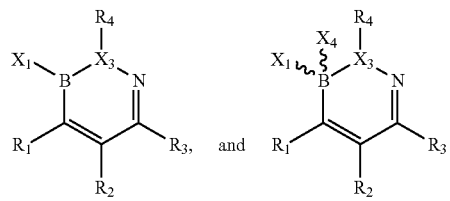

wherein $X_3$ is N, and
$X_4$ is selected from the group consisting of alkyl, aryl, heteroalkyl, heteroaryl, hydroxyl, and water.

14. The process according to claim 12, wherein $R_4$ is selected from the group consisting of: H, $CH_3$, $CH_2CH_3$, $CH_2Ph$, p-COOH Ph, o-$NH_2$Ph, o-OH Ph, COH, $COCH_3$, $COCH_2Ph$, COPh, CO-coumarin, and $CONH_2$.

15. A boron compound comprising a boron atom bonded to a $sp^2$ hybridized carbon conjugated with a cis-carbonyl and a biomolecule, selected from the group consisting of:

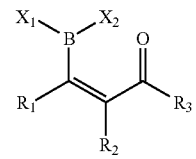

wherein:
$X_1$, $X_2$ are independently selected from groups that can hydrolyze from the boron to yield boronic acid; and
$R_1$, $R_2$, and $R_3$ are independently selected from the group consisting of hydrogen, organic ligands, and heterorganic ligands and optionally joined in one or more rings, at least one of $R_1$, $R_2$, and $R_3$ being the biomolecule;
wherein $X_1$, $X_2$, $R_1$, $R_2$, and $R_3$ exclude α-effect amines, the boron compound being selectively and spontaneously reactive to form at least a covalently bonded adduct by formation of a covalent bond between the boron compound and an α-effect amine comprising an amine group bonded to an oxygen, nitrogen, or sulfur, and non-reactive to form a covalently bonded adduct with a non α-effect amine, in an aqueous solution at pH 7 at 25° C., wherein the biomolecule comprises at least one of an amino acid, a peptide, a nucleotide, a carbohydrate, and a drug.

16. The boron compound according to claim 15, wherein the adduct is selected from the group consisting of:

(i)

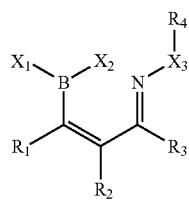

(I)

(ii) a further product formed from (I) formed through dehydration:

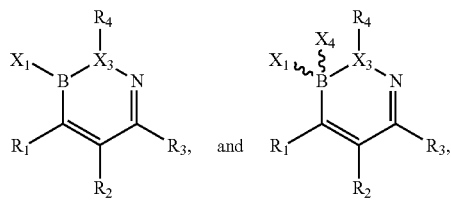

wherein $X_3$ is N, and $X_4$ is selected from the group consisting of alkyl, aryl, heteroalkyl, heteroaryl, hydroxyl and water, (iii) a further product formed from (I) through interaction with the solvent; and (iv) a further product formed from (I) through interaction with a reactive heteroatom in the solvent.

17. The boron compound according to claim 15, wherein the adduct is selected from the group consisting of:

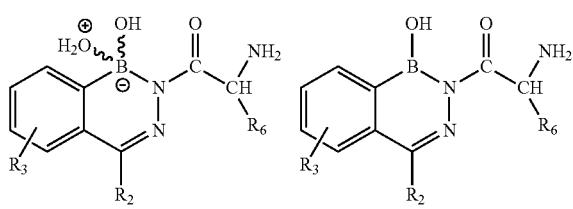

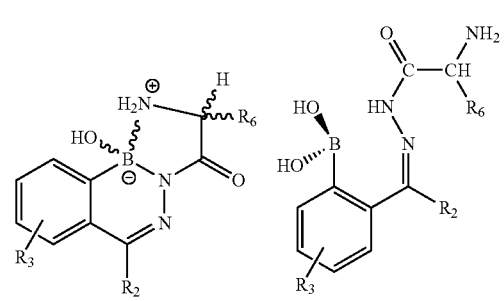

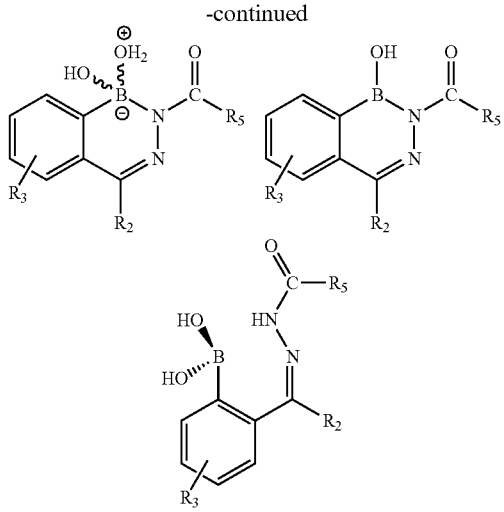

wherein:

$R_2$ is H or $CH_3$;

$R_3$ and $R_6$ are independently selected from the group consisting of alkyl or OR, wherein R is selected from the group consisting of alkyl, heteroalkyl, heteroaryl, alkylamine, alkylthiol, alkylbromide, arylbromide, $C_2$-$C_6$ alkanoyl, $CH_2Ar$ or $CH_2CH_2Ar$, wherein $R_3$ further comprises the biomolecule, in which a heteroatom of the heteroalkyl and heteroaryl is selected from the group consisting of nitrogen, oxygen, and sulfur, the Ar group of $CH_2Ar$ or $CH_2CH_2Ar$ is selected from the group consisting of a phenyl, a substituted phenyl ring, a naphtyl, a heteroaromatic ring, and a fused ring comprising at least one ring heteroatom selected from the group consisting of nitrogen, oxygen, and sulfur, a 4 to 7 member ring optionally incorporating one or more heteroatoms selected from the group consisting of oxygen, nitrogen, and sulfur, an aromatic ring optionally substituted with a fluorescent group, a sugar, and a polyethylene glycol chain; and $R_5$ is selected from the group consisting of H, $CH_3$, $CH_2CH_3$, $CH_2Ph$, Ph, substituted Ph, and $NH_2$.

18. The boron compound according to claim 15, wherein the boron compound comprises a carbonyl substituted arylboronic acid selected from the group consisting of:

an ortho formyl phenylboronic acid or ester derivative;

an ortho ketone phenylboronic acid or ester derivative;

an ortho aldehyde phenylboronic acid ester derivative of an amino acid;

a ketone phenylboronic acid or ester derivative of an amino acid;

an ortho aldehyde phenylboronic acid derivatized with a reactive functional group which is orthogonal with respect to the boron compound and the α-effect amine; and a ketone phenylboronic acid derivatized with a reactive functional group which is orthogonal with respect to the boron compound and the α-effect amine.

19. The boron compound according to claim 15, provided as a kit in combination with the α-effect amine.

20. A process comprising:
combining:
(1) a biorthogonal compound having a boron atom covalently bonded to an $sp^2$ hybridized carbon conjugated with a cis-carbonyl, selected from the group consisting of:

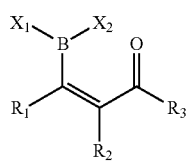

wherein:
$X_1$, $X_2$ are independently selected from groups that can hydrolyze from the boron to yield boronic acid; and
$R_1$, $R_2$, and $R_3$ are independently selected from the group consisting of hydrogen, organic ligands, and heterorganic ligands and optionally joined in one or more rings,
wherein $X_1$, $X_2$, $R_1$, $R_2$, and $R_3$ exclude α-effect amines, and
wherein the boron compound is adapted to selectively and spontaneously react with an α-effect amine at in a liquid solvent, a temperature of less than 55° C., and at a pH above 2, to at least form a covalently bonded adduct by formation of a covalent bond between the boron compound and the α-effect amine; and (2) an α-effect amine comprising an amino acid, having an amine group bonded to an oxygen, nitrogen, or sulfur, in the liquid solvent at the temperature of less than 55° C. and at the pH above 2, to spontaneously form the covalently bonded adduct between the biorthogonal compound and the α-effect amine to essential completion within 10 minutes, wherein at least one of the biorthogonal compound and the α-effect amine comprises at least one of an amino acid, a peptide, a nucleotide, a carbohydrate, a drug, a dye, a fluorophore, a radionuclide, and an isotopically enriched compound.

\* \* \* \* \*